United States Patent
Lubisch et al.

(10) Patent No.: US 7,723,384 B2
(45) Date of Patent: May 25, 2010

(54) KETO LACTAM COMPOUNDS AND USE THEREOF

(75) Inventors: Wilfried Lubisch, Heidelberg (DE); Andreas Haupt, Schwetzingen (DE); Wilfried Braje, Rinteln (DE); Herve Geneste, Neuhofen (DE)

(73) Assignee: Abbott GmbH & Co. KG., Wiesbaden (DE)

( * ) Notice: Subject to any disclaimer, the term of this patent is extended or adjusted under 35 U.S.C. 154(b) by 655 days.

(21) Appl. No.: 10/582,285

(22) PCT Filed: Dec. 10, 2004

(86) PCT No.: PCT/EP2004/014118

§ 371 (c)(1),
(2), (4) Date: Apr. 10, 2007

(87) PCT Pub. No.: WO2005/056546

PCT Pub. Date: Jun. 23, 2005

(65) Prior Publication Data

US 2007/0219182 A1  Sep. 20, 2007

(30) Foreign Application Priority Data

Dec. 11, 2003  (DE) .................. 103 58 004

(51) Int. Cl.
*C07D 403/12* (2006.01)
*C07D 401/12* (2006.01)
*C07D 223/16* (2006.01)
*A61K 31/55* (2006.01)

(52) U.S. Cl. ...................... 514/523; 540/523

(58) Field of Classification Search ............... 540/523; 514/212.07
See application file for complete search history.

(56) References Cited

FOREIGN PATENT DOCUMENTS

| DE | 10 131 543 | 1/2003 |
|---|---|---|
| WO | WO 96/02246 | 2/1996 |
| WO | WO 96/02249 | 2/1996 |
| WO | WO 96/02519 | 2/1996 |
| WO | WO 96/02520 | 2/1996 |
| WO | WO 99/02503 | 1/1999 |
| WO | WO 00/76981 | 12/2000 |

OTHER PUBLICATIONS

Schwartz J C et al *The Dopamine D3 Receptor as a Target for Antipsychotics* Novel Antipsychotic Drugs, H.Y. Meltzer, ed., Raven Press, New York (1992) pp. 135-144.
Dooley M et al *Pramipexole A Review of its Use in the Management of Early and Advanced Parkinson's Disease* Drugs and Aging vol. 12(6) (1998) pp. 495-514.

(Continued)

*Primary Examiner*—Bruck Kifle
(74) *Attorney, Agent, or Firm*—Lisa V. Mueller; Polsinelli Shughart PC

(57) ABSTRACT

The invention relates to novel keto lactam compounds, hydrogenated derivatives and tautomers thereof. These compounds have valuable therapeutic properties and are particularly suited for treating diseases that respond to the modulation of the dopamine $D_3$ receptor. The keto lactams have general formula (I), wherein: (a) represents a group of formulas (b) or (c), wherein D is bound to the nitrogen atom and W, $R^p$ and $R^q$ have the meanings cited in Claim 1; —B— represents a bond or (d), wherein $R^m$ and $R^n$ have the meanings cited in Claim 1; (e) represents a single bond or a double bond; $R^v$, $R^w$, $R^x$ and $R^y$ have the meanings cited in Claim 1; D represents a linear or branched 2 to 10-membered alkylene chain that can have, as chain members, a heteroatom group K, which is selected among O, S, S(O), S(O)$_2$, N—$R^8$, CO—O, C(O)NR$^8$ and/or 1 or 2 non-adjacent carbonyl groups and which can have a cycloalkane diyl group and/or a double or triple bond; (f) represents a saturated or monounsaturated monocyclic nitrogen heterocyclic compound having 5 to 8 cyclic members or a bicyclic saturated nitrogen heterocyclic compound having 7 to 12 cyclic members.

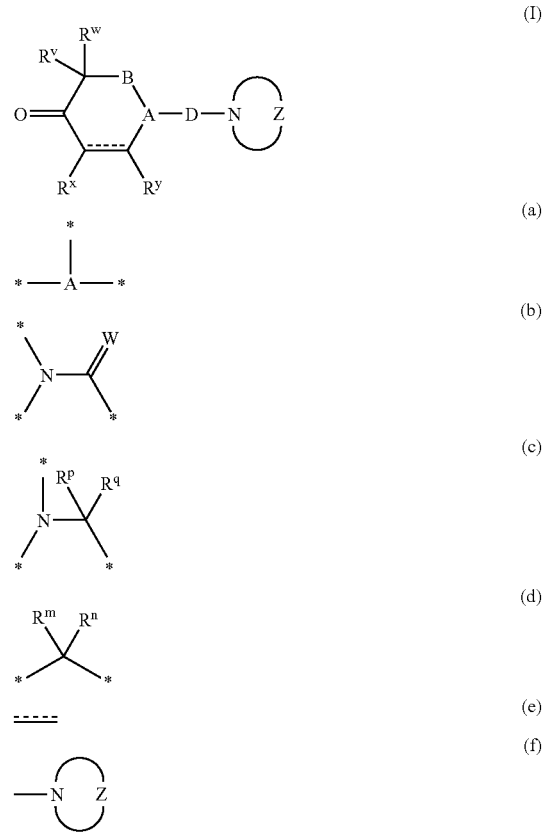

19 Claims, No Drawings

OTHER PUBLICATIONS

Joyce J N *The Dopamine D3 Receptor as a Therapeutic Target for Antipsychotic and Antiparkinsonian Drugs* Pharmacology and Therapeutics vol. 90 (2001) pp. 231-259.

Sokoloff P et al *Localization and Function of the D3 Dopamine Receptor* Arzeim. Forsch./Drug Res. vol. 42(1)(1992) pp. 224-230.

Sokoloff P et al *Molecular Cloning and Characterization of a Novel Dopamine Receptor (D3) as a Target for Neuroleptics* Nature No. 347 (1990) pp. 146-151.

Orjales A et al *New 3-benzisothiazolyl and 3-benzisoxazolylpiperazine derivatives with atypical antipsychotic binding profile* European Journal of Medical Chemistry vol. 37 (2002) pp. 721-730.

Hackling A E et al. *Dopamine D3 receptor ligands with antagonist properties* Chembiochem—A European Journal of Chemical Biology, Wiley VCH, Weinheim, vol. 3 No. 10 (2002) pp. 946-961.

Leopoldo M et al *Structure-affinity relationship study on N-'4-(4-arylpiperazin-1-yl)butyl]arylcarboxamindes as potent and selective dopamine D3 receptor ligands* Journal of Medical Chemistry, Am. Chem. Soc., Washington, D.C., vol. 45(26) pp. 5727-5735, (2002).

KETO LACTAM COMPOUNDS AND USE THEREOF

The present invention relates to novel keto lactam compounds, hydrogenated derivatives and tautomers thereof. These compounds possess valuable therapeutic properties and are suitable especially for the treatment of diseases which respond to the modulation of the dopamine $D_3$ receptor.

Neurons obtain their information from sources including G protein-coupled receptors. There are numerous substances which exert their action via these receptors. One of these is dopamine. Confirmed findings about the presence of dopamine and its physiological function as a neurotransmitter have been published. Disturbances in the dopaminergic transmitter system result in diseases of the central nervous system which include, for example, schizophrenia, depression or Parkinson's disease. One possible treatment of these and other diseases is based on the administration of substances which interact with the dopamine receptors.

Up to 1990, two subtypes of dopamine receptors were clearly defined pharmacologically, specifically the $D_1$ and $D_2$ receptors. More recently, a third subtype has been found, specifically the $D_3$ receptor, which appears to mediate some effects of antipsychotics and antiparkinsonian drugs (J. C. Schwartz et al., The Dopamine $D_3$ Receptor as a Target for Antipsychotics, in Novel Antipsychotic Drugs, H. Y. Meltzer, Ed. Raven Press, New York 1992, pages 135-144; M. Dooley et al., Drugs and Aging 1998, 12, 495-514, J. N. Joyce, Pharmacology and Therapeutics 2001, 90, p. 231-59 "The Dopamine $D_3$ Receptor as a Therapeutic Target for Antipsychotic and Antiparkinsonian Drugs").

The dopamine receptors are now divided into two families: firstly the $D_2$ group consisting of $D_2$, $D_3$ and $D_4$ receptors, secondly the $D_1$ group consisting of $D_1$ and $D_5$ receptors. While $D_1$ and $D_2$ receptors are widespread, $D_3$ receptors, in contrast, appear to be expressed regioselectively. Thus, these receptors are found preferentially in the limbic system, the projection regions of the mesolimbic dopamine system, in particular in the nucleus accumbens, but also in other regions such as the amygdala. Owing to this comparatively regioselective expression, $D_3$ receptors are considered to be a target with low side effects, and it is assumed that a selective $D_3$ ligand should have the properties of known antipsychotics but not their dopamine $D_2$ receptor-mediated neurological side effects (P. Sokoloff et al., Localization and Function of the $D_3$ Dopamine Receptor, *Arzneim. Forsch./Drug Res.* 42(1), 224 (1992); P. Sokoloff et al. Molecular Cloning and Characterization of a Novel Dopamine Receptor ($D_3$) as a Target for Neuroleptics, *Nature*, 347, 146 (1990)).

Compounds having dopamine $D_3$ receptor affinity have been described variously in the prior art, for example, in WO 96/02519, WO 96/02520, WO 96/02249, WO 96/02246, WO 97/25324, WO 00/42036, DE 10131543 and WO 99/02503. Some of these compounds have high affinities for the dopamine $D_3$ receptor. They are therefore proposed for the treatment of diseases of the central nervous system.

However, there is a fundamental need to provide further compounds with dopamine $D_3$ receptor affinity, whether it be to improve the pharmacological binding profile or because the prior art compounds cause undesired side effects, have poor cerebral availability or only low bioavailability. It is therefore an object of the invention to provide further compounds which act as selective dopamine $D_3$ receptor ligands.

This object is achieved by the derivatives of keto lactams which have the general formula I

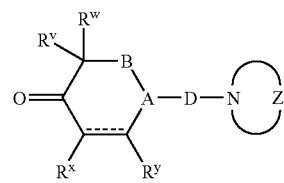

where

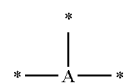

is a group of the formulae

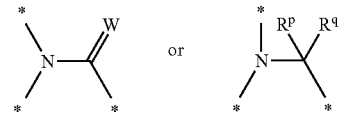

where D is bonded to the nitrogen atom and where
$R^p$ and $R^q$ are each independently selected from hydrogen, halogen, optionally substituted $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_3$-$C_6$-cycloalkyloxy, $C_3$-$C_6$-cycloalkyl-$C_1$-$C_4$-alkyloxy and optionally substituted phenyl;
W is O, S or an N—$R^z$ group where $R^z$ is selected from optionally substituted $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_3$-$C_6$-cycloalkyloxy, $C_3$-$C_6$-cycloalkyl-$C_1$-$C_4$-alkyloxy and optionally substituted phenyl
and * denotes the bonding sites;
—B— is a bond or

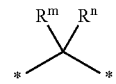

where $R^m$ and $R^n$ are each independently selected from hydrogen, halogen, optionally substituted $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_3$-$C_6$-cycloalkyloxy, $C_3$-$C_6$-cycloalkyl-$C_1$-$C_4$-alkyloxy and optionally substituted phenyl, or, when the nitrogen in the A group is bonded to B, may also be a carbonyl group, and * denotes the bonding sites;
⁻⁻⁻⁻⁻ represents a single bond or a double bond;
$R^v$, $R^w$ are each independently hydrogen, halogen, optionally substituted $C_1$-$C_6$-alkyl, $C_1$-$C_6$-alkoxy, $C_2$-$C_6$-alkenyl, $C_2$-$C_6$-alkynyl, $C_3$-$C_6$-cycloalkyloxy, $C_3$-$C_6$-cycloalkyl-$C_1$-$C_4$-alkyloxy or $C_3$-$C_6$-cycloalkyl;
$R^x$, $R^y$ are each independently hydrogen, halogen, optionally substituted $C_1$-$C_6$-alkyl, $C_1$-$C_6$-alkoxy, $C_2$-$C_6$-alkenyl, $C_2$-$C_6$-alkynyl, $C_3$-$C_6$-cycloalkyloxy, $C_3$-$C_6$-cycloalkyl-$C_1$-$C_4$-alkyloxy or $C_3$-$C_6$-cycloalkyl, or
$R^x$, $R^y$ together with the carbon atoms to which they are bonded, may also form a fused phenyl ring or a fused 5- or 6-membered aromatic heterocycle which has 1, 2, 3 or 4 heteroatoms which are selected from N, O and S, where the fused phenyl ring and the fused aromatic heterocycle may have 1, 2 or 3 substituents which are selected from optionally substituted $C_1$-$C_6$-alkyl, CN, $OR^1$, $NR^2R^3$, $NO_2$, $SR^4$, $SO_2R^4$, $SO_2NR^2R^3$, $CONR^2R^3$, $COOR^5$, $COR^6$, $C_1$-$C_4$-haloalkoxy, $C_2$-$C_6$-alkenyl, $C_2$-$C_6$-alkynyl, $C_2$-$C_6$-alkenyloxy, $C_2$-$C_6$-alkynyloxy, $C_3$-$C_6$-cycloalkyl, $C_3$-$C_6$-cycloalkyloxy and halogen; where $R^1, R^2, R^3, R^4, R^5$ and $R^6$ are each independently H, optionally substituted $C_1$-$C_6$-alkyl or optionally substituted phenyl, where $R^3$ may also be a $COR^7$ group where $R^7$ is hydrogen, optionally substituted $C_1$-$C_4$-alkyl or optionally substituted phenyl, where $R^2$ with $R^3$ may also together form a 5- or 6-membered, saturated or unsaturated carbocycle which may have a heteroatom selected from O, S and $NR^8$ as a ring member, where $R^8$ is hydrogen or $C_1$-$C_4$-alkyl, D is a linear or branched 2- to 10-membered alkylene chain which may have, as chain members, a heteroatom group K which is selected from O, S, S(O), S(O)$_2$, N—$R^8$, CO—O, C(O)$NR^8$, and/or 1 or 2 nonadjacent carbonyl groups and which may include a cycloalkanediyl group and/or may have a double or triple bond;

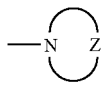

is a saturated or monounsaturated, monocyclic nitrogen heterocycle having from 5 to 8 ring members or a bicyclic saturated nitrogen heterocycle having from 7 to 12 ring members, where the mono- and the bicyclic nitrogen heterocycle optionally has, as a ring member, a further heteroatom selected from oxygen, sulfur or nitrogen, where the mono- or bicyclic nitrogen heterocycle may be unsubstituted or bears an $R^a$ radical, where $R^a$ is $C_1$-$C_{10}$-alkyl, $C_2$-$C_{10}$-alkenyl, $C_1$-$C_{10}$-alkoxycarbonyl, $C_1$-$C_{10}$-alkylcarbonyl, $C_1$-$C_{10}$-alkylsulfonyl, $C_1$-$C_{10}$-cyanoalkyl, $C_3$-$C_{10}$-cycloalkyl, $C_3$-$C_{10}$-cycloalkyl-$C_1$-$C_4$-alkyl, $C_3$-$C_{10}$-heterocycloalkyl-$C_1$-$C_4$-alkyl, $C_3$-$C_{10}$-cycloalkylcarbonyl, $C_3$-$C_{10}$-cycloalkylcarbonyl-$C_1$-$C_4$-alkyl, phenylcarbonyl, phenylcarbonyl-$C_1$-$C_4$-alkyl, phenoxycarbonyl, phenyl-$C_1$-$C_{10}$-alkyloxycarbonyl, 3- to 8-membered heterocyclylcarbonyl or 3- to 8-membered heterocyclylcarbonyl-$C_1$-$C_4$-alkyl, where heterocyclyl in the aforementioned radicals may have one, two or three heteroatoms selected from S, O and N, and where the last 6 radicals may have, on the heterocycle or on the phenyl ring, 1, 2 or 3 substituents $R^b$ which are each independently selected from optionally substituted $C_1$-$C_6$-alkyl, $C_2$-$C_6$-alkenyl, $C_2$-$C_6$-alkynyl, $C_3$-$C_6$-cycloalkyl, $C_4$-$C_{10}$-bicycloalkyl and $C_6$-$C_{10}$-tricycloalkyl, where the last three groups may optionally be substituted by halogen or $C_1$-$C_4$-alkyl, halogen, CN, $OR^1$, $NR^2R^3$, $NO_2$, $SR^4$, $SO_2R^5$, $CONR^2R^3$, $SO_2NR^2R^3$, $COOR^5$, $COR^6$, O—$COR^6$, 5- or 6-membered heterocyclyl having 1, 2 or 3 heteroatoms selected from O, S and N, and phenyl, where phenyl and heterocyclyl in the last two substituents $R^b$ may optionally bear one or two substituents which are each independently selected from $C_1$-$C_4$-alkyl, $C_1$-$C_4$-alkoxy, $NR^2R^3$, CN, $C_1$-$C_2$-fluoroalkyl and halogen, and where 2 substituents $R^b$ bonded to adjacent carbon atoms of the and halogen, and where 2 substituents $R^b$ bonded to adjacent carbon atoms of the aromatic radical may together be $C_3$- or $C_4$-alkylene, or, together with the carbon atoms to which they are bonded, may be a fused-on, unsaturated 5- or 6-membered carbocycle or a 5- or 6-membered heterocycle having 1 or 2 nitrogen atoms as ring members; or $R^a$ is an E-Ar group wherein E is a bond or linear or branched alkylene having from 1 to 4 carbon atoms and in particular (CH$_2$)$_p$ where p is 0, 1, 2, 3 or 4, and Ar is selected from phenyl, naphthyl and 5- or 6-membered heteroaryl which has one, two or three heteroatoms selected from S, O and N as ring members and which may optionally have 1, 2 or 3 of the aforementioned substituents $R^b$; or

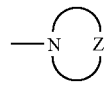

is a saturated monocyclic nitrogen heterocycle having from 5 to 7 ring atoms which bears a fused-on benzene ring of the formula

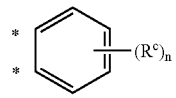

where * denotes the bonding sites to the saturated monocyclic heterocycle; $R^c$ may be the same or different and is as defined for $R^b$, and n is 0, 1, 2 or 3;

where

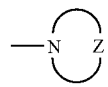

may optionally also have 1, 2, 3 or 4 further $C_1$-$C_4$-alkyl groups as substituents;

the physiologically acceptable acid addition salts of this compound and the tautomer of the formula I'

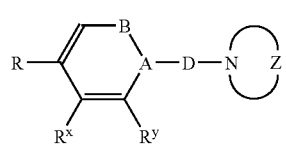

(I)

where R is halogen, an O—$R^1$ group where $R^1$ is as defined above, or an O—C(O)$R^9$ group where $R^9$ is hydrogen, optionally substituted $C_1$-$C_6$-alkyl, benzyl or phenyl, where the last two radicals are optionally substituted by one or two radicals which are each independently selected from $C_1$-$C_4$-alkyl, OH, $C_1$-$C_4$-alkoxy, $NR^2R^3$, CN, $C_1$-$C_2$-fluoroalkyl or halogen, and the physiologically acceptable acid addition salts of the tautomer I'.

The present invention therefore provides the compounds of the general formula I, the tautomers of the formula I' and the physiologically tolerated acid addition salts of the compounds I and their tautomers I'.

The present invention also provides for the use of compounds of the general formula I, the tautomers of the formula I' and the physiologically tolerated acid addition salts of the compounds I and their tautomers I' for producing a pharmaceutical composition for treating diseases which respond to the influence of dopamine $D_3$ receptor antagonists or agonists.

The diseases which respond to the influence of dopamine $D_3$ receptor antagonists or agonists include in particular disorders and diseases of the central nervous system, especially affective disorders, neurotic disorders, stress disorders and somatoform disorders and psychoses, specifically schizophrenia and depression and also renal function disorders, especially renal function disorders caused by diabetes mellitus (see WO 00/67847).

According to the invention, the aforementioned indications are treated by using at least one compound of the general formula I, a tautomer of the general formula I' or a physiologically tolerated acid addition salt of a compound I or of a tautomer I'. When the compounds of the formula I or their tautomers I' have one or more centers of asymmetry, it is also possible to employ mixtures of enantiomers, especially racemates, mixtures of diastereomers, mixtures of tautomers, but preferably the particular substantially pure enantiomers, diastereomers and tautomers.

It is likewise possible to use physiologically tolerated salts of the compounds of the formula I and of the tautomers I', in particular acid addition salts with physiologically tolerated acids. Examples of useful physiologically tolerated organic and inorganic acids include hydrochloric acid, hydrobromic acid, phosphoric acid, sulfuric acid, $C_1$-$C_4$-alkylsulfonic acids such as methanesulfonic acid, aromatic sulfonic acids such as benzenesulfonic acid and toluenesulfonic acid, oxalic acid, maleic acid, fumaric acid, lactic acid, tartaric acid, adipic acid and benzoic acid. Further acids which can be used are described in Fortschritte der Arzneimittelforschung, volume 10, pages 224 ff., Birkhäuser Verlag, Basle and Stuttgart, 1966.

Halogen here and hereinafter is fluorine, chlorine, bromine or iodine.

$C_n$-$C_m$-alkyl (including in radicals such as alkoxy, alkoxyalkyl, alkylthio, alkylamino, dialkylamino, alkylcarbonyl, etc.) is a straight-chain or branched alkyl group having n to m carbon atoms, for example 1 to 6 and especially 1 to 4 carbon atoms. Examples of an alkyl group are methyl, ethyl, n-propyl, isopropyl, n-butyl, 2-butyl, isobutyl, tert-butyl, n-pentyl, 2-pentyl, neopentyl, n-hexyl and the like.

The expression "optionally substituted $C_n$-$C_m$-alkyl" represents an alkyl radical which has from n to m carbon atoms, which may be partly or fully substituted by halogen, in particular by chlorine or fluorine, and which may have one or more, for example 1, 2 or 3, non-halogen substituents which are selected from halogen, CN, $C_3$-$C_7$-cycloalkyl, $C_3$-$C_7$-heterocycloalkyl, optionally substituted phenyl, $OR^{11}$, $COOR^{11}$, $NR^{12}R^{13}$, $SO_2NR^{12}R^{13}$, $CONR^{12}R^{13}$, $O-CONR^{12}R^{13}$, $S-R^{14}$, $SOR^{15}$, $SO_2R^{15}$, $OCOR^{16}$ and $COR^{16}$. In these, $R^{11}$ is as defined for $R^1$, $R^{12}$ is as defined for $R^2$, $R^{13}$ is as defined for $R^3$, $R^{14}$ is as defined for $R^4$, $R^{15}$ is as defined for $R^5$ and $R^{16}$ is as defined for $R^6$. In particular, $R^{11}$-$R^{16}$ are hydrogen, $C_1$-$C_4$-alkyl, $C_1$-$C_4$-haloalkyl, $C_3$-$C_7$-cycloalkyl, optionally substituted benzyl or optionally substituted phenyl. Preferred substituents on alkyl are selected from OH, $C_1$-$C_4$-alkoxy, halogen, $C_3$-$C_7$-cycloalkyl and optionally substituted phenyl. In the case of OH, $C_1$-$C_4$-alkoxy, $C_3$-$C_7$-cycloalkyl and phenyl there is in particular only one substituent. Such radicals are also referred to hereinafter as $C_1$-$C_4$-alkoxy-$C_1$-$C_6$-alkyl such as methoxymethyl, 1- or 2-methoxyethyl, 1-methoxy-1-methylethyl or 2-methoxy-1-methylethyl, 1-, 2- or 3-methoxypropyl, ethoxymethyl, 1- or 2-ethoxyethyl, hydroxy-$C_1$-$C_6$-alkyl, 1-hydroxymethyl, 1- or 2-hydroxyethyl, 1-hydroxy-1-methylethyl, 1-, 2- or 3-hydroxypropyl etc., $C_3$-$C_6$-cycloalkyl-$C_1$-$C_6$-alkyl such as cyclopropylmethyl, cyclohexylmethyl or phenyl-$C_1$-$C_6$-alkyl. In the case of halogen substituents, these radicals are also referred to as haloalkyl.

$C_1$-$C_6$-Haloalkyl (including in radicals such as $C_1$-$C_6$-haloalkoxy) represents an alkyl group which has 1 to 6 and in particular 1 to 4 carbon atoms as defined above, in which all or some, for example 1, 2, 3, 4 or 5, of the hydrogen atoms are replaced by halogen atoms, in particular by chlorine or fluorine. Preferred haloalkyl is $C_1$-$C_2$-fluoroalkyl or $C_1$-$C_2$-fluorochloroalkyl, in particular $CF_3$, $CHF_2$, $CF_2Cl$, $CH_2F$, $CH_2CF_3$.

$C_3$-$C_{10}$-cycloalkyl, including in radicals such as cycloalkylalkyl, cycloalkylcarbonyl and cycloalkylcarbonylalkyl, represents a cycloaliphatic radical having 3 to 10 and preferably 3 to 6 carbon atoms, such as cyclopropyl, cyclobutyl, cyclopentyl, cyclohexyl, cycloheptyl and cyclooctyl.

$C_3$-$C_{10}$-Heterocycloalkyl, including in radicals such as heterocycloalkylalkyl, heterocycloalkylcarbonyl and heterocycloalkylcarbonylalkyl, represents a saturated heterocyclic radical having ring members, where 1, 2 or 3 ring members are a heteroatom selected from N, O and S, such as oxiranyl, oxetanyl, aziranyl, azetanyl, tetrahydrofurfuryl, tetrahydrothienyl, pyrrolidinyl, pyrazolinyl, imidazolinyl, piperidinyl, piperazinyl or morpholinyl.

$C_4$-$C_{10}$-Bicycloalkyl represents a bicycloaliphatic radical having 4 to 10 carbon atoms as in bicyclo[2.1.0]pentyl, bicyclo[2.1.1]hexyl, bicyclo[3.1.0]hexyl, bicyclo[2.2.1]heptanyl, bicyclo[3.2.0]heptanyl, bicyclo[2.2.2]octanyl, bicyclo[3.2.1]octanyl, bicyclo[3.3.1]nonyl and bicyclo[4.4.0]decyl.

$C_6$-$C_{10}$-Tricycloalkyl represents a tricycloaliphatic radical having 6 to 10 carbon atoms as in adamantyl.

$C_2$-$C_6$-alkenyl represents a monounsaturated linear or branched hydrocarbon radical having 2, 3, 4, 5 or 6 carbon atoms, for example vinyl, allyl (2-propen-1-yl), 1-propen-1-yl, 2-propen-2-yl, methallyl (2-methylprop-2-en-1-yl) and the like. $C_3$-$C_4$-alkenyl is in particular allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl, 2-ethylprop-2-en-1-yl.

$C_2$-$C_6$-Haloalkenyl represents an alkenyl group as defined above, in which all or some, for example 1, 2, 3, 4 or 5, of the hydrogen atoms are replaced by halogen atoms, in particular by chlorine or fluorine.

$C_2$-$C_6$-alkynyl represents a hydrocarbon radical having 2, 3, 4, 5 or 6 carbon atoms and having a triple bond, for example propargyl (2-propyn-1-yl), 1-methylprop-2-yn-1-yl, 2-butyn-1-yl, 3-butyn-1-yl, 2-pentyn-1-yl, 1-pentyn-3-yl, etc.

$C_2$-$C_6$-Haloalkynyl represents an alkenyl group as defined above, in which all or some, for example 1, 2, 3, 4 or 5, of the hydrogen atoms are replaced by halogen atoms, in particular by chlorine or fluorine.

phenyl-$C_1$-$C_4$-alkyl represents a $C_1$-$C_4$-alkyl radical as defined above, in which a hydrogen atom is replaced by a phenyl radical, as in benzyl or 2-phenylethyl.

Optionally substituted phenyl represents phenyl that optionally has one or more, for example 1, 2 or 3, of the following substituents: halogen, nitro, cyano, optionally substituted $C_1$-$C_4$-alkyl, $C_2$-$C_6$-alkenyl, $C_2$-$C_6$-alkynyl, $C_3$-$C_6$-cycloalkyl, $C_1$-$C_4$-haloalkyl, $C_1$-$C_4$-alkoxy, $OR^{21}$, $COOR^{21}$, $NR^{22}R^{23}$, $SO_2NR^{22}R^{23}$, $CONR^{22}R^{23}$, O—$CONR^{22}R^{23}$, S—$R^{24}$, $SOR^{25}$, $SO_2R^{25}$, $OCOR^{26}$ and $COR^{26}$. Examples of suitable substituents on phenyl are in particular halogen, $C_1$-$C_4$-alkyl, $C_2$-$C_6$-alkenyl, $C_2$-$C_6$-alkynyl, $C_3$-$C_6$-cycloalkyl, $C_1$-$C_4$-haloalkyl, $C_1$-$C_4$-alkoxy, $C_1$-$C_4$-alkoxy-$C_1$-$C_4$-alkyl, hydroxy-$C_1$-$C_4$-alkyl, hydroxy, nitro, $NH_2$, cyano, COOH, $C_1$-$C_4$-alkoxycarbonyl, $C_1$-$C_4$-alkylcarbonyl, $C_1$-$C_4$-alkylamino, di($C_1$-$C_4$-alkyl)amino, $C_1$-$C_4$-alkylsulfonyl, $C_1$-$C_4$-alkylsulfonylamino and/or $C_1$-$C_4$-alkylaminosulfonyl. In these, $R^{21}$ is as defined for $R^1$, $R^{22}$ is as defined for $R^2$, $R^{23}$ is as defined for $R^3$, $R^{24}$ is as defined for $R^4$, $R^{25}$ is as defined for $R^5$, and $R^{26}$ is as defined for $R^6$. In particular, $R^{21}$-$R^{26}$ are hydrogen, $C_1$-$C_4$-alkyl, $C_1$-$C_4$-haloalkyl, $C_3$-$C_7$-cycloalkyl, optionally substituted benzyl or optionally substituted phenyl.

The term "alkylene" encompasses in principle straight-chain or branched radicals having preferably from 2 to 10 and more preferably from 3 to 8 carbon atoms such as prop-1,2-ylene, prop-1,3-ylene, but-1,2-ylene, but-1,3-ylene, but-1,4-ylene, 2-methylprop-1,3-ylene, pent-1,2-ylene, pent-1,3-ylene, pent-1,4-ylene, pent-1,5-ylene, pent-2,3-ylene, pent-2,4-ylene, 1-methylbut-1,4-ylene, 2-methylbut-1,4-ylene, hex-1,3-ylene, hex-2,4-ylene, hex-1,4-ylene, hex-1,5-ylene, hex-1,6-ylene and the like. $C_0$-alkylene represents a single bond, $C_1$-alkylene represents methylene and $C_2$-alkylene represents 1,1-ethylene or 1,2-ethylene.

The term 3 to 8 membered heterocyclyl encompasses saturated (=heterocycloalkyl), partly unsaturated heterocyclic radicals and aromatic heterocycles (heteroaryl) of ring size 3, 4, 5, 6, 7 and 8, in particular of ring size 5 or 6, having 1, 2 or 3 heteroatoms as ring members. The heteroatoms in this case are selected from O, S and N.

Examples of saturated 3- to 8-membered heterocyclyl are oxiranyl, oxetanyl, aziranyl, piperidinyl, piperazinyl, morpholinyl, pyrrolidinyl, oxazolidinyl, tetrahydrofuryl, dioxolanyl, dioxanyl, hexahydroazepinyl, hexyhydrooxepinyl, and hexahydrothiepinyl.

Examples of partly unsaturated 3- to 8-membered heterocyclyl are di- and tetrahydropyridinyl, pyrrolinyl, oxazolinyl, dihydrofuryl, tetrahydroazepinyl, tetrahydrooxepinyl, and tetrahydrothiepinyl.

Examples of 5-membered heteroaromatic radicals (=5-membered heteroaryl) are those having 1, 2, 3 or 4 heteroatoms as ring members which are selected independently of one another from O, N and S, for example pyrrole, thiophene, furan, oxazole, isoxazole, selected from O, N and S, for example pyrrole, thiophene, furan, oxazole, isoxazole, thiazole, isothiazole, imidazole, 1,2,3-thiadiazole, 1,2,4-thiadiazole, 1,3,4-thiadiazole, 1,2,3-triazole, 1,2,4-triazole, 1,3,4-triazole, tetrazole. Examples of 6-membered heteroaromatic radicals (=6-membered heteroaryl) having 1 or 2 nitrogen atoms as ring members are in particular 2-, 3- or 4-pyridinyl, 2-, 4- or 5-pyrimidinyl, 2- or 3-pyrazinyl and 3- or 4-pyridazinyl. The 6-membered heteroaromatic radicals may have the substituents specified above and/or be fused with a nonaromatic or aromatic carbocycle, in particular a benzene or cyclohexene ring as in benzo[b]pyridine (=quinoline), benzo[c]pyridine(isoquinoline), benzo[b]pyrimidine(quinazoline), cinnoline, phthalazine or quinoxaline. In the 5- or 6-membered heteroaromatic Ar radicals, the bonding to the $(CH_2)_p$ group is preferably via a carbon atom.

In connection with the D group, the two bonding sites of the alkylene chain are generally not on the same carbon atom but rather form, optionally together with the heteroatom group K and/or the carbonyl group, an at least two-, preferably at least three- and in particular at least four-membered chain which separates the nitrogen atom in the A group from the nitrogen atom of the nitrogen heterocycle NZ by at least 3, preferably by at least 4 and in particular by at least 5 bonds from one another. When D has no carbonyl group and no heteroatom group K, D comprises preferably from 3 to 10 carbon atoms, in particular from 4 to 8 carbon atoms and more preferably from 4 to 6 carbon atoms as chain members. The chain between the atom A and the nitrogen atom of NZ then has at least 3 and in particular at least 4 carbon atoms. When D has a carbonyl group or a heteroatom group K, D comprises, in addition to these groups, generally from 1 to 10 carbon atoms, in particular from 2 to 8 carbon atoms and especially from 3 to 5 carbon atoms as chain members. The number of chain members including the K group and/or the carbonyl group is selected such that the nitrogen atom in the A group is separated from the nitrogen atom of the nitrogen heterocycle NZ by at least 3, preferably by at least 4 and in particular by at least 5 bonds from one another. Moreover, the saturated C—C bonds in alkylene may be replaced by unsaturated bonds (alkenylene; alkynylene). Thus, straight-chain or branched unsaturated radicals can arise, whose number and arrangement of the carbon atoms corresponds to that of the aforementioned alkylene radicals, except that one or more single bonds have been replaced by corresponding unsaturated double or triple bonds. Also, D may comprise a cycloalkanediyl radical, preferably a $C_3$-$C_7$-cycloalkanediyl radical, in particular a $C_4$-$C_7$-cycloalkane-1,2-, -1,3- or -1,4-diyl radical, for example cyclopropane-1,2-diyl, cyclobutane-1,2- or -1,3-diyl, cyclopentane-1,2- or -1,3-diyl, cyclohexane-1,2-, -1,3- or -1,4-diyl radical, or a cycloheptane-1,2-, -1,3- or 1,4-diyl radical. This cycloalkanediyl radical is part of the chain D. In other words, some of the cycloalkanediyl radicals form the chain D with the remaining chain members, the smaller part of the cycloalkanediyl radical being crucial with regard to the separation of the nitrogen atoms into B and NZ.

When the alkylene group in D comprises at least one heteroatom, a heteroatom group K and/or a carbonyl group, these may be arranged in any position in the alkylene chain. The heteroatom is preferably not bonded to the nitrogen atom of the A group or to the nitrogen atom of NZ. A carbonyl group is preferably bonded to the nitrogen atom of the A group or to the nitrogen atom of the NZ group.

Examples of suitable D groups are: $(CH_2)_k$ where k=2, 3, 4, 5, 6, 7, 8, 9 or 10, $CH(CH_3)(CH_2)_l$ with l=1, 2, 3, 4, 5, 6, 7, 8 or 9, $CH_2CH(CH_3)(CH_2)_{k'}$ with k'=0, 1, 2, 3, 4, 5, 6, 7 or 8, cis- and trans-$CH_2$—CH=CH—$CH_2$, $CH_2$—C($CH_3$)=CH—$CH_2$, $CH_2CH_2CH$=$CHCH_2$, $CH_2CH_2C(CH_3)$=$CHCH_2$, $CH_2C$(=$CH_2$)$CH_2$, $CH_2CH_2CH(CH_3)CH_2$, $C(O)(CH_2)_l$, $C(O)$—$CH_2CH$=$CHCH_2$, $C(O)$—$CH_2C(CH_3)$=$CHCH_2$, $C(O)$—$CH_2C$(=$CH_2$)$CH_2$, $C(O)$—$CH_2CH(CH_3)CH_2$,

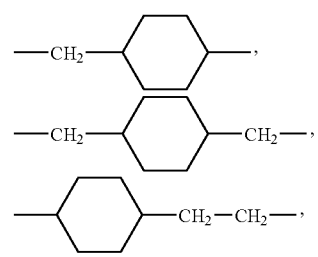

-continued

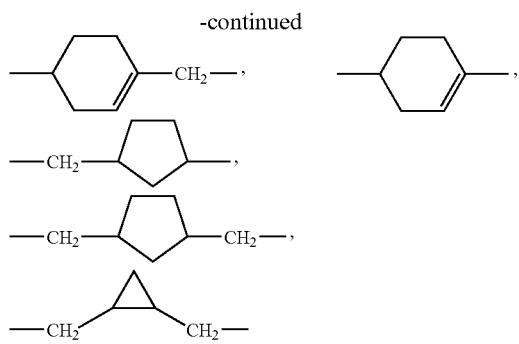

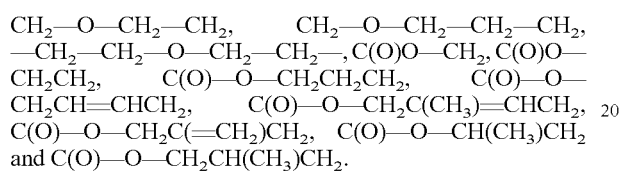

$CH_2$—O—$CH_2$—$CH_2$, $CH_2$—O—$CH_2$—$CH_2$—$CH_2$, —$CH_2$—$CH_2$—O—$CH_2$—$CH_2$—, C(O)O—$CH_2$, C(O)O—$CH_2CH_2$, C(O)—O—$CH_2CH_2CH_2$, C(O)—O—$CH_2$CH=$CHCH_2$, C(O)—O—$CH_2$C($CH_3$)=$CHCH_2$, C(O)—O—$CH_2$C(=$CH_2$)$CH_2$, C(O)—O—CH($CH_3$)$CH_2$ and C(O)—O—$CH_2$CH($CH_3$)$CH_2$.

With regard to the use of the inventive compounds as dopamine $D_3$ receptor ligands, particular preference is given to those compounds I where D in formula I or I' is $C_3$-$C_{10}$-alkylene, in particular $C_4$-$C_8$-alkylene and especially $C_4$-$C_6$-alkylene, which may have a double bond, or C(O)$C_2$-$C_9$-alkylene, in particular C(O)$C_3$-$C_8$-alkylene and especially C(O)$C_3$-$C_5$-alkylene, which may have a double bond. In particular, D is a $(CH_2)_k$ group or a C(O)$(CH_2)_l$, where k and l are each independently as defined above and are in particular each an integer from 3 to 8. More preferably, k is 4, 5 or 6 and l is 3, 4 or 5.

When A is a

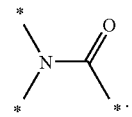

group or B is a carbonyl group, D is preferably $C_3$-$C_{10}$-alkylene, in particular $C_4$-$C_8$-alkylene and especially $C_4$-$C_6$-alkylene, which may have a double bond, especially $C_4$-$C_6$-alkylene which may have a double bond, and especially $(CH_2)_k$ where k is as defined above, in particular as defined above with preference.

W is in particular oxygen.

When A is

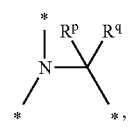

D is preferably a C(O)$C_2$-$C_9$-alkylene group, in particular C(O)$C_3$-$C_8$-alkylene, which may have a double bond. In particular D is a C(O)$(CH_2)_l$, where l is as defined above and is in particular 3, 4 or 5.

In a first embodiment of the invention, B in the formulae I and I' is a carbonyl group or a $CR'''R''$ group, where $R'''$ and $R''$ are each as defined above and are in particular hydrogen or $C_1$-$C_4$-alkyl. In particular, at least one of the $R'''$ or $R''$ radicals and especially both $R'''$ and $R''$ radicals are hydrogen.

In a second embodiment of the invention, B in the formulae I and I' is a bond.

With regard to the use of the inventive compounds I and I' as dopamine $D_3$ receptor ligands, preference is given to those compounds I and I' where the nitrogen atom of the A group is joined to the carbon atom which bears the $R^x$ group.

In particular, A is a group of the formula

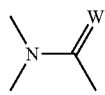

When A is a group of the formula

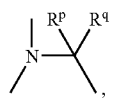

$R^p$ and $R^q$ are each independently in particular hydrogen or $C_1$-$C_4$-alkyl. In particular, at least one of the $R^p$ or $R^q$ radicals and especially both $R^p$ and $R^q$ radicals are hydrogen.

The $R^v$ and $R^w$ radicals are each independently hydrogen or $C_1$-$C_4$-alkyl. In particular, at least one of the $R^v$ or $R^w$ radicals and especially both $R^v$ and $R^w$ radicals are hydrogen.

Among the compounds of the formula I, preference is given to those compounds where $R^x$ and $R^y$, together with the carbon atoms to which they are bonded, are a fused benzene ring or a fused 5- or 6-membered aromatic heterocycle which has 1, 2, 3 or 4 heteroatoms which are selected from N, O and S, where the fused phenyl ring and the fused aromatic heterocycle may have 1, 2 or 3 substituents which are selected from $C_1$-$C_4$-alkyl, $C_1$-$C_4$-hydroxyalkyl, $C_1$-$C_4$-alkoxy-$C_1$-$C_4$-alkyl, CN, $OR^1$, $NR^2R^3$, $NO_2$, $SR^4$, $SO_2R^4$, $SO_2NR^2R^3$, $CONR^2R^3$, $COOR^5$, $COR^6$, $C_1$-$C_2$-fluoroalkyl, $C_1$-$C_2$-fluoroalkoxy, $C_2$-$C_6$-alkenyl, $C_2$-$C_6$-alkynyl, $C_2$-$C_6$-alkenyloxy, $C_2$-$C_6$-alkynyloxy, $C_3$-$C_6$-cycloalkyl, $C_3$-$C_6$-cycloalkyl and halogen; where $R^1$, $R^2$, $R^3$, $R^4$, $R^5$ and $R^6$ are each independently as defined above. Preferred substituents are $C_1$-$C_4$-alkyl, $C_1$-$C_4$-haloalkyl, $C_1$-$C_4$-alkoxy and halogen. Among these, preference is given in particular to those compounds of the formula I where $R^x$ and $R^y$, together with the carbon atoms to which they are bonded, are a fused benzene ring optionally substituted in the manner described above.

In another embodiment of the invention, $R^x$ and $R^y$ are each independently hydrogen, $C_1$-$C_6$-alkyl which is optionally substituted by OH, halogen, CN, $C_1$-$C_4$-alkoxy or optionally substituted phenyl, $C_1$-$C_6$-alkoxy, $C_2$-$C_6$-alkenyl, $C_2$-$C_6$-alkynyl or $C_3$-$C_6$-cycloalkyl, and in particular hydrogen or $C_1$-$C_4$-alkyl. In that case, the bond ---- is in particular a single bond.

The groups of the formula

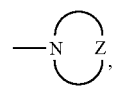

also referred to hereinafter as NZ, are a saturated or monounsaturated, mono- or bicyclic nitrogen heterocycle which optionally comprises a further heteroatom which is selected from nitrogen, oxygen and sulfur as a ring member. In the case of the bicyclic groups NZ, the two rings forming the bicyclic system are typically each independently 4-, 5-, 6- or 7-membered, the total number of ring members being in the range from 7 to 12. The NZ group may have an $R^a$ group or a fused-on benzene ring which may in turn be substituted in the manner described above. In addition, NZ may be a one, two, three or four further $C_1$-$C_4$-alkyl groups, in particular methyl groups.

Examples of suitable NZ groups are the mono- and bicyclic radicals NZ-1 to NZ-24 specified below.

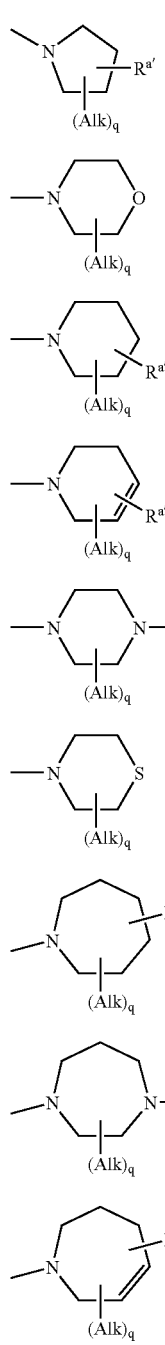

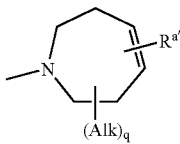
NZ-10

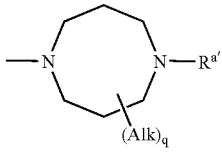
NZ-11

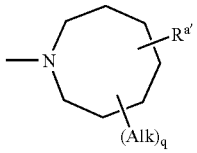
NZ-12

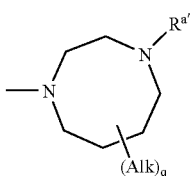
NZ-13

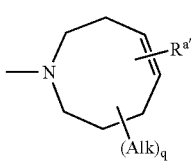
NZ-14

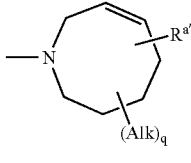
NZ-15

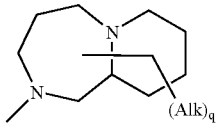
NZ-16

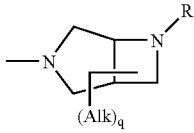
NZ-17

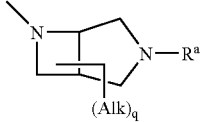
NZ-18

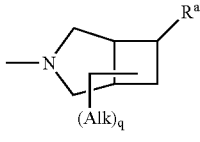
NZ-19

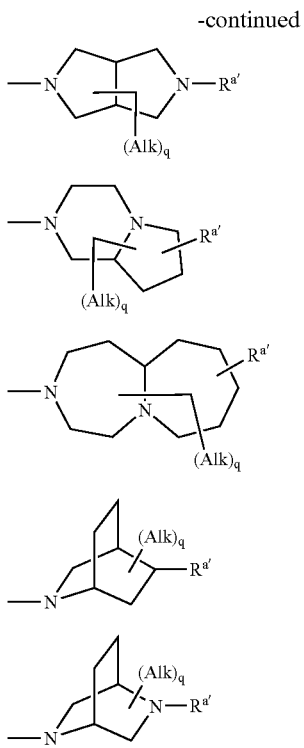

In the NZ-1 to NZ-24 radicals, $R^{a'}$ is hydrogen or is as defined above for $R^a$. The variable q is 0, 1, 2, 3 or 4, in particular 0 or 1, and Alk is an alkyl group having from 1 to 4 carbon atoms. Among the NZ radicals, preference is given to monocyclic radicals.

When $R^{a'}$ is an $R^a$ radical other than hydrogen, $R^a$ in the radicals NZ-3 to NZ-5 and NZ-7 to NZ-15 is arranged in the 4- or in the 5-position based on the nitrogen atom which is bonded to D. In the bicyclic radicals NZ-16 to NZ-24, when q≠0, Alk may be arranged on one or both of the rings.

With regard to the use of the inventive compounds for modulating the dopamine $D_3$ receptor, preference is given to those compounds where NZ has an $R^a$ group, and among these in particular monocyclic NZ radicals which have an $R^a$ group.

With regard to the use of the inventive compounds as dopamine $D_3$ receptor ligands, particular preference is given to those compounds I where the NZ group, as an $R^a$ radical, has an E-Ar radical and in particular a $(CH_2)_p$—Ar radical. In these, Ar and E are each as defined above, and p is 0, 1, 2, 3 or 4 and in particular 0 or 1.

Among the inventive compounds I and I' in which the NZ group has, as the $R^a$ radical, a group of the formula $(CH_2)_p$—Ar, preference is given in particular to those compounds where p=0 and Ar is phenyl, pyridyl, pyrimidinyl or s-triazinyl, which have 1, 2 or 3 of the aforementioned $R^b$ radicals. In particular, Ar is then a radical of the formula Ar-1

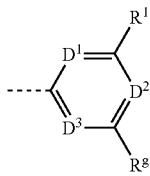

Ar-1 where the variables $D^1$ to $D^3$ are each independently N, CH or C—$R^b$. In this, Rb has one of the definitions specified above. $R^f$ and $R^g$ are each independently hydrogen or have one of the definitions specified for $R^b$.

In a first preferred embodiment of the invention, at least one of the variables $D^1$ to $D^3$ in formula Ar-1 is N and the remaining variables are each CH, where one of the variables $D^1$ to $D^3$ may also be C—$R^b$ when one of the variables $R^f$ is hydrogen. Among these, preference is given to compounds I and I' where $D^1$, and especially $D^1$ and $D^2$, are nitrogen and the remaining variables are each CH. In this embodiment, $R^f$ and $R^g$ are preferably each independently the following groups: hydrogen, $OR^1$, $NR^2R^3$, CN, $C_1$-$C_6$-alkyl which is optionally substituted by OH, $C_1$-$C_4$-alkoxy, halogen or phenyl, $C_2$-$C_6$-alkenyl, $C_2$-$C_6$-alkynyl, $C_3$-$C_6$-cycloalkyl, $C_4$-$C_{10}$-bicycloalkyl, $C_6$-$C_{10}$-tricycloalkyl, where the last three groups may optionally be substituted by halogen or $C_1$-$C_4$-alkyl, halogen, CN, $OR^1$, 5- or 6-membered heterocyclyl having 1, 2 or 3 heteroatoms selected from O, S and N, and phenyl, where phenyl and heterocyclyl optionally bear one or two substituents which are each independently selected from $C_1$-$C_4$-alkyl, $C_1$-$C_4$-alkoxy, $NR^2R^3$, CN, $C_1$-$C_2$-fluoroalkyl and halogen. $R^x$ is preferably different from hydrogen. In particular, both $R^f$ and $R^g$ are different from hydrogen. In particular, $R^f$ is $C_1$-$C_6$-alkyl, more preferably branched $C_3$-$C_6$-alkyl and especially tert-butyl. $R^g$ is is preferably selected from $C_1$-$C_4$-alkyl, $C_3$-$C_6$-cycloalkyl and $C_1$-$C_2$-fluoroalkyl. More preferably, $R^f$ and $R^g$ both have the definitions specified as preferred.

In another embodiment of the invention, all variables $D^1$ to $D^3$ in Ar-1 are CH or a C—$R^b$ group. In this embodiment, $R^f$, $R^g$ and $R^b$ are each preferably selected from hydrogen, $OR^1$, $NR^2R^3$, CN, $C_1$-$C_6$-alkyl which is optionally substituted by OH, $C_1$-$C_4$-alkoxy, halogen or phenyl, $C_2$-$C_6$-alkenyl, $C_2$-$C_6$-alkynyl, $C_3$-$C_6$-cycloalkyl, $C_4$-$C_{10}$-bicycloalkyl, $C_6$-$C_{10}$-tricycloalkyl, where the last three groups may optionally be substituted by halogen or $C_1$-$C_4$-alkyl, halogen, CN, $OR^1$, 5- or 6-membered heterocyclyl having 1, 2 or 3 heteroatoms selected from O, S and N, and phenyl, where phenyl and heterocyclyl optionally bear one or two substituents which are each independently selected from $C_1$-$C_4$-alkyl, $C_1$-$C_4$-alkoxy, $NR^2R^3$, CN, $C_1$-$C_2$-fluoroalkyl and halogen. In that case, Ar-1 more preferably has at least one substituent other than hydrogen. In this case, preferred substituents other than hydrogen are selected from halogen, especially chlorine or fluorine, $C_1$-$C_4$-alkyl, $C_1$-$C_4$-alkoxy, $C_1$-$C_4$-alkoxy-$C_1$-$C_4$-alkyl, $C_1$-$C_4$-haloalkyl, $C_1$-$C_4$-haloalkoxy and CN. In a particularly preferred embodiment, Ar-1 is then 2,3-dichlorophenyl.

Among the inventive compounds I and I', in which the NZ group has an $R^a$ radical of the formula $(CH_2)_p$—Ar, preference is further given to those compounds where p=1 and Ar is as defined above. In particular, Ar is phenyl, naphthyl, pyridyl, pyridinyl, pyrazinyl, pyridazinyl, thienyl, furyl, pyrrolyl, pyrazolyl, imidazolyl, oxazolyl, isoxazolyl, thiazolyl, isothiazolyl, 1-oxa-3,4-diazolyl or 1-thia-3,4-diazolyl, which are unsubstituted or may have 1, 2 or 3 of the abovementioned $R^b$ radicals. In that case, Ar is especially phenyl, pyridyl, thiadiazolyl, thienyl or imidazolyl, which may have 1, 2 or 3 of the abovementioned $R^b$ radicals. In that case, preferred $R^b$ radicals are in particular halogen, especially chlorine or fluorine, nitro, cyano, $C_1$-$C_4$-alkyl, $C_1$-$C_4$-alkoxy, $C_1$-$C_4$-haloalkyl and/or $C_1$-$C_4$-haloalkoxy.

In the compounds I in which NZ bears a radical of the formula E-Ar, Ar, when it is phenyl, or a heteroaromatic radical, may also be fused with an aromatic or heteroaromatic 5- or 6-membered cyclic system of the type mentioned above, for example with a 5- or 6-membered aromatic or nonaromatic heterocycle which has 1, 2 or 3 heteroatoms selected from O, N and S, for example with pyridine, pyrimidine, pyrazine, pyridazine, furan, thiophene, oxazole, isoxazole, thiazole, isothiazole, 1,4-dioxane, 1,4-oxazinane or 1,3-dioxolane, such as in quinoline, isoquinoline, 4H-quinolizine, 1,5-, 1,6-, 1,7-, 1,8-, 2,6- or 2,7-naphthyridine, indole, indolizine, 1- or 2-benzofuran, 1- or 2-benzothiophene, 1,3-benzoxazole, benzo[1,2-b and 1,2-c]oxazole, 1,3-benzothiazole, 1,3-benzimidazole, benzo[1,2-b and 1,2-c]isothiazole, quinazoline, chromene, chroman, 1,4-benzopiperazine, 1- or 2-benzopiperidine, benzo[1,4-b]oxazinane, benzo[1,3-b]dioxolane or benzo[1,4-b]dioxane. Phenyl and the aromatic heterocycles, especially phenyl and pyridyl, may also be fused with a 5 or 6-membered carbocycle, for example with benzene, cyclohex(adi)ene, cylopent(adi)ene, such as in naphthalene, indane, indene, quinoline, isoquinoline, di- or tetrahydronaphthalene. In such radicals, the bonding of Ar is via the phenyl, pyridyl or pyrimidinyl moiety of the bicyclic radical.

Preference is likewise given to $R^a$ groups which are selected from nonaromatic hydrocarbon radicals having from 1 to 14 carbon atoms, in particular $C_1$-$C_{10}$-alkyl, $C_2$-$C_{10}$-alkenyl, $C_3$-$C_{10}$-cycloalkyl, $C_3$-$C_{10}$-cycloalkyl-$C_1$-$C_4$-alkyl, $C_3$-$C_{10}$-cycloalkylcarbonyl-$C_1$-$C_4$-alkyl, $C_3$-$C_{10}$-heterocycloalkyl-$C_1$-$C_4$-alkyl and $C_3$-$C_{10}$-heterocycloalkylcarbonyl-$C_1$-$C_4$-alkyl. $C_3$-$C_{10}$-Cycloalkyl is then in particular cyclopropyl, cyclobutyl, cyclopentyl or cyclohexyl. The same applies to the $C_3$-$C_{10}$-cycloalkyl-$C_1$-$C_4$-alkyl and $C_3$-$C_{10}$-cycloalkylcarbonyl-$C_1$-$C_4$-alkyl radicals. $C_3$-$C_{10}$-Heterocycloalkyl is then in particular tetrahydrofuranyl, tetrahydrothienyl, pyrrolidinyl, piperidinyl or morpholinyl. The same applies to the $C_3$-$C_{10}$-heterocycloalkyl-$C_1$-$C_4$-alkyl and $C_3$-$C_{10}$-heterocycloalkylcarbonyl-$C_1$-$C_4$-alkyl radicals. In this embodiment, particular preference is given to compounds where $R^a$ is $C_1$-$C_4$-alkyl.

In particular, the NZ radicals obey the formula:

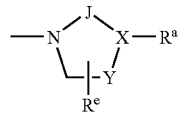

where $R^a$ is as defined above and in particular as defined above with preference;

J is $CH_2$, $CH_2$—$CH_2$ or $CH_2$—$CH_2$—$CH_2$, and in particular $CH_2$—$CH_2$;

X is CH or N and

Y is $CH_2$, $CH_2$—$CH_2$ or $CH_2$—$CH_2$—$CH_2$, or Y—X together are CH=C or $CH_2$—CH=C, preference being given to those radicals where X is N;

$R^e$ is hydrogen or $C_1$-$C_4$-alkyl and in particular hydrogen.

Examples of such radicals are the aforementioned NZ-1, NZ-3 to NZ-15 radicals, among which particular preference is given to the NZ-3, NZ-4 and NZ-5 radicals. Most preferably, NZ is the NZ-5 radical.

In a first preferred embodiment of the invention, NZ is a radical of the formula NZ-A

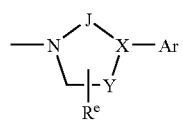

(NZ-A)

where J, X, Y, $R^e$ and Ar are each as defined above and in particular as defined above with preference, and Ar is in particular Ar-1.

In a second preferred embodiment of the invention, NZ is a radical of the formula NZ-B

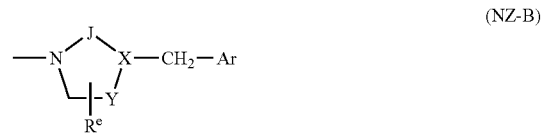

(NZ-B)

where J, X, Y, $R^e$ and Ar are each as defined above and in particular as defined above with preference. In particular, Ar is phenyl, naphthyl, pyridyl, pyridinyl, pyrazinyl, pyridazinyl, thienyl, furyl, pyrrolyl, pyrazolyl, imidazolyl, oxazolyl, isoxazolyl, thiazolyl, isothiazolyl, 1-oxa-3,4-diazolyl or 1-thia-3,4-diazolyl, which are unsubstituted or may have 1, 2 or 3 of the abovementioned $R^b$ radicals. Ar is then especially phenyl, pyridyl, thienyl or imidazolyl, which may have 1, 2 or 3 of the abovementioned $R^b$ radicals. Preferred $R^b$ are then in particular halogen, especially chlorine or fluorine, nitro, cyano, $C_1$-$C_4$-alkyl, $C_1$-$C_4$-alkoxy, $C_1$-$C_4$-haloalkyl and/or $C_1$-$C_4$-haloalkoxy.

In a further preferred embodiment of the invention, NZ is a radical of the formula NZ-C

(NZ-C)

where $R^e$, J, X and Y are each as defined above and $R^{aa}$ is a nonaromatic hydrocarbon radical having from 1 to 14 carbon atoms, in particular $C_1$-$C_{10}$-alkyl, $C_2$-$C_{10}$-alkenyl, $C_3$-$C_{10}$-cycloalkyl, $C_3$-$C_{10}$-cycloalkyl-$C_1$-$C_4$-alkyl, $C_3$-$C_{10}$-cycloalkylcarbonyl-$C_1$-$C_4$-alkyl, $C_3$-$C_{10}$-heterocycloalkyl-$C_1$-$C_4$-alkyl or $C_3$-$C_{10}$-heterocycloalkylcarbonyl-$C_1$-$C_4$-alkyl. $C_3$-$C_{10}$-Cycloalkyl is then in particular cyclopropyl, cyclobutyl, cyclopentyl or cyclohexyl. The same applies to the $C_3$-$C_{10}$-cycloalkyl-$C_1$-$C_4$-alkyl and $C_3$-$C_{10}$-cycloalkylcarbonyl-$C_1$-$C_4$-alkyl radicals. $C_3$-$C_{10}$-Heterocycloalkyl is then in particular tetrahydrofuranyl, tetrahydrothienyl, pyrrolidinyl, piperidinyl or morpholinyl. The same applies to the $C_3$-$C_{10}$-heterocycloalkyl-$C_1$-$C_4$-alkyl and $C_3$-$C_{10}$-heterocycloalkylcarbonyl-$C_1$-$C_4$-alkyl radicals. In this embodiment, particular preference is given to compounds where $R^a$ is $C_1$-$C_4$-alkyl.

In a further embodiment of the invention, the NZ group bears a fused-on benzene ring of the formula

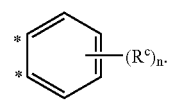

In this formula, n is preferably 1 or 2. $R^a$ is preferably as defined for $R^b$ and is in particular $C_1$-$C_4$-alkyl, $C_1$-$C_4$-alkoxy, CN, $OR^1$, $NR^2R^3$, $NO_2$, $SR^4$, $SO_2R^4$, $SO_2NR^2R^3$, $COOR^5$, COR$^6$, C$_1$-C$_2$-fluoroalkyl and halogen and especially C$_1$-C$_4$-alkyl, C$_1$-C$_4$-alkoxy, CN, COR$^6$, C$_1$-C$_2$-fluoroalkyl and halogen.

In particular, the NZ group is then a radical of the formula NZ-D

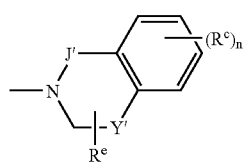

(NZ-D)

where n and R$^e$ are each as defined above,

J' is CH$_2$ or CH$_2$—CH$_2$;

Y' is a bond or CH$_2$ and

R$^e$ is hydrogen or C$_1$-C$_4$-alkyl.

In the compounds of the formula I, the group of the formula

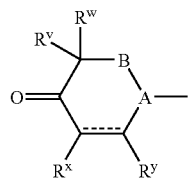

is preferably one of the A or B groups specified below:

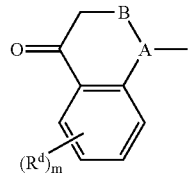

(A)

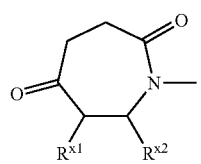

(B)

In formula A, the variables A and B are each as defined above, in particular as defined above with preference. In particular, the variable A in formula A is N—C(O), where the carbon atom is bonded to the variable B. B in formula A is in particular CH$_2$. The variable m is 0, 1, 2 or 3, in particular 0 or 1. R$^d$ is independently C$_1$-C$_4$-alkyl, C$_1$-C$_4$-hydroxyalkyl, C$_1$-C$_4$-alkoxy-C$_1$-C$_4$-alkyl, CN, OR$^1$, NR$^2$R$^3$, NO$_2$, SR$^4$, SO$_2$R$^4$, SO$_2$NR$^2$R$^3$, CONR$^2$R$^3$, COOR$^5$, COR$^6$, C$_1$-C$_2$-fluoroalkyl, C$_1$-C$_2$-fluoroalkoxy, C$_2$-C$_6$-alkenyl, C$_2$-C$_5$-alkynyl, C$_2$-C$_6$-alkenyloxy, C$_2$-C$_6$-alkynyloxy, C$_3$-C$_6$-cycloalkyl, C$_3$-C$_6$-cycloalkyl or halogen, and is in particular selected from C$_1$-C$_4$-alkyl, C$_1$-C$_4$-alkoxy, C$_1$-C$_2$-fluoroalkyl and halogen. Compounds of the general formula I or their tautomers I' which have an A group are also referred to hereinafter as compounds I-A or I-A'.

In Formula B, R$^{x1}$ and R$^{y1}$ are each independently hydrogen, halogen, optionally substituted C$_1$-C$_6$-alkyl, C$_1$-C$_6$-alkoxy, C$_2$-C$_6$-alkenyl, C$_2$-C$_6$-alkynyl, C$_3$-C$_6$-cycloalkyloxy, C$_3$-C$_6$-cycloalkyl-C$_1$-C$_4$-alkyloxy or C$_3$-C$_6$-cycloalkyl, and in particular hydrogen or alkyl. Compounds of the general formula I or their tautomers I' which have a B group are also referred to hereinafter as compounds I-B or I-B'.

Among the groups of the formulae A, mention should be made in particular of the A1, A2 and A3 groups:

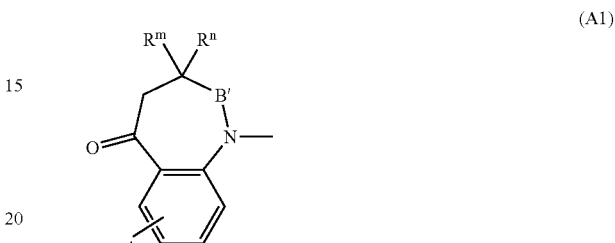

(A1)

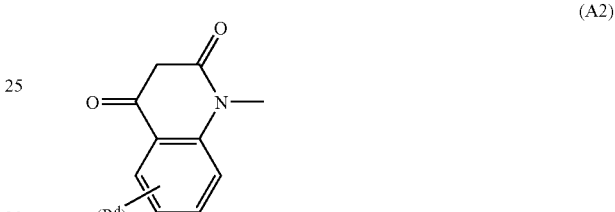

(A2)

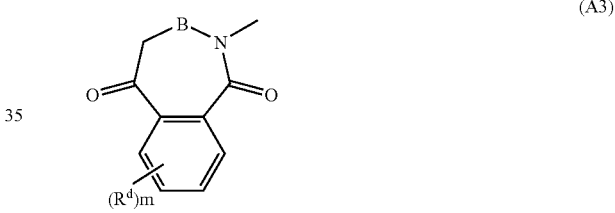

(A3)

In the formulae A1, A2 and A3, the variables m and R$^d$ are each as defined above, in particular as defined above with preference. In formula A1, R$^m$ and R$^n$ are each as defined above and in particular as defined above with preference. In particular, at least one of the R$^m$ or R$^n$ radicals and especially both R$^m$ and R$^n$ radicals are hydrogen. B' is CR$^p$R$^q$ or CO, where R$^p$ and R$^q$ are each as defined above and in particular as defined above with preference. In particular, B' is CO. In formula A3, B is as defined above and is in particular CO or CH$_2$. Among the compounds IA or the tautomers IA', preference is given in particular to those compounds which have, as the A group, a group of the formula A1 or A2.

Among the compounds of the formula IA, a preferred embodiment relates to compounds of the formula I-Aa defined below and its tautomers I-Aa':

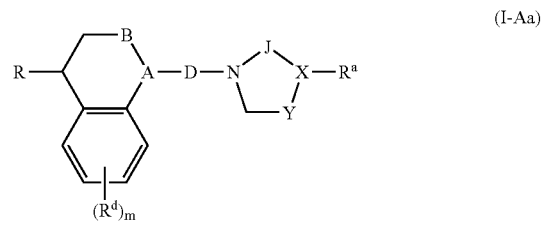

(I-Aa)

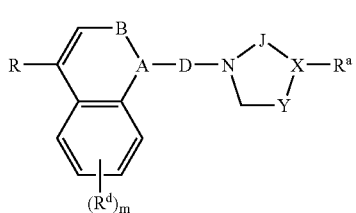

(I-Aa')

In the formulae I-Aa and I-Aa', A, B, D, m, J, X, Y, R, $R^a$ and $R^d$ are each as defined above and in particular as defined above with preference.

In particular, J in the formulae I-Aa and I-Aa' is $CH_2$—$CH_2$. The variable X in the formulae I-Aa and I-Aa' is in particular N, and Y is in particular $CH_2$.

Among the compounds I-Aa and I-Aa', particular preference is given to those where D is a $(CH_2)_k$ or a $C(O)(CH_2)_l$ group, where and l are each as defined above, where k is in particular 4, 5 or 6 and l is in particular 3, 4 or 5.

Among the compounds I-Aa and I-Aa', particular preference is given to those where A is N—C(O), where the carbon atom is bonded to the variable B.

Among the compounds I-Aa and I-Aa', particular preference is given to those where B is $CH_2$.

Among the compounds I-Aa and I-Aa', particular preference is given to those where $R^a$ is an E-A group and in particular $(CH_2)_p$—Ar, where E, p and Ar are each as defined above, where, in particular, p=0 or 1.

When p=0, Ar is in particular as defined in connection with the NZ-A group. When p=1, Ar is in particular as defined in connection with the NZ-B group. Among the compounds pounds I-Aa and I-Aa', preference is further given to those where $R^a$ is a nonaromatic hydrocarbon radical having from 1 to 14 carbon atoms. $R^a$ is then in particular as defined for $R^{aa}$ in the NZ-C group.

Among the compounds of the formula I-B, a preferred embodiment relates to compounds of the formula I-Ba defined below and its tautomers:

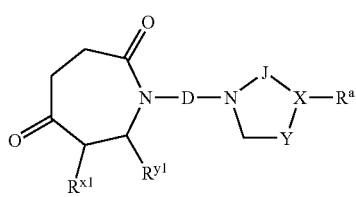

(I-Ba)

In formula I-Ba, A, B, D, m, J, X, Y, R, $R^a$, $R^{x1}$ and $R^{y1}$ are each as defined above and in particular as defined above with preference.

In particular, J in formula I-Ba is $CH_2$—$CH_2$. The variable X in the formulae I-Aa and I-Aa' is in particular N, and Y is in particular $CH_2$.

Among the compounds I-Ba, particular preference is given to those where D is a $(CH_2)_k$ group or a $C(O)(CH_2)_l$, where and l are each as defined above, where k is in particular 4, 5 or 6 and l is in particular 3, 4 or 5.

Among the compounds I-Ba, particular preference is given to those where $R^a$ is an E-A group and in particular $(CH_2)_p$—Ar, where E, p and Ar are each as defined above, where, in particular, p=0 or 1.

When p=0, Ar is in particular as defined in connection with the NZ-A group. When p=1, Ar is in particular as defined in connection with the NZ-B group. Among the compounds I-Aa and I-Aa', preference is further given to those where $R^a$ is a nonaromatic hydrocarbon radical having from 1 to 14 carbon atoms. $R^a$ is then in particular as defined for $R^{aa}$ in the NZ-C group.

Among the compounds of the formula I where NZ is a group of formula NZ-D, preference is given in particular to the compounds of the formula I-Ab and the tautomers I-Ab' defined below:

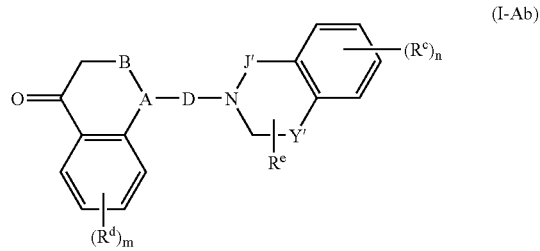

(I-Ab)

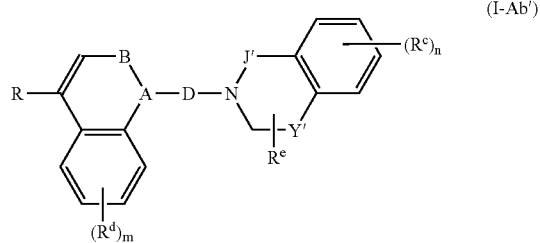

(I-Ab')

In the formulae I-Ab and I-Ab', A, B, D, J', Y', R, $R^c$, $R^e$ and n are each as defined above and in particular as defined above with preference.

The variable n is 0, 1, 2 or 3, in particular 0 or 1 and especially 0. $R^d$ are each independently $C_1$-$C_4$-alkyl, $C_1$-$C_4$-hydroxyalkyl, $C_1$-$C_4$-alkoxy-$C_1$-$C_4$-alkyl, CN, $OR^1$, $NR^2R^3$, $NO_2$, $SR^4$, $SO_2R^4$, $SO_2NR^2R^3$, $CONR^2R^3$, $COOR^5$, $COR^6$, $C_1$-$C_2$-fluoroalkyl, $C_1$-$C_2$-fluoroalkoxy, $C_2$-$C_6$-alkenyl, $C_2$-$C_6$-alkynyl, $C_2$-$C_6$-alkenyloxy, $C_2$-$C_6$-alkynyloxy, $C_3$-$C_6$-cycloalkyl, $C_3$-$C_6$-cycloalkyl or halogen, and is in particular selected from $C_1$-$C_4$-alkyl, $C_1$-$C_4$-alkoxy, $C_1$-$C_2$-fluoroalkyl and halogen.

In particular, J' in the formulae I-Ab and I-Ab' is $CH_2$. Y' is in particular $CH_2$.

Among the compounds I-Ab and I-Ab', particular preference is given to those where D is a $(CH_2)_k$ group or a $C(O)(CH_2)_l$ group, where and l are each as defined above, where k is in particular 4, 5 or 6 and l is in particular 3, 4 or 5.

Among the compounds I-Ab and I-Ab', particular preference is given to those where A is N—C(O), in which the carbon atom is bonded to the variable B.

Among the compounds I-Ab and I-Ab', particular preference is given to those where B is $CH_2$.

Among the compounds of the formula I where NZ is a group of the formula NZ-D, preference is also given to the compounds of the formula I-Bb defined below and its tautomers:

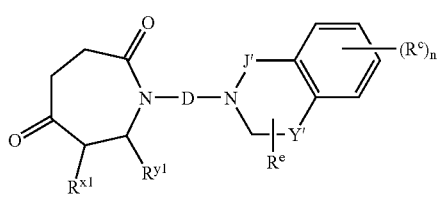

(I-Bb)

In formula I-Bb, n, D, J', Y', $R^c$, $R^e$, $R^{x1}$ and $R^{y1}$ are each as defined above and in particular as defined above with preference.

The variable n is 0, 1, 2 or 3, in particular 0 or 1 and especially 0. $R^d$ are each independently $C_1$-$C_4$-alkyl, $C_1$-$C_4$-hydroxyalkyl, $C_1$-$C_4$-alkoxy-$C_1$-$C_4$-alkyl, CN, $OR^1$, $NR^2R^3$, $NO_2$, $SR^4$, $SO_2R^4$, $SO_2NR^2R^3$, $CONR^2R^3$, $COOR^5$, $COR^6$, $C_1$-$C_2$-fluoroalkyl, $C_1$-$C_2$-fluoroalkoxy, $C_2$-$C_6$-alkenyl, $C_2$-$C_6$-alkynyl, $C_2$-$C_6$-alkenyloxy, $C_2$-$C_6$-alkynyloxy, $C_3$-$C_6$-cycloalkyl, $C_3$-$C_6$-cycloalkyl or halogen, and is in particular selected from $C_1$-$C_4$-alkyl, $C_1$-$C_4$-alkoxy, $C_1$-$C_2$-fluoroalkyl and halogen.

In particular, J' in formula I-Bb is $CH_2$. Y' is in particular $CH_2$.

Among the compounds I-Bb, particular preference is given to those where D is a $(CH_2)_k$ group or a $C(O)(CH_2)_l$ group, where k and l are each as defined above, where k is in particular 4, 5 or 6 and l is in particular 3, 4 or 5.

In substituents $OR^1$, $OR^{11}$ and $OR^{21}$, $R^1$, $R^{11}$ and $R^{21}$ are frequently H, $C_1$-$C_4$-alkyl, $CF_3$, $CHF_2$ or phenyl. Especially preferably, $OR^1$, $OR^{11}$ and $OR^{21}$ are each methoxy, trifluoromethoxy or phenoxy.

In substituents $CONR^2R^3$ (and analogously in $CONR^{12}R^{13}$ and $CONR^{22}R^{23}$), $R^2$ is preferably H or $C_1$-$C_4$-alkyl, and $R^3$ is preferably H, $C_1$-$C_4$-alkyl or $COR^7$. Especially preferably, $CONR^2R^3$, $CONR^{12}R^{13}$ and $CONR^{22}R^{23}$ are each $CONH_2$, $CONHCH_3$, $CON(CH_3)_2$ or $CONHCOCH_3$.

In substituents $NR^2R^3$ (and analogously in $NR^{12}R^{13}$ and $NR^{22}R^{23}$), $R^2$ is preferably H, $C_1$-$C_4$-alkyl or phenyl-substituted $C_1$-$C_4$-alkyl, and $R^3$ is H, $C_1$-$C_4$-alkyl or $COR^7$. Especially preferably, $NR^2R^3$, $NR^{12}R^{13}$ and $NR^{22}R^{23}$ are each $NH_2$, $NHCH_3$, $N(CH_3)_2$, NH-benzyl or $NHCOCH_3$.

In substituents $SO_2NR^2R^3$ (and analogously in $SO_2NR^{12}R^{13}$ and $SO_2NR^{22}R^{23}$), $R^2$ is preferably H or $C_1$-$C_4$-alkyl, and $R^3$ is preferably H, $C_1$-$C_4$-alkyl or $COR^7$. Especially preferably, $SO_2NR^2R^3$, $SO_2NR^{12}R^{13}$ and $SO_2NR^{22}R^{23}$ are each sulfamoyl.

When $R^2$, $R^3$ in the substituents $NR^2R^3$, $CONR^2R^3$, $SO_2NR^2R^3$ (analogously in $CONR^{12}R^{13}$, $CONR^{22}R^{23}$, $NR^{12}R^{13}$, $NR^{22}R^{23}$, $SO_2NR^{12}R^{13}$ and $SO_2NR^{22}R^{23}$), together with the nitrogen atom to which they are bonded, are a 5- or 6-membered, saturated or unsaturated N-heterocycle, the $NR^2R^3$, $NR^{12}R^{13}$ and $NR^{22}R^{23}$ groups in these radicals are, for example, N-pyrrolidinyl, N-piperidinyl, morpholin-1-yl or 4-methylpiperazin-1-yl.

In substituents $SR^4$, $SR^{14}$ and $SR^{24}$, $R^4$, $R^{14}$ and $R^{24}$ are preferably each $C_1$-$C_4$-alkyl. Especially preferably, $SR^4$ is thiomethyl.

In substituents $SO_2R^4$, $SO_2R^{14}$ and $SO_2R^{24}$, $R^4$, $R^{14}$ and $R^{24}$ are preferably each $C_1$-$C_4$-alkyl, $C_1$-$C_4$-haloalkyl or phenyl which optionally has a $C_1$-$C_4$-alkyl group as substituent. Especially preferably, $SO_2R^4$, $SO_2R^{14}$ and $SO_2R^{24}$ are each methylsulfonyl.

In substituents $COOR^5$, $COOR^{15}$ and $COOR^{25}$, $R^5$, $R^{15}$ and $R^{25}$ are frequently H or $C_1$-$C_4$-alkyl. Especially preferably, $COOR^5$, $COOR^{15}$ and $COOR^{25}$ are each $C_1$-$C_4$-alkoxycarbonyl, such as methoxycarbonyl, ethoxycarbonyl, n-propoxycarbonyl, i-propoxycarbonyl, n-butoxycarbonyl or t-butoxycarbonyl.

In substituents $COR^6$ (analogously in $COR^{16}$ and $COR^{26}$), $R^6$ is preferably H, $C_1$-$C_4$-alkyl or optionally substituted phenyl. Especially preferably, $COR^6$, $COR^{16}$ and $COR^{26}$ are each formyl, acetyl or benzoyl.

In substituents O—$COR^6$ (analogously in O—$COR^{16}$ and O—$COR^{26}$), $R^6$ is preferably H, $C_1$-$C_4$-alkyl or optionally substituted phenyl. Especially preferably, $OCOR^6$, O—$COR^{16}$ and O—$COR^{26}$ are each formyloxy, acetyloxy or benzoyloxy.

In substituents $COR^7$ (analogously in $COR^{17}$ and $COR^{27}$), $R^7$ is preferably H, $C_1$-$C_4$-alkyl or optionally substituted phenyl. Especially preferably, $COR^7$, $COR^{17}$ and $COR^{27}$ are each formyl, acetyl or benzoyl.

In the $NR^8$ group, $R^8$ is preferably hydrogen or methyl.

In substituents $COR^9$, $R^9$ is preferably H, $C_1$-$C_4$-alkyl or optionally substituted phenyl. Especially preferably, $COR^9$ is formyl, acetyl or benzoyl.

In the =N—$R^z$ group, $R^z$ is preferably OH, $C_1$-$C_4$-alkyl or $C_1$-$C_4$-alkoxy.

With regard to the use of the inventive compounds as dopamine $D_3$ receptor ligands, particular preference is given to the compounds IA and IB and in particular to the compounds IAa and IBa.

Very particular preference is given to the compounds of the formula I-Aa.a, where the variables D, E and Ar are each as defined above, in particular as defined above with preference. Examples of such compounds are the compounds I-Aa.a.1 to I-Aa.a.708, in which the variables D, E and Ar together are each as defined in one line of Table A.

TABLE A

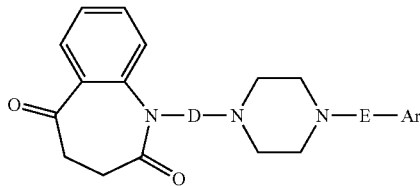
(I-Aa.a)

| | D | E | R$^a$ |
|---|---|---|---|
| A-1 | CH$_2$—CH$_2$—CH$_2$—CH$_2$ | — | 2-tert-butyl-4-trifluoromethylpyrimidin-6-yl |
| A-2 | CH$_2$—CH$_2$—CH$_2$—CH$_2$ | — | 2-tert-butyl-4-difluoromethylpyrimidin-6-yl |
| A-3 | CH$_2$—CH$_2$—CH$_2$—CH$_2$ | — | 2-tert-butyl-4-phenylpyrimidin-6-yl |
| A-4 | CH$_2$—CH$_2$—CH$_2$—CH$_2$ | — | 2-tert-butyl-4-methylpyrimidin-6-yl |
| A-5 | CH$_2$—CH$_2$—CH$_2$—CH$_2$ | — | 2-tert-butyl-4-ethylpyrimidin-6-yl |
| A-6 | CH$_2$—CH$_2$—CH$_2$—CH$_2$ | — | 2-tert-butyl-4-n-propylpyrimidin-6-yl |
| A-7 | CH$_2$—CH$_2$—CH$_2$—CH$_2$ | — | 2-tert-butyl-4-isopropylpyrimidin-6-yl |
| A-8 | CH$_2$—CH$_2$—CH$_2$—CH$_2$ | — | 2,4-bis(tert-butyl)pyrimidin-6-yl |
| A-9 | CH$_2$—CH$_2$—CH$_2$—CH$_2$ | — | 2-tert-butyl-4-cyclopropylpyrimidin-6-yl |
| A-10 | CH$_2$—CH$_2$—CH$_2$—CH$_2$ | — | 2-tert-butyl-4-cyclobutylpyrimidin-6-yl |
| A-11 | trans-CH$_2$—CH=CH—CH$_2$ | — | 2-tert-butyl-4-trifluoromethylpyrimidin-6-yl |
| A-12 | trans-CH$_2$—CH=CH—CH$_2$ | — | 2-tert-butyl-4-difluoromethylpyrimidin-6-yl |
| A-13 | trans-CH$_2$—CH=CH—CH$_2$ | — | 2-tert-butyl-4-phenylpyrimidin-6-yl |
| A-14 | trans-CH$_2$—CH=CH—CH$_2$ | — | 2-tert-butyl-4-methylpyrimidin-6-yl |
| A-15 | trans-CH$_2$—CH=CH—CH$_2$ | — | 2-tert-butyl-4-ethylpyrimidin-6-yl |
| A-16 | trans-CH$_2$—CH=CH—CH$_2$ | — | 2-tert-butyl-4-n-propylpyrimidin-6-yl |
| A-17 | trans-CH$_2$—CH=CH—CH$_2$ | — | 2-tert-butyl-4-isopropylpyrimidin-6-yl |
| A-18 | trans-CH$_2$—CH=CH—CH$_2$ | — | 2,4-bis(tert-butyl)pyrimidin-6-yl |
| A-19 | trans-CH$_2$—CH=CH—CH$_2$ | — | 2-tert-butyl-4-cyclopropylpyrimidin-6-yl |
| A-20 | trans-CH$_2$—CH=CH—CH$_2$ | — | 2-tert-butyl-4-cyclobutylpyrimidin-6-yl |
| A-21 | trans-CH$_2$—C(CH$_3$)=CH—CH$_2$ | — | 2-tert-butyl-4-trifluoromethylpyrimidin-6-yl |
| A-22 | trans-CH$_2$—C(CH$_3$)=CH—CH$_2$ | — | 2-tert-butyl-4-difluoromethylpyrimidin-6-yl |
| A-23 | trans-CH$_2$—C(CH$_3$)=CH—CH$_2$ | — | 2-tert-butyl-4-phenylpyrimidin-6-yl |
| A-24 | trans-CH$_2$—C(CH$_3$)=CH—CH$_2$ | — | 2-tert-butyl-4-methylpyrimidin-6-yl |
| A-25 | trans-CH$_2$—C(CH$_3$)=CH—CH$_2$ | — | 2-tert-butyl-4-ethylpyrimidin-6-yl |
| A-26 | trans-CH$_2$—C(CH$_3$)=CH—CH$_2$ | — | 2-tert-butyl-4-n-propylpyrimidin-6-yl |
| A-27 | trans-CH$_2$—C(CH$_3$)=CH—CH$_2$ | — | 2-tert-butyl-4-isopropylpyrimidin-6-yl |
| A-28 | trans-CH$_2$—C(CH$_3$)=CH—CH$_2$ | — | 2,4-bis(tert-butyl)pyrimidin-6-yl |
| A-29 | trans-CH$_2$—C(CH$_3$)=CH—CH$_2$ | — | 2-tert-butyl-4-cyclopropylpyrimidin-6-yl |
| A-30 | trans-CH$_2$—C(CH$_3$)=CH—CH$_2$ | — | 2-tert-butyl-4-cyclobutylpyrimidin-6-yl |
| A-31 | CH$_2$—CH(CH$_3$)—CH$_2$—CH$_2$ | — | 2-tert-butyl-4-trifluoromethylpyrimidin-6-yl |
| A-32 | CH$_2$—CH(CH$_3$)—CH$_2$—CH$_2$ | — | 2-tert-butyl-4-difluoromethylpyrimidin-6-yl |
| A-33 | CH$_2$—CH(CH$_3$)—CH$_2$—CH$_2$ | — | 2-tert-butyl-4-phenylpyrimidin-6-yl |
| A-34 | CH$_2$—CH(CH$_3$)—CH$_2$—CH$_2$ | — | 2-tert-butyl-4-methylpyrimidin-6-yl |
| A-35 | CH$_2$—CH(CH$_3$)—CH$_2$—CH$_2$ | — | 2-tert-butyl-4-ethylpyrimidin-6-yl |
| A-36 | CH$_2$—CH(CH$_3$)—CH$_2$—CH$_2$ | — | 2-tert-butyl-4-n-propylpyrimidin-6-yl |
| A-37 | CH$_2$—CH(CH$_3$)—CH$_2$—CH$_2$ | — | 2-tert-butyl-4-isopropylpyrimidin-6-yl |
| A-38 | CH$_2$—CH(CH$_3$)—CH$_2$—CH$_2$ | — | 2,4-bis(tert-butyl)pyrimidin-6-yl |
| A-39 | CH$_2$—CH(CH$_3$)—CH$_2$—CH$_2$ | — | 2-tert-butyl-4-cyclopropylpyrimidin-6-yl |
| A-40 | CH$_2$—CH(CH$_3$)—CH$_2$—CH$_2$ | — | 2-tert-butyl-4-cyclobutylpyrimidin-6-yl |
| A-41 | CH$_2$—CH$_2$—CH$_2$—CH(CH$_3$) | — | 2-tert-butyl-4-trifluoromethylpyrimidin-6-yl |
| A-42 | CH$_2$—CH$_2$—CH$_2$—CH(CH$_3$) | — | 2-tert-butyl-4-difluoromethylpyrimidin-6-yl |
| A-43 | CH$_2$—CH$_2$—CH$_2$—CH(CH$_3$) | — | 2-tert-butyl-4-phenylpyrimidin-6-yl |
| A-44 | CH$_2$—CH$_2$—CH$_2$—CH(CH$_3$) | — | 2-tert-butyl-4-methylpyrimidin-6-yl |
| A-45 | CH$_2$—CH$_2$—CH$_2$—CH(CH$_3$) | — | 2-tert-butyl-4-ethylpyrimidin-6-yl |
| A-46 | CH$_2$—CH$_2$—CH$_2$—CH(CH$_3$) | — | 2-tert-butyl-4-n-propylpyrimidin-6-yl |
| A-47 | CH$_2$—CH$_2$—CH$_2$—CH(CH$_3$) | — | 2-tert-butyl-4-isopropylpyrimidin-6-yl |
| A-48 | CH$_2$—CH$_2$—CH$_2$—CH(CH$_3$) | — | 2,4-bis(tert-butyl)pyrimidin-6-yl |
| A-49 | CH$_2$—CH$_2$—CH$_2$—CH(CH$_3$) | — | 2-tert-butyl-4-cyclopropylpyrimidin-6-yl |
| A-50 | CH$_2$—CH$_2$—CH$_2$—CH(CH$_3$) | — | 2-tert-butyl-4-cyclobutylpyrimidin-6-yl |
| A-51 | C(O)—CH$_2$—CH$_2$—CH$_2$ | — | 2-tert-butyl-4-trifluoromethylpyrimidin-6-yl |
| A-52 | C(O)—CH$_2$—CH$_2$—CH$_2$ | — | 2-tert-butyl-4-difluoromethylpyrimidin-6-yl |
| A-53 | C(O)—CH$_2$—CH$_2$—CH$_2$ | — | 2-tert-butyl-4-phenylpyrimidin-6-yl |
| A-54 | C(O)—CH$_2$—CH$_2$—CH$_2$ | — | 2-tert-butyl-4-methylpyrimidin-6-yl |
| A-55 | C(O)—CH$_2$—CH$_2$—CH$_2$ | — | 2-tert-butyl-4-ethylpyrimidin-6-yl |
| A-56 | C(O)—CH$_2$—CH$_2$—CH$_2$ | — | 2-tert-butyl-4-n-propylpyrimidin-6-yl |
| A-57 | C(O)—CH$_2$—CH$_2$—CH$_2$ | — | 2-tert-butyl-4-isopropylpyrimidin-6-yl |
| A-58 | C(O)—CH$_2$—CH$_2$—CH$_2$ | — | 2,4-bis(tert-butyl)pyrimidin-6-yl |
| A-59 | C(O)—CH$_2$—CH$_2$—CH$_2$ | — | 2-tert-butyl-4-cyclopropylpyrimidin-6-yl |
| A-60 | C(O)—CH$_2$—CH$_2$—CH$_2$ | — | 2-tert-butyl-4-cyclobutylpyrimidin-6-yl |
| A-61 | C(O)—CH$_2$—CH$_2$—CH$_2$—CH$_2$ | — | 2-tert-butyl-4-trifluoromethylpyrimidin-6-yl |
| A-62 | C(O)—CH$_2$—CH$_2$—CH$_2$—CH$_2$ | — | 2-tert-butyl-4-difluoromethylpyrimidin-6-yl |
| A-63 | C(O)—CH$_2$—CH$_2$—CH$_2$—CH$_2$ | — | 2-tert-butyl-4-phenylpyrimidin-6-yl |
| A-64 | C(O)—CH$_2$—CH$_2$—CH$_2$—CH$_2$ | — | 2-tert-butyl-4-methylpyrimidin-6-yl |
| A-65 | C(O)—CH$_2$—CH$_2$—CH$_2$—CH$_2$ | — | 2-tert-butyl-4-ethylpyrimidin-6-yl |
| A-66 | C(O)—CH$_2$—CH$_2$—CH$_2$—CH$_2$ | — | 2-tert-butyl-4-n-propylpyrimidin-6-yl |

TABLE A-continued (I-Aa.a)

| | D | E | R$^a$ |
|---|---|---|---|
| A-67 | C(O)—CH$_2$—CH$_2$—CH$_2$—CH$_2$ | — | 2-tert-butyl-4-isopropylpyrimidin-6-yl |
| A-68 | C(O)—CH$_2$—CH$_2$—CH$_2$—CH$_2$ | — | 2,4-bis(tert-butyl)pyrimidin-6-yl |
| A-69 | C(O)—CH$_2$—CH$_2$—CH$_2$—CH$_2$ | — | 2-tert-butyl-4-cyclopropylpyrimidin-6-yl |
| A-70 | C(O)—CH$_2$—CH$_2$—CH$_2$—CH$_2$ | — | 2-tert-butyl-4-cyclobutylpyrimidin-6-yl |
| A-71 | CH$_2$—CH$_2$—CH$_2$—CH$_2$ | — | 2-tert-butyl-4-trifluoromethylpyridin-6-yl |
| A-72 | CH$_2$—CH$_2$—CH$_2$—CH$_2$ | — | 2-tert-butyl-4-difluoromethylpyridin-6-yl |
| A-73 | CH$_2$—CH$_2$—CH$_2$—CH$_2$ | — | 2-tert-butyl-4-phenylpyridin-6-yl |
| A-74 | CH$_2$—CH$_2$—CH$_2$—CH$_2$ | — | 2-tert-butyl-4-methylpyridin-6-yl |
| A-75 | CH$_2$—CH$_2$—CH$_2$—CH$_2$ | — | 2-tert-butyl-4-ethylpyridin-6-yl |
| A-76 | CH$_2$—CH$_2$—CH$_2$—CH$_2$ | — | 2-tert-butyl-4-n-propylpyridin-6-yl |
| A-77 | CH$_2$—CH$_2$—CH$_2$—CH$_2$ | — | 2-tert-butyl-4-isopropylpyridin-6-yl |
| A-78 | CH$_2$—CH$_2$—CH$_2$—CH$_2$ | — | 2,4-bis(tert-butyl)pyridin-6-yl |
| A-79 | CH$_2$—CH$_2$—CH$_2$—CH$_2$ | — | 2-tert-butyl-4-cyclopropylpyridin-6-yl |
| A-80 | CH$_2$—CH$_2$—CH$_2$—CH$_2$ | — | 2-tert-butyl-4-cyclobutylpyridin-6-yl |
| A-81 | trans-CH$_2$—CH=CH—CH$_2$ | — | 2-tert-butyl-4-trifluoromethylpyridin-6-yl |
| A-82 | trans-CH$_2$—CH=CH—CH$_2$ | — | 2-tert-butyl-4-difluoromethylpyridin-6-yl |
| A-83 | trans-CH$_2$—CH=CH—CH$_2$ | — | 2-tert-butyl-4-phenylpyridin-6-yl |
| A-84 | trans-CH$_2$—CH=CH—CH$_2$ | — | 2-tert-butyl-4-methylpyridin-6-yl |
| A-85 | trans-CH$_2$—CH=CH—CH$_2$ | — | 2-tert-butyl-4-ethylpyridin-6-yl |
| A-86 | trans-CH$_2$—CH=CH—CH$_2$ | — | 2-tert-butyl-4-n-propylpyridin-6-yl |
| A-87 | trans-CH$_2$—CH=CH—CH$_2$ | — | 2-tert-butyl-4-isopropylpyridin-6-yl |
| A-88 | trans-CH$_2$—CH=CH—CH$_2$ | — | 2,4-bis(tert-butyl)pyridin-6-yl |
| A-89 | trans-CH$_2$—CH=CH—CH$_2$ | — | 2-tert-butyl-4-cyclopropylpyridin-6-yl |
| A-90 | trans-CH$_2$—CH=CH—CH$_2$ | — | 2-tert-butyl-4-cyclobutylpyridin-6-yl |
| A-91 | trans-CH$_2$—C(CH$_3$)=CH—CH$_2$ | — | 2-tert-butyl-4-trifluoromethylpyridin-6-yl |
| A-92 | trans-CH$_2$—C(CH$_3$)=CH—CH$_2$ | — | 2-tert-butyl-4-difluoromethylpyridin-6-yl |
| A-93 | trans-CH$_2$—C(CH$_3$)=CH—CH$_2$ | — | 2-tert-butyl-4-phenylpyridin-6-yl |
| A-94 | trans-CH$_2$—C(CH$_3$)=CH—CH$_2$ | — | 2-tert-butyl-4-methylpyridin-6-yl |
| A-95 | trans-CH$_2$—C(CH$_3$)=CH—CH$_2$ | — | 2-tert-butyl-4-ethylpyridin-6-yl |
| A-96 | trans-CH$_2$—C(CH$_3$)=CH—CH$_2$ | — | 2-tert-butyl-4-n-propylpyridin-6-yl |
| A-97 | trans-CH$_2$—C(CH$_3$)=CH—CH$_2$ | — | 2-tert-butyl-4-isopropylpyridin-6-yl |
| A-98 | trans-CH$_2$—C(CH$_3$)=CH—CH$_2$ | — | 2,4-bis(tert-butyl)pyridin-6-yl |
| A-99 | trans-CH$_2$—C(CH$_3$)=CH—CH$_2$ | — | 2-tert-butyl-4-cyclopropylpyridin-6-yl |
| A-100 | trans-CH$_2$—C(CH$_3$)=CH—CH$_2$ | — | 2-tert-butyl-4-cyclobutylpyridin-6-yl |
| A-101 | CH$_2$—CH(CH$_3$)—CH$_2$—CH$_2$ | — | 2-tert-butyl-4-trifluoromethylpyridin-6-yl |
| A-102 | CH$_2$—CH(CH$_3$)—CH$_2$—CH$_2$ | — | 2-tert-butyl-4-difluoromethylpyridin-6-yl |
| A-103 | CH$_2$—CH(CH$_3$)—CH$_2$—CH$_2$ | — | 2-tert-butyl-4-phenylpyridin-6-yl |
| A-104 | CH$_2$—CH(CH$_3$)—CH$_2$—CH$_2$ | — | 2-tert-butyl-4-methylpyridin-6-yl |
| A-105 | CH$_2$—CH(CH$_3$)—CH$_2$—CH$_2$ | — | 2-tert-butyl-4-ethylpyridin-6-yl |
| A-106 | CH$_2$—CH(CH$_3$)—CH$_2$—CH$_2$ | — | 2-tert-butyl-4-n-propylpyridin-6-yl |
| A-107 | CH$_2$—CH(CH$_3$)—CH$_2$—CH$_2$ | — | 2-tert-butyl-4-isopropylpyridin-6-yl |
| A-108 | CH$_2$—CH(CH$_3$)—CH$_2$—CH$_2$ | — | 2,4-bis(tert-butyl)pyridin-6-yl |
| A-109 | CH$_2$—CH(CH$_3$)—CH$_2$—CH$_2$ | — | 2-tert-butyl-4-cyclopropylpyridin-6-yl |
| A-110 | CH$_2$—CH(CH$_3$)—CH$_2$—CH$_2$ | — | 2-tert-butyl-4-cyclobutylpyridin-6-yl |
| A-111 | CH$_2$—CH$_2$—CH$_2$—CH(CH$_3$) | — | 2-tert-butyl-4-trifluoromethylpyridin-6-yl |
| A-112 | CH$_2$—CH$_2$—CH$_2$—CH(CH$_3$) | — | 2-tert-butyl-4-difluoromethylpyridin-6-yl |
| A-113 | CH$_2$—CH$_2$—CH$_2$—CH(CH$_3$) | — | 2-tert-butyl-4-phenylpyridin-6-yl |
| A-114 | CH$_2$—CH$_2$—CH$_2$—CH(CH$_3$) | — | 2-tert-butyl-4-methylpyridin-6-yl |
| A-115 | CH$_2$—CH$_2$—CH$_2$—CH(CH$_3$) | — | 2-tert-butyl-4-ethylpyridin-6-yl |
| A-116 | CH$_2$—CH$_2$—CH$_2$—CH(CH$_3$) | — | 2-tert-butyl-4-n-propylpyridin-6-yl |
| A-117 | CH$_2$—CH$_2$—CH$_2$—CH(CH$_3$) | — | 2-tert-butyl-4-isopropylpyridin-6-yl |
| A-118 | CH$_2$—CH$_2$—CH$_2$—CH(CH$_3$) | — | 2,4-bis(tert-butyl)pyridin-6-yl |
| A-119 | CH$_2$—CH$_2$—CH$_2$—CH(CH$_3$) | — | 2-tert-butyl-4-cyclopropylpyridin-6-yl |
| A-120 | CH$_2$—CH$_2$—CH$_2$—CH(CH$_3$) | — | 2-tert-butyl-4-cyclobutylpyridin-6-yl |
| A-121 | C(O)—CH$_2$—CH$_2$—CH$_2$ | — | 2-tert-butyl-4-trifluoromethylpyridin-6-yl |
| A-122 | C(O)—CH$_2$—CH$_2$—CH$_2$ | — | 2-tert-butyl-4-difluoromethylpyridin-6-yl |
| A-123 | C(O)—CH$_2$—CH$_2$—CH$_2$ | — | 2-tert-butyl-4-phenylpyridin-6-yl |
| A-124 | C(O)—CH$_2$—CH$_2$—CH$_2$ | — | 2-tert-butyl-4-methylpyridin-6-yl |
| A-125 | C(O)—CH$_2$—CH$_2$—CH$_2$ | — | 2-tert-butyl-4-ethylpyridin-6-yl |
| A-126 | C(O)—CH$_2$—CH$_2$—CH$_2$ | — | 2-tert-butyl-4-n-propylpyridin-6-yl |
| A-127 | C(O)—CH$_2$—CH$_2$—CH$_2$ | — | 2-tert-butyl-4-isopropylpyridin-6-yl |
| A-128 | C(O)—CH$_2$—CH$_2$—CH$_2$ | — | 2,4-bis(tert-butyl)pyridin-6-yl |
| A-129 | C(O)—CH$_2$—CH$_2$—CH$_2$ | — | 2-tert-butyl-4-cyclopropylpyridin-6-yl |
| A-130 | C(O)—CH$_2$—CH$_2$—CH$_2$ | — | 2-tert-butyl-4-cyclobutylpyridin-6-yl |
| A-131 | C(O)—CH$_2$—CH$_2$—CH$_2$—CH$_2$ | — | 2-tert-butyl-4-trifluoromethylpyridin-6-yl |
| A-132 | C(O)—CH$_2$—CH$_2$—CH$_2$—CH$_2$ | — | 2-tert-butyl-4-difluoromethylpyridin-6-yl |

TABLE A-continued (I-Aa.a)

Structure: benzo-fused 7-membered ring with two C=O groups and N–D–N(piperazine)N–E–Ar

| | D | E | Rª |
|---|---|---|---|
| A-133 | C(O)—CH₂—CH₂—CH₂—CH₂ | — | 2-tert-butyl-4-phenylpyridin-6-yl |
| A-134 | C(O)—CH₂—CH₂—CH₂—CH₂ | — | 2-tert-butyl-4-methylpyridin-6-yl |
| A-135 | C(O)—CH₂—CH₂—CH₂—CH₂ | — | 2-tert-butyl-4-ethylpyridin-6-yl |
| A-136 | C(O)—CH₂—CH₂—CH₂—CH₂ | — | 2-tert-butyl-4-n-propylpyridin-6-yl |
| A-137 | C(O)—CH₂—CH₂—CH₂—CH₂ | — | 2-tert-butyl-4-isopropylpyridin-6-yl |
| A-138 | C(O)—CH₂—CH₂—CH₂—CH₂ | — | 2,4-bis(tert-butyl)pyridin-6-yl |
| A-139 | C(O)—CH₂—CH₂—CH₂—CH₂ | — | 2-tert-butyl-4-cyclopropylpyridin-6-yl |
| A-140 | C(O)—CH₂—CH₂—CH₂—CH₂ | — | 2-tert-butyl-4-cyclobutylpyridin-6-yl |
| A-141 | CH₂—CH₂—CH₂—CH₂ | — | 2-tert-butyl-4-trifluoromethyltriazin-6-yl |
| A-142 | CH₂—CH₂—CH₂—CH₂ | — | 2-tert-butyl-4-difluoromethyltriazin-6-yl |
| A-143 | CH₂—CH₂—CH₂—CH₂ | — | 2-tert-butyl-4-phenyltriazin-6-yl |
| A-144 | CH₂—CH₂—CH₂—CH₂ | — | 2-tert-butyl-4-methyltriazin-6-yl |
| A-145 | CH₂—CH₂—CH₂—CH₂ | — | 2-tert-butyl-4-ethyltriazin-6-yl |
| A-146 | CH₂—CH₂—CH₂—CH₂ | — | 2-tert-butyl-4-n-propyltriazin-6-yl |
| A-147 | CH₂—CH₂—CH₂—CH₂ | — | 2-tert-butyl-4-isopropyltriazin-6-yl |
| A-148 | CH₂—CH₂—CH₂—CH₂ | — | 2,4-bis(tert-butyl)triazin-6-yl |
| A-149 | CH₂—CH₂—CH₂—CH₂ | — | 2-tert-butyl-4-cyclopropyltriazin-6-yl |
| A-150 | CH₂—CH₂—CH₂—CH₂ | — | 2-tert-butyl-4-cyclobutyltriazin-6-yl |
| A-151 | trans-CH₂—CH=CH—CH₂ | — | 2-tert-butyl-4-trifluoromethyltriazin-6-yl |
| A-152 | trans-CH₂—CH=CH—CH₂ | — | 2-tert-butyl-4-difluoromethyltriazin-6-yl |
| A-153 | trans-CH₂—CH=CH—CH₂ | — | 2-tert-butyl-4-phenyltriazin-6-yl |
| A-154 | trans-CH₂—CH=CH—CH₂ | — | 2-tert-butyl-4-methyltriazin-6-yl |
| A-155 | trans-CH₂—CH=CH—CH₂ | — | 2-tert-butyl-4-ethyltriazin-6-yl |
| A-156 | trans-CH₂—CH=CH—CH₂ | — | 2-tert-butyl-4-n-propyltriazin-6-yl |
| A-157 | trans-CH₂—CH=CH—CH₂ | — | 2-tert-butyl-4-isopropyltriazin-6-yl |
| A-158 | trans-CH₂—CH=CH—CH₂ | — | 2,4-bis(tert-butyl)triazin-6-yl |
| A-159 | trans-CH₂—CH=CH—CH₂ | — | 2-tert-butyl-4-cyclopropyltriazin-6-yl |
| A-160 | trans-CH₂—CH=CH—CH₂ | — | 2-tert-butyl-4-cyclobutyltriazin-6-yl |
| A-161 | trans-CH₂—C(CH₃)=CH—CH₂ | — | 2-tert-butyl-4-trifluoromethyltriazin-6-yl |
| A-162 | trans-CH₂—C(CH₃)=CH—CH₂ | — | 2-tert-butyl-4-difluoromethyltriazin-6-yl |
| A-163 | trans-CH₂—C(CH₃)=CH—CH₂ | — | 2-tert-butyl-4-phenyltriazin-6-yl |
| A-164 | trans-CH₂—C(CH₃)=CH—CH₂ | — | 2-tert-butyl-4-methyltriazin-6-yl |
| A-165 | trans-CH₂—C(CH₃)=CH—CH₂ | — | 2-tert-butyl-4-ethyltriazin-6-yl |
| A-166 | trans-CH₂—C(CH₃)=CH—CH₂ | — | 2-tert-butyl-4-n-propyltriazin-6-yl |
| A-167 | trans-CH₂—C(CH₃)=CH—CH₂ | — | 2-tert-butyl-4-isopropyltriazin-6-yl |
| A-168 | trans-CH₂—C(CH₃)=CH—CH₂ | — | 2,4-bis(tert-butyl)triazin-6-yl |
| A-169 | trans-CH₂—C(CH₃)=CH—CH₂ | — | 2-tert-butyl-4-cyclopropyltriazin-6-yl |
| A-170 | trans-CH₂—C(CH₃)=CH—CH₂ | — | 2-tert-butyl-4-cyclobutyltriazin-6-yl |
| A-171 | CH₂—CH(CH₃)—CH₂—CH₂ | — | 2-tert-butyl-4-trifluoromethyltriazin-6-yl |
| A-172 | CH₂—CH(CH₃)—CH₂—CH₂ | — | 2-tert-butyl-4-difluoromethyltriazin-6-yl |
| A-173 | CH₂—CH(CH₃)—CH₂—CH₂ | — | 2-tert-butyl-4-phenyltriazin-6-yl |
| A-174 | CH₂—CH(CH₃)—CH₂—CH₂ | — | 2-tert-butyl-4-methyltriazin-6-yl |
| A-175 | CH₂—CH(CH₃)—CH₂—CH₂ | — | 2-tert-butyl-4-ethyltriazin-6-yl |
| A-176 | CH₂—CH(CH₃)—CH₂—CH₂ | — | 2-tert-butyl-4-n-propyltriazin-6-yl |
| A-177 | CH₂—CH(CH₃)—CH₂—CH₂ | — | 2-tert-butyl-4-isopropyltriazin-6-yl |
| A-178 | CH₂—CH(CH₃)—CH₂—CH₂ | — | 2,4-bis(tert-butyl)triazin-6-yl |
| A-179 | CH₂—CH(CH₃)—CH₂—CH₂ | — | 2-tert-butyl-4-cyclopropyltriazin-6-yl |
| A-180 | CH₂—CH(CH₃)—CH₂—CH₂ | — | 2-tert-butyl-4-cyclobutyltriazin-6-yl |
| A-181 | CH₂—CH₂—CH₂—CH(CH₃) | — | 2-tert-butyl-4-trifluoromethyltriazin-6-yl |
| A-182 | CH₂—CH₂—CH₂—CH(CH₃) | — | 2-tert-butyl-4-difluoromethyltriazin-6-yl |
| A-183 | CH₂—CH₂—CH₂—CH(CH₃) | — | 2-tert-butyl-4-phenyltriazin-6-yl |
| A-184 | CH₂—CH₂—CH₂—CH(CH₃) | — | 2-tert-butyl-4-methyltriazin-6-yl |
| A-185 | CH₂—CH₂—CH₂—CH(CH₃) | — | 2-tert-butyl-4-ethyltriazin-6-yl |
| A-186 | CH₂—CH₂—CH₂—CH(CH₃) | — | 2-tert-butyl-4-n-propyltriazin-6-yl |
| A-187 | CH₂—CH₂—CH₂—CH(CH₃) | — | 2-tert-butyl-4-isopropyltriazin-6-yl |
| A-188 | CH₂—CH₂—CH₂—CH(CH₃) | — | 2,4-bis(tert-butyl)triazin-6-yl |
| A-189 | CH₂—CH₂—CH₂—CH(CH₃) | — | 2-tert-butyl-4-cyclopropyltriazin-6-yl |
| A-190 | CH₂—CH₂—CH₂—CH(CH₃) | — | 2-tert-butyl-4-cyclobutyltriazin-6-yl |
| A-191 | C(O)—CH₂—CH₂—CH₂ | — | 2-tert-butyl-4-trifluoromethyltriazin-6-yl |
| A-192 | C(O)—CH₂—CH₂—CH₂ | — | 2-tert-butyl-4-difluoromethyltriazin-6-yl |
| A-193 | C(O)—CH₂—CH₂—CH₂ | — | 2-tert-butyl-4-phenyltriazin-6-yl |
| A-194 | C(O)—CH₂—CH₂—CH₂ | — | 2-tert-butyl-4-methyltriazin-6-yl |
| A-195 | C(O)—CH₂—CH₂—CH₂ | — | 2-tert-butyl-4-ethyltriazin-6-yl |
| A-196 | C(O)—CH₂—CH₂—CH₂ | — | 2-tert-butyl-4-n-propyltriazin-6-yl |
| A-197 | C(O)—CH₂—CH₂—CH₂ | — | 2-tert-butyl-4-isopropyltriazin-6-yl |
| A-198 | C(O)—CH₂—CH₂—CH₂ | — | 2,4-bis(tert-butyl)triazin-6-yl |

TABLE A-continued

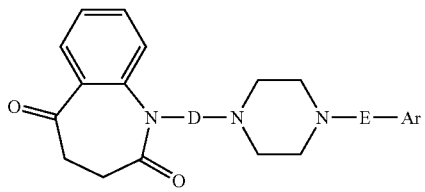

(I-Aa.a)

| | D | E | R$^a$ |
|---|---|---|---|
| A-199 | C(O)—CH$_2$—CH$_2$—CH$_2$ | — | 2-tert-butyl-4-cyclopropyltriazin-6-yl |
| A-200 | C(O)—CH$_2$—CH$_2$—CH$_2$ | — | 2-tert-butyl-4-cyclobutyltriazin-6-yl |
| A-201 | C(O)—CH$_2$—CH$_2$—CH$_2$—CH$_2$ | — | 2-tert-butyl-4-trifluoromethyltriazin-6-yl |
| A-202 | C(O)—CH$_2$—CH$_2$—CH$_2$—CH$_2$ | — | 2-tert-butyl-4-difluoromethyltriazin-6-yl |
| A-203 | C(O)—CH$_2$—CH$_2$—CH$_2$—CH$_2$ | — | 2-tert-butyl-4-phenyltriazin-6-yl |
| A-204 | C(O)—CH$_2$—CH$_2$—CH$_2$—CH$_2$ | — | 2-tert-butyl-4-methyltriazin-6-yl |
| A-205 | C(O)—CH$_2$—CH$_2$—CH$_2$—CH$_2$ | — | 2-tert-butyl-4-ethyltriazin-6-yl |
| A-206 | C(O)—CH$_2$—CH$_2$—CH$_2$—CH$_2$ | — | 2-tert-butyl-4-n-propyltriazin-6-yl |
| A-207 | C(O)—CH$_2$—CH$_2$—CH$_2$—CH$_2$ | — | 2-tert-butyl-4-isopropyltriazin-6-yl |
| A-208 | C(O)—CH$_2$—CH$_2$—CH$_2$—CH$_2$ | — | 2,4-bis(tert-butyl)triazin-6-yl |
| A-209 | C(O)—CH$_2$—CH$_2$—CH$_2$—CH$_2$ | — | 2-tert-butyl-4-cyclopropyltriazin-6-yl |
| A-210 | C(O)—CH$_2$—CH$_2$—CH$_2$—CH$_2$ | — | 2-tert-butyl-4-cyclobutyltriazin-6-yl |
| A-211 | CH$_2$—CH$_2$—CH$_2$—CH$_2$ | — | 4-tert-butyl-2-trifluoromethylpyridin-6-yl |
| A-212 | CH$_2$—CH$_2$—CH$_2$—CH$_2$ | — | 4-tert-butyl-2-difluoromethylpyridin-6-yl |
| A-213 | CH$_2$—CH$_2$—CH$_2$—CH$_2$ | — | 4-tert-butyl-2-phenylpyridin-6-yl |
| A-214 | CH$_2$—CH$_2$—CH$_2$—CH$_2$ | — | 4-tert-butyl-2-methylpyridin-6-yl |
| A-215 | CH$_2$—CH$_2$—CH$_2$—CH$_2$ | — | 4-tert-butyl-2-ethylpyridin-6-yl |
| A-216 | CH$_2$—CH$_2$—CH$_2$—CH$_2$ | — | 4-tert-butyl-2-n-propylpyridin-6-yl |
| A-217 | CH$_2$—CH$_2$—CH$_2$—CH$_2$ | — | 4-tert-butyl-2-isopropylpyridin-6-yl |
| A-218 | CH$_2$—CH$_2$—CH$_2$—CH$_2$ | — | 4-tert-butyl-2-cyclopropylpyridin-6-yl |
| A-219 | CH$_2$—CH$_2$—CH$_2$—CH$_2$ | — | 4-tert-butyl-2-cyclobutylpyridin-6-yl |
| A-220 | trans-CH$_2$—CH=CH—CH$_2$ | — | 4-tert-butyl-2-trifluoromethylpyridin-6-yl |
| A-221 | trans-CH$_2$—CH=CH—CH$_2$ | — | 4-tert-butyl-2-difluoromethylpyridin-6-yl |
| A-222 | trans-CH$_2$—CH=CH—CH$_2$ | — | 4-tert-butyl-2-phenylpyridin-6-yl |
| A-223 | trans-CH$_2$—CH=CH—CH$_2$ | — | 4-tert-butyl-2-methylpyridin-6-yl |
| A-224 | trans-CH$_2$—CH=CH—CH$_2$ | — | 4-tert-butyl-2-ethylpyridin-6-yl |
| A-225 | trans-CH$_2$—CH=CH—CH$_2$ | — | 4-tert-butyl-2-n-propylpyridin-6-yl |
| A-226 | trans-CH$_2$—CH=CH—CH$_2$ | — | 4-tert-butyl-2-isopropylpyridin-6-yl |
| A-227 | trans-CH$_2$—CH=CH—CH$_2$ | — | 4-tert-butyl-2-cyclopropylpyridin-6-yl |
| A-228 | trans-CH$_2$—CH=CH—CH$_2$ | — | 4-tert-butyl-2-cyclobutylpyridin-6-yl |
| A-229 | trans-CH$_2$—C(CH$_3$)=CH—CH$_2$ | — | 4-tert-butyl-2-trifluoromethylpyridin-6-yl |
| A-230 | trans-CH$_2$—C(CH$_3$)=CH—CH$_2$ | — | 4-tert-butyl-2-difluoromethylpyridin-6-yl |
| A-231 | trans-CH$_2$—C(CH$_3$)=CH—CH$_2$ | — | 4-tert-butyl-2-phenylpyridin-6-yl |
| A-232 | trans-CH$_2$—C(CH$_3$)=CH—CH$_2$ | — | 4-tert-butyl-2-methylpyridin-6-yl |
| A-233 | trans-CH$_2$—C(CH$_3$)=CH—CH$_2$ | — | 4-tert-butyl-2-ethylpyridin-6-yl |
| A-234 | trans-CH$_2$—C(CH$_3$)=CH—CH$_2$ | — | 4-tert-butyl-2-n-propylpyridin-6-yl |
| A-235 | trans-CH$_2$—C(CH$_3$)=CH—CH$_2$ | — | 4-tert-butyl-2-isopropylpyridin-6-yl |
| A-236 | trans-CH$_2$—C(CH$_3$)=CH—CH$_2$ | — | 4-tert-butyl-2-cyclopropylpyridin-6-yl |
| A-237 | trans-CH$_2$—C(CH$_3$)=CH—CH$_2$ | — | 4-tert-butyl-2-cyclobutylpyridin-6-yl |
| A-238 | CH$_2$—CH(CH$_3$)—CH$_2$—CH$_2$ | — | 4-tert-butyl-2-trifluoromethylpyridin-6-yl |
| A-239 | CH$_2$—CH(CH$_3$)—CH$_2$—CH$_2$ | — | 4-tert-butyl-2-difluoromethylpyridin-6-yl |
| A-240 | CH$_2$—CH(CH$_3$)—CH$_2$—CH$_2$ | — | 4-tert-butyl-2-phenylpyridin-6-yl |
| A-241 | CH$_2$—CH(CH$_3$)—CH$_2$—CH$_2$ | — | 4-tert-butyl-2-methylpyridin-6-yl |
| A-242 | CH$_2$—CH(CH$_3$)—CH$_2$—CH$_2$ | — | 4-tert-butyl-2-ethylpyridin-6-yl |
| A-243 | CH$_2$—CH(CH$_3$)—CH$_2$—CH$_2$ | — | 4-tert-butyl-2-n-propylpyridin-6-yl |
| A-244 | CH$_2$—CH(CH$_3$)—CH$_2$—CH$_2$ | — | 4-tert-butyl-2-isopropylpyridin-6-yl |
| A-245 | CH$_2$—CH(CH$_3$)—CH$_2$—CH$_2$ | — | 4-tert-butyl-2-cyclopropylpyridin-6-yl |
| A-246 | CH$_2$—CH(CH$_3$)—CH$_2$—CH$_2$ | — | 4-tert-butyl-2-cyclobutylpyridin-6-yl |
| A-247 | CH$_2$—CH$_2$—CH$_2$—CH(CH$_3$) | — | 4-tert-butyl-2-trifluoromethylpyridin-6-yl |
| A-248 | CH$_2$—CH$_2$—CH$_2$—CH(CH$_3$) | — | 4-tert-butyl-2-difluoromethylpyridin-6-yl |
| A-249 | CH$_2$—CH$_2$—CH$_2$—CH(CH$_3$) | — | 4-tert-butyl-2-phenylpyridin-6-yl |
| A-250 | CH$_2$—CH$_2$—CH$_2$—CH(CH$_3$) | — | 4-tert-butyl-2-methylpyridin-6-yl |
| A-251 | CH$_2$—CH$_2$—CH$_2$—CH(CH$_3$) | — | 4-tert-butyl-2-ethylpyridin-6-yl |
| A-252 | CH$_2$—CH$_2$—CH$_2$—CH(CH$_3$) | — | 4-tert-butyl-2-n-propylpyridin-6-yl |
| A-253 | CH$_2$—CH$_2$—CH$_2$—CH(CH$_3$) | — | 4-tert-butyl-2-isopropylpyridin-6-yl |
| A-254 | CH$_2$—CH$_2$—CH$_2$—CH(CH$_3$) | — | 4-tert-butyl-2-cyclopropylpyridin-6-yl |
| A-255 | CH$_2$—CH$_2$—CH$_2$—CH(CH$_3$) | — | 4-tert-butyl-2-cyclobutylpyridin-6-yl |
| A-256 | C(O)—CH$_2$—CH$_2$—CH$_2$ | — | 4-tert-butyl-2-trifluoromethylpyridin-6-yl |
| A-257 | C(O)—CH$_2$—CH$_2$—CH$_2$ | — | 4-tert-butyl-2-difluoromethylpyridin-6-yl |
| A-258 | C(O)—CH$_2$—CH$_2$—CH$_2$ | — | 4-tert-butyl-2-phenylpyridin-6-yl |
| A-259 | C(O)—CH$_2$—CH$_2$—CH$_2$ | — | 4-tert-butyl-2-methylpyridin-6-yl |
| A-260 | C(O)—CH$_2$—CH$_2$—CH$_2$ | — | 4-tert-butyl-2-ethylpyridin-6-yl |
| A-261 | C(O)—CH$_2$—CH$_2$—CH$_2$ | — | 4-tert-butyl-2-n-propylpyridin-6-yl |
| A-262 | C(O)—CH$_2$—CH$_2$—CH$_2$ | — | 4-tert-butyl-2-isopropylpyridin-6-yl |
| A-263 | C(O)—CH$_2$—CH$_2$—CH$_2$ | — | 4-tert-butyl-2-cyclopropylpyridin-6-yl |
| A-264 | C(O)—CH$_2$—CH$_2$—CH$_2$ | — | 4-tert-butyl-2-cyclobutylpyridin-6-yl |

TABLE A-continued

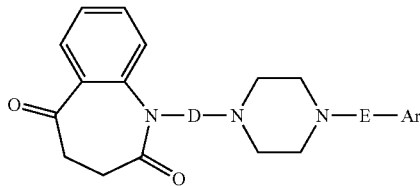

(I-Aa.a)

| | D | E | $R^a$ |
|---|---|---|---|
| A-265 | C(O)—CH$_2$—CH$_2$—CH$_2$—CH$_2$ | — | 4-tert-butyl-2-trifluoromethylpyridin-6-yl |
| A-266 | C(O)—CH$_2$—CH$_2$—CH$_2$—CH$_2$ | — | 4-tert-butyl-2-difluoromethylpyridin-6-yl |
| A-267 | C(O)—CH$_2$—CH$_2$—CH$_2$—CH$_2$ | — | 4-tert-butyl-2-phenylpyridin-6-yl |
| A-268 | C(O)—CH$_2$—CH$_2$—CH$_2$—CH$_2$ | — | 4-tert-butyl-2-methylpyridin-6-yl |
| A-269 | C(O)—CH$_2$—CH$_2$—CH$_2$—CH$_2$ | — | 4-tert-butyl-2-ethylpyridin-6-yl |
| A-270 | C(O)—CH$_2$—CH$_2$—CH$_2$—CH$_2$ | — | 4-tert-butyl-2-n-propylpyridin-6-yl |
| A-271 | C(O)—CH$_2$—CH$_2$—CH$_2$—CH$_2$ | — | 4-tert-butyl-2-isopropylpyridin-6-yl |
| A-272 | C(O)—CH$_2$—CH$_2$—CH$_2$—CH$_2$ | — | 4-tert-butyl-2-cyclopropylpyridin-6-yl |
| A-273 | C(O)—CH$_2$—CH$_2$—CH$_2$—CH$_2$ | — | 4-tert-butyl-2-cyclobutylpyridin-6-yl |
| A-274 | CH$_2$—CH$_2$—CH$_2$—CH$_2$ | — | 2-tert-butyl-6-trifluoromethylpyrimidin-4-yl |
| A-275 | CH$_2$—CH$_2$—CH$_2$—CH$_2$ | — | 2-tert-butyl-6-difluoromethylpyrimidin-4-yl |
| A-276 | CH$_2$—CH$_2$—CH$_2$—CH$_2$ | — | 2-tert-butyl-6-phenylpyrimidin-4-yl |
| A-277 | CH$_2$—CH$_2$—CH$_2$—CH$_2$ | — | 2-tert-butyl-6-methylpyrimidin-4-yl |
| A-278 | CH$_2$—CH$_2$—CH$_2$—CH$_2$ | — | 2-tert-butyl-6-ethylpyrimidin-4-yl |
| A-279 | CH$_2$—CH$_2$—CH$_2$—CH$_2$ | — | 2-tert-butyl-6-n-propylpyrimidin-4-yl |
| A-280 | CH$_2$—CH$_2$—CH$_2$—CH$_2$ | — | 2-tert-butyl-6-isopropylpyrimidin-4-yl |
| A-281 | CH$_2$—CH$_2$—CH$_2$—CH$_2$ | — | 2,6-bis(tert-butyl)pyrimidin-4-yl |
| A-282 | CH$_2$—CH$_2$—CH$_2$—CH$_2$ | — | 2-tert-butyl-6-cyclopropylpyrimidin-4-yl |
| A-283 | CH$_2$—CH$_2$—CH$_2$—CH$_2$ | — | 2-tert-butyl-6-cyclobutylpyrimidin-4-yl |
| A-284 | trans-CH$_2$—CH=CH—CH$_2$ | — | 2-tert-butyl-6-trifluoromethylpyrimidin-4-yl |
| A-285 | trans-CH$_2$—CH=CH—CH$_2$ | — | 2-tert-butyl-6-difluoromethylpyrimidin-4-yl |
| A-286 | trans-CH$_2$—CH=CH—CH$_2$ | — | 2-tert-butyl-6-phenylpyrimidin-4-yl |
| A-287 | trans-CH$_2$—CH=CH—CH$_2$ | — | 2-tert-butyl-6-methylpyrimidin-4-yl |
| A-288 | trans-CH$_2$—CH=CH—CH$_2$ | — | 2-tert-butyl-6-ethylpyrimidin-4-yl |
| A-289 | trans-CH$_2$—CH=CH—CH$_2$ | — | 2-tert-butyl-6-n-propylpyrimidin-4-yl |
| A-290 | trans-CH$_2$—CH=CH—CH$_2$ | — | 2-tert-butyl-6-isopropylpyrimidin-4-yl |
| A-291 | trans-CH$_2$—CH=CH—CH$_2$ | — | 2,6-bis(tert-butyl)pyrimidin-4-yl |
| A-292 | trans-CH$_2$—CH=CH—CH$_2$ | — | 2-tert-butyl-6-cyclopropylpyrimidin-4-yl |
| A-293 | trans-CH$_2$—CH=CH—CH$_2$ | — | 2-tert-butyl-6-cyclobutylpyrimidin-4-yl |
| A-294 | trans-CH$_2$—C(CH$_3$)=CH—CH$_2$ | — | 2-tert-butyl-6-trifluoromethylpyrimidin-4-yl |
| A-295 | trans-CH$_2$—C(CH$_3$)=CH—CH$_2$ | — | 2-tert-butyl-6-difluoromethylpyrimidin-4-yl |
| A-296 | trans-CH$_2$—C(CH$_3$)=CH—CH$_2$ | — | 2-tert-butyl-6-phenylpyrimidin-4-yl |
| A-297 | trans-CH$_2$—C(CH$_3$)=CH—CH$_2$ | — | 2-tert-butyl-6-methylpyrimidin-4-yl |
| A-298 | trans-CH$_2$—C(CH$_3$)=CH—CH$_2$ | — | 2-tert-butyl-6-ethylpyrimidin-4-yl |
| A-299 | trans-CH$_2$—C(CH$_3$)=CH—CH$_2$ | — | 2-tert-butyl-6-n-propylpyrimidin-4-yl |
| A-300 | trans-CH$_2$—C(CH$_3$)=CH—CH$_2$ | — | 2-tert-butyl-6-isopropylpyrimidin-4-yl |
| A-301 | trans-CH$_2$—C(CH$_3$)=CH—CH$_2$ | — | 2,6-bis(tert-butyl)pyrimidin-4-yl |
| A-302 | trans-CH$_2$—C(CH$_3$)=CH—CH$_2$ | — | 2-tert-butyl-6-cyclopropylpyrimidin-4-yl |
| A-303 | trans-CH$_2$—C(CH$_3$)=CH—CH$_2$ | — | 2-tert-butyl-6-cyclobutylpyrimidin-4-yl |
| A-304 | CH$_2$—CH(CH$_3$)—CH$_2$—CH$_2$ | — | 2-tert-butyl-6-trifluoromethylpyrimidin-4-yl |
| A-305 | CH$_2$—CH(CH$_3$)—CH$_2$—CH$_2$ | — | 2-tert-butyl-6-difluoromethylpyrimidin-4-yl |
| A-306 | CH$_2$—CH(CH$_3$)—CH$_2$—CH$_2$ | — | 2-tert-butyl-6-phenylpyrimidin-4-yl |
| A-307 | CH$_2$—CH(CH$_3$)—CH$_2$—CH$_2$ | — | 2-tert-butyl-6-methylpyrimidin-4-yl |
| A-308 | CH$_2$—CH(CH$_3$)—CH$_2$—CH$_2$ | — | 2-tert-butyl-6-ethylpyrimidin-4-yl |
| A-309 | CH$_2$—CH(CH$_3$)—CH$_2$—CH$_2$ | — | 2-tert-butyl-6-n-propylpyrimidin-4-yl |
| A-310 | CH$_2$—CH(CH$_3$)—CH$_2$—CH$_2$ | — | 2-tert-butyl-6-isopropylpyrimidin-4-yl |
| A-311 | CH$_2$—CH(CH$_3$)—CH$_2$—CH$_2$ | — | 2-6-bis(tert-butyl)pyrimidin-4-yl |
| A-312 | CH$_2$—CH(CH$_3$)—CH$_2$—CH$_2$ | — | 2-tert-butyl-6-cyclopropylpyrimidin-4-yl |
| A-313 | CH$_2$—CH(CH$_3$)—CH$_2$—CH$_2$ | — | 2-tert-butyl-6-cyclobutylpyrimidin-4-yl |
| A-314 | CH$_2$—CH$_2$—CH$_2$—CH(CH$_3$) | — | 2-tert-butyl-6-trifluoromethylpyrimidin-4-yl |
| A-315 | CH$_2$—CH$_2$—CH$_2$—CH(CH$_3$) | — | 2-tert-butyl-6-difluoromethylpyrimidin-4-yl |
| A-316 | CH$_2$—CH$_2$—CH$_2$—CH(CH$_3$) | — | 2-tert-butyl-6-phenylpyrimidin-4-yl |
| A-317 | CH$_2$—CH$_2$—CH$_2$—CH(CH$_3$) | — | 2-tert-butyl-6-methylpyrimidin-4-yl |
| A-318 | CH$_2$—CH$_2$—CH$_2$—CH(CH$_3$) | — | 2-tert-butyl-6-ethylpyrimidin-4-yl |
| A-319 | CH$_2$—CH$_2$—CH$_2$—CH(CH$_3$) | — | 2-tert-butyl-6-n-propylpyrimidin-4-yl |
| A-320 | CH$_2$—CH$_2$—CH$_2$—CH(CH$_3$) | — | 2-tert-butyl-6-isopropylpyrimidin-4-yl |
| A-321 | CH$_2$—CH$_2$—CH$_2$—CH(CH$_3$) | — | 2,6-bis(tert-butyl)pyrimidin-4-yl |
| A-322 | CH$_2$—CH$_2$—CH$_2$—CH(CH$_3$) | — | 2-tert-butyl-6-cyclopropylpyrimidin-4-yl |
| A-323 | CH$_2$—CH$_2$—CH$_2$—CH(CH$_3$) | — | 2-tert-butyl-6-cyclobutylpyrimidin-4-yl |
| A-324 | C(O)—CH$_2$—CH$_2$—CH$_2$ | — | 2-tert-butyl-6-trifluoromethylpyrimidin-4-yl |
| A-325 | C(O)—CH$_2$—CH$_2$—CH$_2$ | — | 2-tert-butyl-6-difluoromethylpyrimidin-4-yl |
| A-326 | C(O)—CH$_2$—CH$_2$—CH$_2$ | — | 2-tert-butyl-6-phenylpyrimidin-4-yl |
| A-327 | C(O)—CH$_2$—CH$_2$—CH$_2$ | — | 2-tert-butyl-6-methylpyrimidin-4-yl |
| A-328 | C(O)—CH$_2$—CH$_2$—CH$_2$ | — | 2-tert-butyl-6-ethylpyrimidin-4-yl |
| A-329 | C(O)—CH$_2$—CH$_2$—CH$_2$ | — | 2-tert-butyl-6-n-propylpyrimidin-4-yl |
| A-330 | C(O)—CH$_2$—CH$_2$—CH$_2$ | — | 2-tert-butyl-6-isopropylpyrimidin-4-yl |

TABLE A-continued

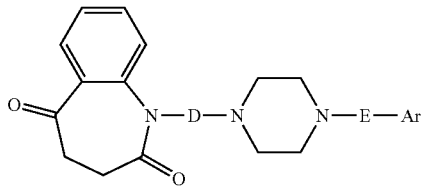

(I-Aa.a)

| | D | E | R$^a$ |
|---|---|---|---|
| A-331 | C(O)—CH$_2$—CH$_2$—CH$_2$ | — | 2,6-bis(tert-butyl)pyrimidin-4-yl |
| A-332 | C(O)—CH$_2$—CH$_2$—CH$_2$ | — | 2-tert-butyl-6-cyclopropylpyrimidin-4-yl |
| A-333 | C(O)—CH$_2$—CH$_2$—CH$_2$ | — | 2-tert-butyl-6-cyclobutylpyrimidin-4-yl |
| A-334 | C(O)—CH$_2$—CH$_2$—CH$_2$—CH$_2$ | — | 2-tert-butyl-6-trifluoromethylpyrimidin-4-yl |
| A-335 | C(O)—CH$_2$—CH$_2$—CH$_2$—CH$_2$ | — | 2-tert-butyl-6-difluoromethylpyrimidin-4-yl |
| A-336 | C(O)—CH$_2$—CH$_2$—CH$_2$—CH$_2$ | — | 2-tert-butyl-6-phenylpyrimidin-4-yl |
| A-337 | C(O)—CH$_2$—CH$_2$—CH$_2$—CH$_2$ | — | 2-tert-butyl-6-methylpyrimidin-4-yl |
| A-338 | C(O)—CH$_2$—CH$_2$—CH$_2$—CH$_2$ | — | 2-tert-butyl-6-ethylpyrimidin-4-yl |
| A-339 | C(O)—CH$_2$—CH$_2$—CH$_2$—CH$_2$ | — | 2-tert-butyl-6-n-propylpyrimidin-4-yl |
| A-340 | C(O)—CH$_2$—CH$_2$—CH$_2$—CH$_2$ | — | 2-tert-butyl-6-isopropylpyrimidin-4-yl |
| A-341 | C(O)—CH$_2$—CH$_2$—CH$_2$—CH$_2$ | — | 2,6-bis(tert-butyl)pyrimidin-4-yl |
| A-342 | C(O)—CH$_2$—CH$_2$—CH$_2$—CH$_2$ | — | 2-tert-butyl-6-cyclopropylpyrimidin-4-yl |
| A-343 | C(O)—CH$_2$—CH$_2$—CH$_2$—CH$_2$ | — | 2-tert-butyl-6-cyclobutylpyrimidin-4-yl |
| A-344 | CH$_2$—CH$_2$—CH$_2$—CH$_2$ | — | 5-tert-butyl-3-trifluoromethylphenyl |
| A-345 | CH$_2$—CH$_2$—CH$_2$—CH$_2$ | — | 5-tert-butyl-3-difluoromethylphenyl |
| A-346 | CH$_2$—CH$_2$—CH$_2$—CH$_2$ | — | 5-tert-butyl-3-phenylphenyl |
| A-347 | CH$_2$—CH$_2$—CH$_2$—CH$_2$ | — | 3-tert-butyl-5-methylphenyl |
| A-348 | CH$_2$—CH$_2$—CH$_2$—CH$_2$ | — | 3-tert-butyl-5-ethylphenyl |
| A-349 | CH$_2$—CH$_2$—CH$_2$—CH$_2$ | — | 3-tert-butyl-5-n-propylphenyl |
| A-350 | CH$_2$—CH$_2$—CH$_2$—CH$_2$ | — | 3-tert-butyl-5-isopropylphenyl |
| A-351 | CH$_2$—CH$_2$—CH$_2$—CH$_2$ | — | 3,5-bis(tert-butyl)phenyl |
| A-352 | CH$_2$—CH$_2$—CH$_2$—CH$_2$ | — | 3-tert-butyl-5-cyclopropylphenyl |
| A-353 | CH$_2$—CH$_2$—CH$_2$—CH$_2$ | — | 3-tert-butyl-5-cyclobutylphenyl |
| A-354 | trans-CH$_2$—CH=CH—CH$_2$ | — | 5-tert-butyl-3-trifluoromethylphenyl |
| A-355 | trans-CH$_2$—CH=CH—CH$_2$ | — | 5-tert-butyl-3-difluoromethylphenyl |
| A-356 | trans-CH$_2$—CH=CH—CH$_2$ | — | 5-tert-butyl-3-phenylphenyl |
| A-357 | trans-CH$_2$—CH=CH—CH$_2$ | — | 3-tert-butyl-5-methylphenyl |
| A-358 | trans-CH$_2$—CH=CH—CH$_2$ | — | 3-tert-butyl-5-ethylphenyl |
| A-359 | trans-CH$_2$—CH=CH—CH$_2$ | — | 3-tert-butyl-5-n-propylphenyl |
| A-360 | trans-CH$_2$—CH=CH—CH$_2$ | — | 3-tert-butyl-5-isopropylphenyl |
| A-361 | trans-CH$_2$—CH=CH—CH$_2$ | — | 3,5-bis(tert-butyl)phenyl |
| A-362 | trans-CH$_2$—CH=CH—CH$_2$ | — | 3-tert-butyl-5-cyclopropylphenyl |
| A-363 | trans-CH$_2$—CH=CH—CH$_2$ | — | 3-tert-butyl-5-cyclobutylphenyl |
| A-364 | trans-CH$_2$—C(CH$_3$)=CH—CH$_2$ | — | 5-tert-butyl-3-trifluoromethylphenyl |
| A-365 | trans-CH$_2$—C(CH$_3$)=CH—CH$_2$ | — | 5-tert-butyl-3-difluoromethylphenyl |
| A-366 | trans-CH$_2$—C(CH$_3$)=CH—CH$_2$ | — | 5-tert-butyl-3-phenylphenyl |
| A-367 | trans-CH$_2$—C(CH$_3$)=CH—CH$_2$ | — | 3-tert-butyl-5-methylphenyl |
| A-368 | trans-CH$_2$—C(CH$_3$)=CH—CH$_2$ | — | 3-tert-butyl-5-ethylphenyl |
| A-369 | trans-CH$_2$—C(CH$_3$)=CH—CH$_2$ | — | 3-tert-butyl-5-n-propylphenyl |
| A-370 | trans-CH$_2$—C(CH$_3$)=CH—CH$_2$ | — | 3-tert-butyl-5-isopropylphenyl |
| A-371 | trans-CH$_2$—C(CH$_3$)=CH—CH$_2$ | — | 3,5-bis(tert-butyl)phenyl |
| A-372 | trans-CH$_2$—C(CH$_3$)=CH—CH$_2$ | — | 3-tert-butyl-5-cyclopropylphenyl |
| A-373 | trans-CH$_2$—C(CH$_3$)=CH—CH$_2$ | — | 3-tert-butyl-5-cyclobutylphenyl |
| A-374 | CH$_2$—CH(CH$_3$)—CH$_2$—CH$_2$ | — | 5-tert-butyl-3-trifluoromethylphenyl |
| A-375 | CH$_2$—CH(CH$_3$)—CH$_2$—CH$_2$ | — | 5-tert-butyl-3-difluoromethylphenyl |
| A-376 | CH$_2$—CH(CH$_3$)—CH$_2$—CH$_2$ | — | 5-tert-butyl-3-phenylphenyl |
| A-377 | CH$_2$—CH(CH$_3$)—CH$_2$—CH$_2$ | — | 3-tert-butyl-5-methylphenyl |
| A-378 | CH$_2$—CH(CH$_3$)—CH$_2$—CH$_2$ | — | 3-tert-butyl-5-ethylphenyl |
| A-379 | CH$_2$—CH(CH$_3$)—CH$_2$—CH$_2$ | — | 3-tert-butyl-5-n-propylphenyl |
| A-380 | CH$_2$—CH(CH$_3$)—CH$_2$—CH$_2$ | — | 3-tert-butyl-5-isopropylphenyl |
| A-381 | CH$_2$—CH(CH$_3$)—CH$_2$—CH$_2$ | — | 3,5-bis(tert-butyl)phenyl |
| A-382 | CH$_2$—CH(CH$_3$)—CH$_2$—CH$_2$ | — | 3-tert-butyl-5-cyclopropylphenyl |
| A-383 | CH$_2$—CH(CH$_3$)—CH$_2$—CH$_2$ | — | 3-tert-butyl-5-cyclobutylphenyl |
| A-384 | CH$_2$—CH$_2$—CH$_2$—CH(CH$_3$) | — | 5-tert-butyl-3-trifluoromethylphenyl |
| A-385 | CH$_2$—CH$_2$—CH$_2$—CH(CH$_3$) | — | 5-tert-butyl-3-difluoromethylphenyl |
| A-386 | CH$_2$—CH$_2$—CH$_2$—CH(CH$_3$) | — | 5-tert-butyl-3-phenylphenyl |
| A-387 | CH$_2$—CH$_2$—CH$_2$—CH(CH$_3$) | — | 3-tert-butyl-5-methylphenyl |
| A-388 | CH$_2$—CH$_2$—CH$_2$—CH(CH$_3$) | — | 3-tert-butyl-5-ethylphenyl |
| A-389 | CH$_2$—CH$_2$—CH$_2$—CH(CH$_3$) | — | 3-tert-butyl-5-n-propylphenyl |
| A-390 | CH$_2$—CH$_2$—CH$_2$—CH(CH$_3$) | — | 3-tert-butyl-5-isopropylphenyl |
| A-391 | CH$_2$—CH$_2$—CH$_2$—CH(CH$_3$) | — | 3-5-bis(tert-butyl)phenyl |
| A-392 | CH$_2$—CH$_2$—CH$_2$—CH(CH$_3$) | — | 3-tert-butyl-5-cyclopropylphenyl |
| A-393 | CH$_2$—CH$_2$—CH$_2$—CH(CH$_3$) | — | 3-tert-butyl-5-cyclobutylphenyl |
| A-394 | C(O)—CH$_2$—CH$_2$—CH$_2$ | — | 5-tert-butyl-3-trifluoromethylphenyl |
| A-395 | C(O)—CH$_2$—CH$_2$—CH$_2$ | — | 5-tert-butyl-3-difluoromethylphenyl |
| A-396 | C(O)—CH$_2$—CH$_2$—CH$_2$ | — | 5-tert-butyl-3-phenylphenyl |

TABLE A-continued (I-Aa.a)

| | D | E | R$^a$ |
|---|---|---|---|
| A-397 | C(O)—CH$_2$—CH$_2$—CH$_2$ | — | 3-tert-butyl-5-methylphenyl |
| A-398 | C(O)—CH$_2$—CH$_2$—CH$_2$ | — | 3-tert-butyl-5-ethylphenyl |
| A-399 | C(O)—CH$_2$—CH$_2$—CH$_2$ | — | 3-tert-butyl-5-n-propylphenyl |
| A-400 | C(O)—CH$_2$—CH$_2$—CH$_2$ | — | 3-tert-butyl-5-isopropylphenyl |
| A-401 | C(O)—CH$_2$—CH$_2$—CH$_2$ | — | 3,5-bis(tert-butyl)phenyl |
| A-402 | C(O)—CH$_2$—CH$_2$—CH$_2$ | — | 3-tert-butyl-5-cyclopropylphenyl |
| A-403 | C(O)—CH$_2$—CH$_2$—CH$_2$ | — | 3-tert-butyl-5-cyclobutylphenyl |
| A-404 | C(O)—CH$_2$—CH$_2$—CH$_2$—CH$_2$ | — | 5-tert-butyl-3-trifluoromethylphenyl |
| A-405 | C(O)—CH$_2$—CH$_2$—CH$_2$—CH$_2$ | — | 5-tert-butyl-3-difluoromethylphenyl |
| A-406 | C(O)—CH$_2$—CH$_2$—CH$_2$—CH$_2$ | — | 5-tert-butyl-3-phenylphenyl |
| A-407 | C(O)—CH$_2$—CH$_2$—CH$_2$—CH$_2$ | — | 3-tert-butyl-5-methylphenyl |
| A-408 | C(O)—CH$_2$—CH$_2$—CH$_2$—CH$_2$ | — | 3-tert-butyl-5-ethylphenyl |
| A-409 | C(O)—CH$_2$—CH$_2$—CH$_2$—CH$_2$ | — | 3-tert-butyl-5-n-propylphenyl |
| A-410 | C(O)—CH$_2$—CH$_2$—CH$_2$—CH$_2$ | — | 3-tert-butyl-5-isopropylphenyl |
| A-411 | C(O)—CH$_2$—CH$_2$—CH$_2$—CH$_2$ | — | 3,5-bis(tert-butyl)phenyl |
| A-412 | C(O)—CH$_2$—CH$_2$—CH$_2$—CH$_2$ | — | 3-tert-butyl-5-cyclopropylphenyl |
| A-413 | C(O)—CH$_2$—CH$_2$—CH$_2$—CH$_2$ | — | 3-tert-butyl-5-cyclobutylphenyl |
| A-414 | | | |
| A-415 | CH$_2$—CH$_2$—CH$_2$—CH$_2$ | — | 2-methylphenyl |
| A-416 | CH$_2$—CH$_2$—CH$_2$—CH$_2$ | — | 2-fluorophenyl |
| A-417 | CH$_2$—CH$_2$—CH$_2$—CH$_2$ | — | 2,3-dimethylphenyl |
| A-418 | CH$_2$—CH$_2$—CH$_2$—CH$_2$ | — | 2-methoxyphenyl |
| A-419 | CH$_2$—CH$_2$—CH$_2$—CH$_2$ | — | 2-chlorophenyl |
| A-420 | CH$_2$—CH$_2$—CH$_2$—CH$_2$ | — | 2-ethoxyphenyl |
| A-421 | CH$_2$—CH$_2$—CH$_2$—CH$_2$ | — | 3-trifluoromethylphenyl |
| A-422 | CH$_2$—CH$_2$—CH$_2$—CH$_2$ | — | 2,4-dichlorophenyl |
| A-423 | CH$_2$—CH$_2$—CH$_2$—CH$_2$ | — | 3,5-dichlorophenyl |
| A-424 | CH$_2$—CH$_2$—CH$_2$—CH$_2$ | — | 2,3-dichlorophenyl |
| A-425 | CH$_2$—CH$_2$—CH$_2$—CH$_2$ | — | 3-chloro-6-methoxyphenyl |
| A-426 | CH$_2$—CH$_2$—CH$_2$—CH$_2$ | — | 3,5-dimethylphenyl |
| A-427 | CH$_2$—CH$_2$—CH$_2$—CH$_2$ | — | 2-cyanophenyl |
| A-428 | CH$_2$—CH$_2$—CH$_2$—CH$_2$ | — | 4-chloro-3-trifluoromethylphenyl |
| A-429 | CH$_2$—CH$_2$—CH$_2$—CH$_2$ | — | 3,5-trifluoromethylphenyl |
| A-430 | CH$_2$—CH$_2$—CH$_2$—CH$_2$ | — | 2-methylpyridin-6-yl |
| A-431 | CH$_2$—CH$_2$—CH$_2$—CH$_2$ | — | 3-cyanopyridin-2-yl |
| A-432 | CH$_2$—CH$_2$—CH$_2$—CH$_2$ | — | 3-cyanopyridin-6-yl |
| A-433 | CH$_2$—CH$_2$—CH$_2$—CH$_2$ | — | 3-trifluoromethylpyridin-2-yl |
| A-434 | CH$_2$—CH$_2$—CH$_2$—CH$_2$ | — | 3-trifluoromethylpyridin-6-yl |
| A-435 | CH$_2$—CH$_2$—CH$_2$—CH$_2$ | — | 3-chloro-5-trifluoromethylpyridin-2-yl |
| A-436 | CH$_2$—CH$_2$—CH$_2$—CH$_2$ | — | 3,5-dichloropyridin-4-yl |
| A-437 | CH$_2$—CH$_2$—CH$_2$—CH$_2$ | — | 4-trifluoropyrimidin-2-yl |
| A-438 | CH$_2$—CH$_2$—CH$_2$—CH$_2$ | — | 5-bromopyrimidin-2-yl |
| A-439 | CH$_2$—CH$_2$—CH$_2$—CH$_2$ | — | 5-fluoropyrimidin-2-yl |
| A-440 | CH$_2$—CH$_2$—CH$_2$—CH$_2$ | — | 2-cyanopyridazin-3-yl |
| A-441 | CH$_2$—CH$_2$—CH$_2$—CH$_2$ | — | 5-nitrothiadiazol-2-yl |
| A-442 | CH$_2$—CH$_2$—CH$_2$—CH$_2$ | — | 4-methylthiadiazol-2-yl |
| A-443 | trans-CH$_2$—CH=CH—CH$_2$ | — | 2-methylphenyl |
| A-444 | trans-CH$_2$—CH=CH—CH$_2$ | — | 2-fluorophenyl |
| A-445 | trans-CH$_2$—CH=CH—CH$_2$ | — | 2,3-dimethylphenyl |
| A-446 | trans-CH$_2$—CH=CH—CH$_2$ | — | 2-methoxyphenyl |
| A-447 | trans-CH$_2$—CH=CH—CH$_2$ | — | 2-chlorophenyl |
| A-448 | trans-CH$_2$—CH=CH—CH$_2$ | — | 2-ethoxyphenyl |
| A-449 | trans-CH$_2$—CH=CH—CH$_2$ | — | 3-trifluoromethylphenyl |
| A-450 | trans-CH$_2$—CH=CH—CH$_2$ | — | 2,4-dichlorophenyl |
| A-451 | trans-CH$_2$—CH=CH—CH$_2$ | — | 3,5-dichlorophenyl |
| A-452 | trans-CH$_2$—CH=CH—CH$_2$ | — | 2,3-dichlorophenyl |
| A-453 | trans-CH$_2$—CH=CH—CH$_2$ | — | 3-chloro-6-methoxyphenyl |
| A-454 | trans-CH$_2$—CH=CH—CH$_2$ | — | 3,5-dimethylphenyl |
| A-455 | trans-CH$_2$—CH=CH—CH$_2$ | — | 2-cyanophenyl |
| A-456 | trans-CH$_2$—CH=CH—CH$_2$ | — | 4-chloro-3-trifluoromethylphenyl |
| A-457 | trans-CH$_2$—CH=CH—CH$_2$ | — | 3,5-trifluoromethylphenyl |
| A-458 | trans-CH$_2$—CH=CH—CH$_2$ | — | 2-methylpyridin-6-yl |
| A-459 | trans-CH$_2$—CH=CH—CH$_2$ | — | 3-cyanopyridin-2-yl |
| A-460 | trans-CH$_2$—CH=CH—CH$_2$ | — | 3-cyanopyridin-6-yl |
| A-461 | trans-CH$_2$—CH=CH—CH$_2$ | — | 3-trifluoromethylpyridin-2-yl |
| A-462 | trans-CH$_2$—CH=CH—CH$_2$ | — | 3-trifluoromethylpyridin-6-yl |

TABLE A-continued (I-Aa.a)

| | D | E | $R^a$ |
|---|---|---|---|
| A-463 | trans-CH$_2$—CH=CH—CH$_2$ | — | 3-chloro-5-trifluoromethylpyridin-2-yl |
| A-464 | trans-CH$_2$—CH=CH—CH$_2$ | — | 3,5-dichloropyridin-4-yl |
| A-465 | trans-CH$_2$—CH=CH—CH$_2$ | — | 4-trifluoropyrimidin-2-yl |
| A-466 | trans-CH$_2$—CH=CH—CH$_2$ | — | 5-bromopyrimidin-2-yl |
| A-467 | trans-CH$_2$—CH=CH—CH$_2$ | — | 5-fluoropyrimidin-2-yl |
| A-468 | trans-CH$_2$—CH=CH—CH$_2$ | — | 2-cyanopyridazin-3-yl |
| A-469 | trans-CH$_2$—CH=CH—CH$_2$ | — | 5-nitrothiadiazol-2-yl |
| A-470 | trans-CH$_2$—CH=CH—CH$_2$ | — | 4-methylthiadiazol-2-yl |
| A-471 | trans-CH$_2$—C(CH$_3$)=CH—CH$_2$ | — | 2-methylphenyl |
| A-472 | trans-CH$_2$—C(CH$_3$)=CH—CH$_2$ | — | 2-fluorophenyl |
| A-473 | trans-CH$_2$—C(CH$_3$)=CH—CH$_2$ | — | 2,3-dimethylphenyl |
| A-474 | trans-CH$_2$—C(CH$_3$)=CH—CH$_2$ | — | 2-methoxyphenyl |
| A-475 | trans-CH$_2$—C(CH$_3$)=CH—CH$_2$ | — | 2-chlorophenyl |
| A-476 | trans-CH$_2$—C(CH$_3$)=CH—CH$_2$ | — | 2-ethoxyphenyl |
| A-477 | trans-CH$_2$—C(CH$_3$)=CH—CH$_2$ | — | 3-trifluoromethylphenyl |
| A-478 | trans-CH$_2$—C(CH$_3$)=CH—CH$_2$ | — | 2,4-dichlorophenyl |
| A-479 | trans-CH$_2$—C(CH$_3$)=CH—CH$_2$ | — | 3,5-dichlorophenyl |
| A-480 | trans-CH$_2$—C(CH$_3$)=CH—CH$_2$ | — | 2,3-dichlorophenyl |
| A-481 | trans-CH$_2$—C(CH$_3$)=CH—CH$_2$ | — | 3-chloro-6-methoxyphenyl |
| A-482 | trans-CH$_2$—C(CH$_3$)=CH—CH$_2$ | — | 3,5-dimethylphenyl |
| A-483 | trans-CH$_2$—C(CH$_3$)=CH—CH$_2$ | — | 2-cyanophenyl |
| A-484 | trans-CH$_2$—C(CH$_3$)=CH—CH$_2$ | — | 4-chloro-3-trifluoromethylphenyl |
| A-485 | trans-CH$_2$—C(CH$_3$)=CH—CH$_2$ | — | 3,5-trifluoromethylphenyl |
| A-486 | trans-CH$_2$—C(CH$_3$)=CH—CH$_2$ | — | 2-methylpyridin-6-yl |
| A-487 | trans-CH$_2$—C(CH$_3$)=CH—CH$_2$ | — | 3-cyanopyridin-2-yl |
| A-488 | trans-CH$_2$—C(CH$_3$)=CH—CH$_2$ | — | 3-cyanopyridin-6-yl |
| A-489 | trans-CH$_2$—C(CH$_3$)=CH—CH$_2$ | — | 3-trifluoromethylpyridin-2-yl |
| A-490 | trans-CH$_2$—C(CH$_3$)=CH—CH$_2$ | — | 3-trifluoromethylpyridin-6-yl |
| A-491 | trans-CH$_2$—C(CH$_3$)=CH—CH$_2$ | — | 3-chloro-5-trifluoromethylpyridin-2-yl |
| A-492 | trans-CH$_2$—C(CH$_3$)=CH—CH$_2$ | — | 3,5-dichloropyridin-4-yl |
| A-493 | trans-CH$_2$—C(CH$_3$)=CH—CH$_2$ | — | 4-trifluoropyrimidin-2-yl |
| A-494 | trans-CH$_2$—C(CH$_3$)=CH—CH$_2$ | — | 5-bromopyrimidin-2-yl |
| A-495 | trans-CH$_2$—C(CH$_3$)=CH—CH$_2$ | — | 5-fluoropyrimidin-2-yl |
| A-496 | trans-CH$_2$—C(CH$_3$)=CH—CH$_2$ | — | 2-cyanopyridazin-3-yl |
| A-497 | trans-CH$_2$—C(CH$_3$)=CH—CH$_2$ | — | 5-nitrothiadiazol-2-yl |
| A-498 | trans-CH$_2$—C(CH$_3$)=CH—CH$_2$ | — | 4-methylthiadiazol-2-yl |
| A-499 | CH$_2$—CH(CH$_3$)—CH$_2$—CH$_2$ | — | 2-methylphenyl |
| A-500 | CH$_2$—CH(CH$_3$)—CH$_2$—CH$_2$ | — | 2-fluorophenyl |
| A-501 | CH$_2$—CH(CH$_3$)—CH$_2$—CH$_2$ | — | 2,3-dimethylphenyl |
| A-502 | CH$_2$—CH(CH$_3$)—CH$_2$—CH$_2$ | — | 2-methoxyphenyl |
| A-503 | CH$_2$—CH(CH$_3$)—CH$_2$—CH$_2$ | — | 2-chlorophenyl |
| A-504 | CH$_2$—CH(CH$_3$)—CH$_2$—CH$_2$ | — | 2-ethoxyphenyl |
| A-505 | CH$_2$—CH(CH$_3$)—CH$_2$—CH$_2$ | — | 3-trifluoromethylphenyl |
| A-506 | CH$_2$—CH(CH$_3$)—CH$_2$—CH$_2$ | — | 2,4-dichlorophenyl |
| A-507 | CH$_2$—CH(CH$_3$)—CH$_2$—CH$_2$ | — | 3,5-dichlorophenyl |
| A-508 | CH$_2$—CH(CH$_3$)—CH$_2$—CH$_2$ | — | 2,3-dichlorophenyl |
| A-509 | CH$_2$—CH(CH$_3$)—CH$_2$—CH$_2$ | — | 3-chloro-6-methoxyphenyl |
| A-510 | CH$_2$—CH(CH$_3$)—CH$_2$—CH$_2$ | — | 3,5-dimethylphenyl |
| A-511 | CH$_2$—CH(CH$_3$)—CH$_2$—CH$_2$ | — | 2-cyanophenyl |
| A-512 | CH$_2$—CH(CH$_3$)—CH$_2$—CH$_2$ | — | 4-chloro-3-trifluoromethylphenyl |
| A-513 | CH$_2$—CH(CH$_3$)—CH$_2$—CH$_2$ | — | 3,5-trifluoromethylphenyl |
| A-514 | CH$_2$—CH(CH$_3$)—CH$_2$—CH$_2$ | — | 2-methylpyridin-6-yl |
| A-515 | CH$_2$—CH(CH$_3$)—CH$_2$—CH$_2$ | — | 3-cyanopyridin-2-yl |
| A-516 | CH$_2$—CH(CH$_3$)—CH$_2$—CH$_2$ | — | 3-cyanopyridin-6-yl |
| A-517 | CH$_2$—CH(CH$_3$)—CH$_2$—CH$_2$ | — | 3-trifluoromethylpyridin-2-yl |
| A-518 | CH$_2$—CH(CH$_3$)—CH$_2$—CH$_2$ | — | 3-trifluoromethylpyridin-6-yl |
| A-519 | CH$_2$—CH(CH$_3$)—CH$_2$—CH$_2$ | — | 3-chloro-5-trifluoromethylpyridin-2-yl |
| A-520 | CH$_2$—CH(CH$_3$)—CH$_2$—CH$_2$ | — | 3,5-dichloropyridin-4-yl |
| A-521 | CH$_2$—CH(CH$_3$)—CH$_2$—CH$_2$ | — | 4-trifluoropyrimidin-2-yl |
| A-522 | CH$_2$—CH(CH$_3$)—CH$_2$—CH$_2$ | — | 5-bromopyrimidin-2-yl |
| A-523 | CH$_2$—CH(CH$_3$)—CH$_2$—CH$_2$ | — | 5-fluoropyrimidin-2-yl |
| A-524 | CH$_2$—CH(CH$_3$)—CH$_2$—CH$_2$ | — | 2-cyanopyridazin-3-yl |
| A-525 | CH$_2$—CH(CH$_3$)—CH$_2$—CH$_2$ | — | 5-nitrothiadiazol-2-yl |
| A-526 | CH$_2$—CH(CH$_3$)—CH$_2$—CH$_2$ | — | 4-methylthiadiazol-2-yl |
| A-527 | CH$_2$—CH$_2$—CH$_2$—CH(CH$_3$) | — | 2-methylphenyl |
| A-528 | CH$_2$—CH$_2$—CH$_2$—CH(CH$_3$) | — | 2-fluorophenyl |

TABLE A-continued (I-Aa.a)

|  | D | E | R$^a$ |
|---|---|---|---|
| A-529 | CH$_2$—CH$_2$—CH$_2$—CH(CH$_3$) | — | 2,3-dimethylphenyl |
| A-530 | CH$_2$—CH$_2$—CH$_2$—CH(CH$_3$) | — | 2-methoxyphenyl |
| A-531 | CH$_2$—CH$_2$—CH$_2$—CH(CH$_3$) | — | 2-chlorophenyl |
| A-532 | CH$_2$—CH$_2$—CH$_2$—CH(CH$_3$) | — | 2-ethoxyphenyl |
| A-533 | CH$_2$—CH$_2$—CH$_2$—CH(CH$_3$) | — | 3-trifluoromethylphenyl |
| A-534 | CH$_2$—CH$_2$—CH$_2$—CH(CH$_3$) | — | 2,4-dichlorophenyl |
| A-535 | CH$_2$—CH$_2$—CH$_2$—CH(CH$_3$) | — | 3,5-dichlorophenyl |
| A-536 | CH$_2$—CH$_2$—CH$_2$—CH(CH$_3$) | — | 2,3-dichlorophenyl |
| A-537 | CH$_2$—CH$_2$—CH$_2$—CH(CH$_3$) | — | 3-chloro-6-methoxyphenyl |
| A-538 | CH$_2$—CH$_2$—CH$_2$—CH(CH$_3$) | — | 3,5-dimethylphenyl |
| A-539 | CH$_2$—CH$_2$—CH$_2$—CH(CH$_3$) | — | 2-cyanophenyl |
| A-540 | CH$_2$—CH$_2$—CH$_2$—CH(CH$_3$) | — | 4-chloro-3-trifluoromethylphenyl |
| A-541 | CH$_2$—CH$_2$—CH$_2$—CH(CH$_3$) | — | 3,5-trifluoromethylphenyl |
| A-542 | CH$_2$—CH$_2$—CH$_2$—CH(CH$_3$) | — | 2-methylpyridin-6-yl |
| A-543 | CH$_2$—CH$_2$—CH$_2$—CH(CH$_3$) | — | 3-cyanopyridin-2-yl |
| A-544 | CH$_2$—CH$_2$—CH$_2$—CH(CH$_3$) | — | 3-cyanopyridin-6-yl |
| A-545 | CH$_2$—CH$_2$—CH$_2$—CH(CH$_3$) | — | 3-trifluoromethylpyridin-2-yl |
| A-546 | CH$_2$—CH$_2$—CH$_2$—CH(CH$_3$) | — | 3-trifluoromethylpyridin-6-yl |
| A-547 | CH$_2$—CH$_2$—CH$_2$—CH(CH$_3$) | — | 3-chloro-5-trifluoromethylpyridin-2-yl |
| A-548 | CH$_2$—CH$_2$—CH$_2$—CH(CH$_3$) | — | 3,5-dichloropyridin-4-yl |
| A-549 | CH$_2$—CH$_2$—CH$_2$—CH(CH$_3$) | — | 4-trifluoropyrimidin-2-yl |
| A-550 | CH$_2$—CH$_2$—CH$_2$—CH(CH$_3$) | — | 5-bromopyrimidin-2-yl |
| A-551 | CH$_2$—CH$_2$—CH$_2$—CH(CH$_3$) | — | 5-fluoropyrimidin-2-yl |
| A-552 | CH$_2$—CH$_2$—CH$_2$—CH(CH$_3$) | — | 2-cyanopyridazin-3-yl |
| A-553 | CH$_2$—CH$_2$—CH$_2$—CH(CH$_3$) | — | 5-nitrothiadiazol-2-yl |
| A-554 | CH$_2$—CH$_2$—CH$_2$—CH(CH$_3$) | — | 4-methylthiadiazol-2-yl |
| A-555 | C(O)—CH$_2$—CH$_2$—CH$_2$ | — | 2-methylphenyl |
| A-556 | C(O)—CH$_2$—CH$_2$—CH$_2$ | — | 2-fluorophenyl |
| A-557 | C(O)—CH$_2$—CH$_2$—CH$_2$ | — | 2,3-dimethylphenyl |
| A-558 | C(O)—CH$_2$—CH$_2$—CH$_2$ | — | 2-methoxyphenyl |
| A-559 | C(O)—CH$_2$—CH$_2$—CH$_2$ | — | 2-chlorophenyl |
| A-560 | C(O)—CH$_2$—CH$_2$—CH$_2$ | — | 2-ethoxyphenyl |
| A-561 | C(O)—CH$_2$—CH$_2$—CH$_2$ | — | 3-trifluoromethylphenyl |
| A-562 | C(O)—CH$_2$—CH$_2$—CH$_2$ | — | 2,4-dichlorophenyl |
| A-563 | C(O)—CH$_2$—CH$_2$—CH$_2$ | — | 3,5-dichlorophenyl |
| A-564 | C(O)—CH$_2$—CH$_2$—CH$_2$ | — | 2,3-dichlorophenyl |
| A-565 | C(O)—CH$_2$—CH$_2$—CH$_2$ | — | 3-chloro-6-methoxyphenyl |
| A-566 | C(O)—CH$_2$—CH$_2$—CH$_2$ | — | 3,5-dimethylphenyl |
| A-567 | C(O)—CH$_2$—CH$_2$—CH$_2$ | — | 2-cyanophenyl |
| A-568 | C(O)—CH$_2$—CH$_2$—CH$_2$ | — | 4-chloro-3-trifluoromethylphenyl |
| A-569 | C(O)—CH$_2$—CH$_2$—CH$_2$ | — | 3,5-trifluoromethylphenyl |
| A-570 | C(O)—CH$_2$—CH$_2$—CH$_2$ | — | 2-methylpyridin-6-yl |
| A-571 | C(O)—CH$_2$—CH$_2$—CH$_2$ | — | 3-cyanopyridin-2-yl |
| A-572 | C(O)—CH$_2$—CH$_2$—CH$_2$ | — | 3-cyanopyridin-6-yl |
| A-573 | C(O)—CH$_2$—CH$_2$—CH$_2$ | — | 3-trifluoromethylpyridin-2-yl |
| A-574 | C(O)—CH$_2$—CH$_2$—CH$_2$ | — | 3-trifluoromethylpyridin-6-yl |
| A-575 | C(O)—CH$_2$—CH$_2$—CH$_2$ | — | 3-chloro-5-trifluoromethylpyridin-2-yl |
| A-576 | C(O)—CH$_2$—CH$_2$—CH$_2$ | — | 3,5-dichloropyridin-4-yl |
| A-577 | C(O)—CH$_2$—CH$_2$—CH$_2$ | — | 4-trifluoropyrimidin-2-yl |
| A-578 | C(O)—CH$_2$—CH$_2$—CH$_2$ | — | 5-bromopyrimidin-2-yl |
| A-579 | C(O)—CH$_2$—CH$_2$—CH$_2$ | — | 5-fluoropyrimidin-2-yl |
| A-580 | C(O)—CH$_2$—CH$_2$—CH$_2$ | — | 2-cyanopyridazin-3-yl |
| A-581 | C(O)—CH$_2$—CH$_2$—CH$_2$ | — | 5-nitrothiadiazol-2-yl |
| A-582 | C(O)—CH$_2$—CH$_2$—CH$_2$ | — | 4-methylthiadiazol-2-yl |
| A-583 | C(O)—CH$_2$—CH$_2$—CH$_2$—CH$_2$ | — | 2-methylphenyl |
| A-584 | C(O)—CH$_2$—CH$_2$—CH$_2$—CH$_2$ | — | 2-fluorophenyl |
| A-585 | C(O)—CH$_2$—CH$_2$—CH$_2$—CH$_2$ | — | 2,3-dimethylphenyl |
| A-586 | C(O)—CH$_2$—CH$_2$—CH$_2$—CH$_2$ | — | 2-methoxyphenyl |
| A-587 | C(O)—CH$_2$—CH$_2$—CH$_2$—CH$_2$ | — | 2-chlorophenyl |
| A-588 | C(O)—CH$_2$—CH$_2$—CH$_2$—CH$_2$ | — | 2-ethoxyphenyl |
| A-589 | C(O)—CH$_2$—CH$_2$—CH$_2$—CH$_2$ | — | 3-trifluoromethylphenyl |
| A-590 | C(O)—CH$_2$—CH$_2$—CH$_2$—CH$_2$ | — | 2,4-dichlorophenyl |
| A-591 | C(O)—CH$_2$—CH$_2$—CH$_2$—CH$_2$ | — | 3,5-dichlorophenyl |
| A-592 | C(O)—CH$_2$—CH$_2$—CH$_2$—CH$_2$ | — | 2,3-dichlorophenyl |
| A-593 | C(O)—CH$_2$—CH$_2$—CH$_2$—CH$_2$ | — | 3-chloro-6-methoxyphenyl |
| A-594 | C(O)—CH$_2$—CH$_2$—CH$_2$—CH$_2$ | — | 3,5-dimethylphenyl |

TABLE A-continued (I-Aa.a)

|  | D | E | Rᵃ |
|---|---|---|---|
| A-595 | C(O)—CH₂—CH₂—CH₂—CH₂ | — | 2-cyanophenyl |
| A-596 | C(O)—CH₂—CH₂—CH₂—CH₂ | — | 4-chloro-3-trifluoromethylphenyl |
| A-597 | C(O)—CH₂—CH₂—CH₂—CH₂ | — | 3,5-trifluoromethylphenyl |
| A-598 | C(O)—CH₂—CH₂—CH₂—CH₂ | — | 2-methylpyridin-6-yl |
| A-599 | C(O)—CH₂—CH₂—CH₂—CH₂ | — | 3-cyanopyridin-2-yl |
| A-600 | C(O)—CH₂—CH₂—CH₂—CH₂ | — | 3-cyanopyridin-6-yl |
| A-601 | C(O)—CH₂—CH₂—CH₂—CH₂ | — | 3-trifluoromethylpyridin-2-yl |
| A-602 | C(O)—CH₂—CH₂—CH₂—CH₂ | — | 3-trifluoromethylpyridin-6-yl |
| A-603 | C(O)—CH₂—CH₂—CH₂—CH₂ | — | 3-chloro-5-trifluoromethylpyridin-2-yl |
| A-604 | C(O)—CH₂—CH₂—CH₂—CH₂ | — | 3,5-dichloropyridin-4-yl |
| A-605 | C(O)—CH₂—CH₂—CH₂—CH₂ | — | 4-trifluoropyrimidin-2-yl |
| A-606 | C(O)—CH₂—CH₂—CH₂—CH₂ | — | 5-bromopyrimidin-2-yl |
| A-607 | C(O)—CH₂—CH₂—CH₂—CH₂ | — | 5-fluoropyrimidin-2-yl |
| A-608 | C(O)—CH₂—CH₂—CH₂—CH₂ | — | 2-cyanopyridazin-3-yl |
| A-609 | C(O)—CH₂—CH₂—CH₂—CH₂ | — | 5-nitrothiadiazol-2-yl |
| A-610 | C(O)—CH₂—CH₂—CH₂—CH₂ | — | 4-methylthiadiazol-2-yl |
| A-611 | CH₂—CH₂—CH₂—CH₂ | CH₂ | 3,4-methylphenyl |
| A-612 | CH₂—CH₂—CH₂—CH₂ | CH₂ | 3-piperonyl |
| A-613 | CH₂—CH₂—CH₂—CH₂ | CH₂ | 2,5-bis(methoxy)phenyl |
| A-614 | CH₂—CH₂—CH₂—CH₂ | CH₂ | 3,5-dichlorophenyl |
| A-615 | CH₂—CH₂—CH₂—CH₂ | CH₂ | 3-cyanophenyl |
| A-616 | CH₂—CH₂—CH₂—CH₂ | CH₂ | 4-cyanophenyl |
| A-617 | CH₂—CH₂—CH₂—CH₂ | CH₂ | 2-pyridyl |
| A-618 | CH₂—CH₂—CH₂—CH₂ | CH₂ | 3-pyridyl |
| A-619 | CH₂—CH₂—CH₂—CH₂ | CH₂ | 4-pyridyl |
| A-620 | CH₂—CH₂—CH₂—CH₂ | CH₂ | 2,3-dichlorophenyl |
| A-621 | CH₂—CH₂—CH₂—CH₂ | CH₂ | 2,5-dimethylphenyl |
| A-622 | CH₂—CH₂—CH₂—CH₂ | CH₂ | 2-methylnaphthalen-1-yl |
| A-623 | CH₂—CH₂—CH₂—CH₂ | CH₂ | 2-thienyl |
| A-624 | CH₂—CH₂—CH₂—CH₂ | CCH₃ | phenyl |
| A-625 | trans-CH₂—CH=CH—CH₂ | CH₂ | 3,4-methylphenyl |
| A-626 | trans-CH₂—CH=CH—CH₂ | CH₂ | 3-piperonyl |
| A-627 | trans-CH₂—CH=CH—CH₂ | CH₂ | 2,5-bis(methoxy)phenyl |
| A-628 | trans-CH₂—CH=CH—CH₂ | CH₂ | 3,5-dichlorophenyl |
| A-629 | trans-CH₂—CH=CH—CH₂ | CH₂ | 3-cyanophenyl |
| A-630 | trans-CH₂—CH=CH—CH₂ | CH₂ | 4-cyanophenyl |
| A-631 | trans-CH₂—CH=CH—CH₂ | CH₂ | 2-pyridyl |
| A-632 | trans-CH₂—CH=CH—CH₂ | CH₂ | 3-pyridyl |
| A-633 | trans-CH₂—CH=CH—CH₂ | CH₂ | 4-pyridyl |
| A-634 | trans-CH₂—CH=CH—CH₂ | CH₂ | 2,3-dichlorophenyl |
| A-635 | trans-CH₂—CH=CH—CH₂ | CH₂ | 2,5-dimethylphenyl |
| A-636 | trans-CH₂—CH=CH—CH₂ | CH₂ | 2-methylnaphthalen-1-yl |
| A-637 | trans-CH₂—CH=CH—CH₂ | CH₂ | 2-thienyl |
| A-638 | trans-CH₂—CH=CH—CH₂ | CCH₃ | phenyl |
| A-639 | trans-CH₂—C(CH₃)=CH—CH₂ | CH₂ | 3,4-methylphenyl |
| A-640 | trans-CH₂—C(CH₃)=CH—CH₂ | CH₂ | 3-piperonyl |
| A-641 | trans-CH₂—C(CH₃)=CH—CH₂ | CH₂ | 2,5-bis(methoxy)phenyl |
| A-642 | trans-CH₂—C(CH₃)=CH—CH₂ | CH₂ | 3,5-dichlorophenyl |
| A-643 | trans-CH₂—C(CH₃)=CH—CH₂ | CH₂ | 3-cyanophenyl |
| A-644 | trans-CH₂—C(CH₃)=CH—CH₂ | CH₂ | 4-cyanophenyl |
| A-645 | trans-CH₂—C(CH₃)=CH—CH₂ | CH₂ | 2-pyridyl |
| A-646 | trans-CH₂—C(CH₃)=CH—CH₂ | CH₂ | 3-pyridyl |
| A-647 | trans-CH₂—C(CH₃)=CH—CH₂ | CH₂ | 4-pyridyl |
| A-648 | trans-CH₂—C(CH₃)=CH—CH₂ | CH₂ | 2,3-dichlorophenyl |
| A-649 | trans-CH₂—C(CH₃)=CH—CH₂ | CH₂ | 2,5-dimethylphenyl |
| A-650 | trans-CH₂—C(CH₃)=CH—CH₂ | CH₂ | 2-methylnaphthalen-1-yl |
| A-651 | trans-CH₂—C(CH₃)=CH—CH₂ | CH₂ | 2-thienyl |
| A-652 | trans-CH₂—C(CH₃)=CH—CH₂ | CCH₃ | phenyl |
| A-653 | CH₂—CH(CH₃)—CH₂—CH₂ | CH₂ | 3,4-methylphenyl |
| A-654 | CH₂—CH(CH₃)—CH₂—CH₂ | CH₂ | 3-piperonyl |
| A-655 | CH₂—CH(CH₃)—CH₂—CH₂ | CH₂ | 2,5-bis(methoxy)phenyl |
| A-656 | CH₂—CH(CH₃)—CH₂—CH₂ | CH₂ | 3,5-dichlorophenyl |
| A-657 | CH₂—CH(CH₃)—CH₂—CH₂ | CH₂ | 3-cyanophenyl |
| A-658 | CH₂—CH(CH₃)—CH₂—CH₂ | CH₂ | 4-cyanophenyl |
| A-659 | CH₂—CH(CH₃)—CH₂—CH₂ | CH₂ | 2-pyridyl |
| A-660 | CH₂—CH(CH₃)—CH₂—CH₂ | CH₂ | 3-pyridyl |

TABLE A-continued (I-Aa.a)

| | D | E | R$^a$ |
|---|---|---|---|
| A-661 | CH$_2$—CH(CH$_3$)—CH$_2$—CH$_2$ | CH$_2$ | 4-pyridyl |
| A-662 | CH$_2$—CH(CH$_3$)—CH$_2$—CH$_2$ | CH$_2$ | 2,3-dichlorophenyl |
| A-663 | CH$_2$—CH(CH$_3$)—CH$_2$—CH$_2$ | CH$_2$ | 2,5-dimethylphenyl |
| A-664 | CH$_2$—CH(CH$_3$)—CH$_2$—CH$_2$ | CH$_2$ | 2-methylnaphthalen-1-yl |
| A-665 | CH$_2$—CH(CH$_3$)—CH$_2$—CH$_2$ | CH$_2$ | 2-thienyl |
| A-666 | CH$_2$—CH(CH$_3$)—CH$_2$—CH$_2$ | CCH$_3$ | phenyl |
| A-667 | CH$_2$—CH$_2$—CH$_2$—CH(CH$_3$) | CH$_2$ | 3,4-methylphenyl |
| A-668 | CH$_2$—CH$_2$—CH$_2$—CH(CH$_3$) | CH$_2$ | 3-piperonyl |
| A-669 | CH$_2$—CH$_2$—CH$_2$—CH(CH$_3$) | CH$_2$ | 2,5-bis(methoxy)phenyl |
| A-670 | CH$_2$—CH$_2$—CH$_2$—CH(CH$_3$) | CH$_2$ | 3,5-dichlorophenyl |
| A-671 | CH$_2$—CH$_2$—CH$_2$—CH(CH$_3$) | CH$_2$ | 3-cyanophenyl |
| A-672 | CH$_2$—CH$_2$—CH$_2$—CH(CH$_3$) | CH$_2$ | 4-cyanophenyl |
| A-673 | CH$_2$—CH$_2$—CH$_2$—CH(CH$_3$) | CH$_2$ | 2-pyridyl |
| A-674 | CH$_2$—CH$_2$—CH$_2$—CH(CH$_3$) | CH$_2$ | 3-pyridyl |
| A-675 | CH$_2$—CH$_2$—CH$_2$—CH(CH$_3$) | CH$_2$ | 4-pyridyl |
| A-676 | CH$_2$—CH$_2$—CH$_2$—CH(CH$_3$) | CH$_2$ | 2,3-dichlorophenyl |
| A-677 | CH$_2$—CH$_2$—CH$_2$—CH(CH$_3$) | CH$_2$ | 2,5-dimethylphenyl |
| A-678 | CH$_2$—CH$_2$—CH$_2$—CH(CH$_3$) | CH$_2$ | 2-methylnaphthalen-1-yl |
| A-679 | CH$_2$—CH$_2$—CH$_2$—CH(CH$_3$) | CH$_2$ | 2-thienyl |
| A-680 | CH$_2$—CH$_2$—CH$_2$—CH(CH$_3$) | CCH$_3$ | phenyl |
| A-681 | C(O)—CH$_2$—CH$_2$—CH$_2$ | CH$_2$ | 3,4-methylphenyl |
| A-682 | C(O)—CH$_2$—CH$_2$—CH$_2$ | CH$_2$ | 3-piperonyl |
| A-683 | C(O)—CH$_2$—CH$_2$—CH$_2$ | CH$_2$ | 2,5-bis(methoxy)phenyl |
| A-684 | C(O)—CH$_2$—CH$_2$—CH$_2$ | CH$_2$ | 3,5-dichlorophenyl |
| A-685 | C(O)—CH$_2$—CH$_2$—CH$_2$ | CH$_2$ | 3-cyanophenyl |
| A-686 | C(O)—CH$_2$—CH$_2$—CH$_2$ | CH$_2$ | 4-cyanophenyl |
| A-687 | C(O)—CH$_2$—CH$_2$—CH$_2$ | CH$_2$ | 2-pyridyl |
| A-688 | C(O)—CH$_2$—CH$_2$—CH$_2$ | CH$_2$ | 3-pyridyl |
| A-689 | C(O)—CH$_2$—CH$_2$—CH$_2$ | CH$_2$ | 4-pyridyl |
| A-690 | C(O)—CH$_2$—CH$_2$—CH$_2$ | CH$_2$ | 2,3-dichlorophenyl |
| A-691 | C(O)—CH$_2$—CH$_2$—CH$_2$ | CH$_2$ | 2,5-dimethylphenyl |
| A-692 | C(O)—CH$_2$—CH$_2$—CH$_2$ | CH$_2$ | 2-methylnaphthalen-1-yl |
| A-693 | C(O)—CH$_2$—CH$_2$—CH$_2$ | CH$_2$ | 2-thienyl |
| A-694 | C(O)—CH$_2$—CH$_2$—CH$_2$ | CCH$_3$ | phenyl |
| A-695 | C(O)—CH$_2$—CH$_2$—CH$_2$—CH$_2$ | CH$_2$ | 3,4-methylphenyl |
| A-696 | C(O)—CH$_2$—CH$_2$—CH$_2$—CH$_2$ | CH$_2$ | 3-piperonyl |
| A-697 | C(O)—CH$_2$—CH$_2$—CH$_2$—CH$_2$ | CH$_2$ | 2,5-bis(methoxy)phenyl |
| A-698 | C(O)—CH$_2$—CH$_2$—CH$_2$—CH$_2$ | CH$_2$ | 3,5-dichlorophenyl |
| A-699 | C(O)—CH$_2$—CH$_2$—CH$_2$—CH$_2$ | CH$_2$ | 3-cyanophenyl |
| A-700 | C(O)—CH$_2$—CH$_2$—CH$_2$—CH$_2$ | CH$_2$ | 4-cyanophenyl |
| A-701 | C(O)—CH$_2$—CH$_2$—CH$_2$—CH$_2$ | CH$_2$ | 2-pyridyl |
| A-702 | C(O)—CH$_2$—CH$_2$—CH$_2$—CH$_2$ | CH$_2$ | 3-pyridyl |
| A-703 | C(O)—CH$_2$—CH$_2$—CH$_2$—CH$_2$ | CH$_2$ | 4-pyridyl |
| A-704 | C(O)—CH$_2$—CH$_2$—CH$_2$—CH$_2$ | CH$_2$ | 2,3-dichlorophenyl |
| A-705 | C(O)—CH$_2$—CH$_2$—CH$_2$—CH$_2$ | CH$_2$ | 2,5-dimethylphenyl |
| A-706 | C(O)—CH$_2$—CH$_2$—CH$_2$—CH$_2$ | CH$_2$ | 2-methylnaphthalen-1-yl |
| A-707 | C(O)—CH$_2$—CH$_2$—CH$_2$—CH$_2$ | CH$_2$ | 2-thienyl |
| A-708 | C(O)—CH$_2$—CH$_2$—CH$_2$—CH$_2$ | CCH$_3$ | phenyl |

Particular preference is further given to the compounds of the formula I-Aa.b where the variables D, E and Ar are each as defined above, in particular as defined above with preference. Examples of such compounds are the compounds I-Aa.b.1 to I-Aa.b.708 in which the variables D, E and Ar together are each as defined in one line of Table A.

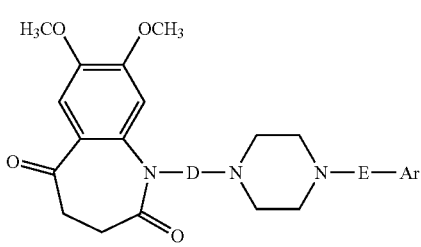
(I-Aa.b)

Particular preference is further given to the compounds of the formula I-Ba.a where the variables D, E and Ar are each as defined above, in particular as defined above with preference. Examples of such compounds are the compounds I-Ba.a.1 to I-Ba.a.708, in which the variables D, E and Ar together are each as defined in one line of Table A.

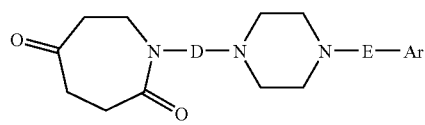
(I-Ba.a)

Particular preference is further given to the compounds of the formula I-Aa.c where the variables D, E and Ar are each as defined above, in particular as defined above with preference. Examples of such compounds are the compounds I-Aa.c.1 to I-Aa.c.708, in which the variables D, E and Ar together are each as defined in one line of Table A.

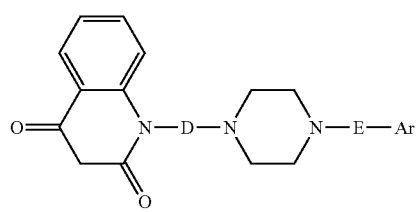
(I-Aa.c)

Preference is further given to the compounds of the formulae I-Aa.d and I-Aa.e where the variables D, E and Ar are each as defined above, in particular as defined above with preference. Examples of such compounds are the compounds I-Aa.d.1 to I-Aa.d.708 and the compounds I-Aa.e.1 to I-Aa.e.708 in which the variables D, E and Ar in each case together are as defined in one line of Table A.

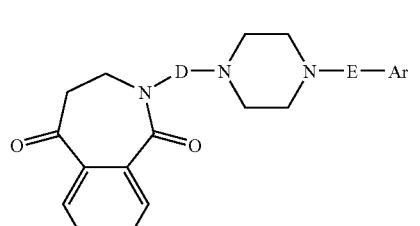
(I-Aa.d)

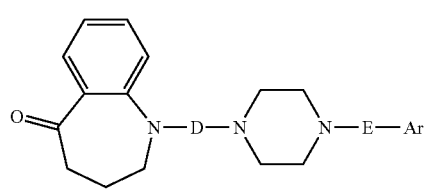
(I-Aa.e)

Preference is further given to the compounds of the formulae I-Aa.f, I-Aa.g, I-Aa.h, I-Aa.i, I-Aa.k and I-Ba.b, where the variables D and $R^{aa}$ are each as defined above, in particular as defined above with preference. Examples of such compounds are the compounds I-Aa.f.1 to I-Aa.f.98, I-Aa.g.1 to I-Aa.g.98, I-Aa.h.1 to I-Aa.h.98, I-Aa.i.1 to I-Aa.i.98, I-Aa.k.1 to I-Aa.k.98 and the compounds I-Ba.b.1 to I-Ba.b.98, in which the variables D and $R^{aa}$ in each case together are as defined in one line of Table B.

TABLE B

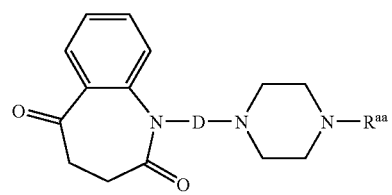
(I-Aa.f)

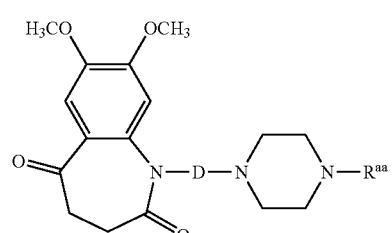
(I-Aa.g)

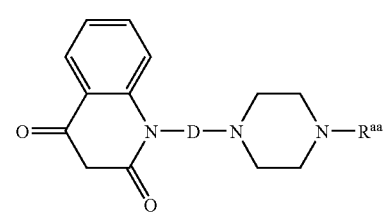
(I-Aa.h)

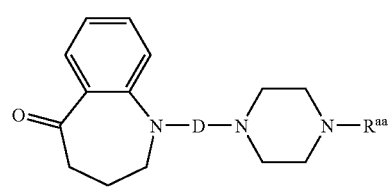
(I-Aa.i)

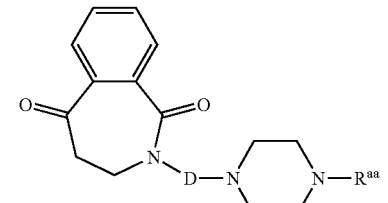
(I-Aa.k)

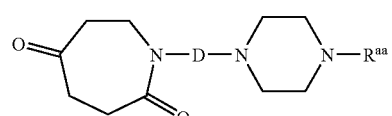
(I-Ba.b)

| | D | $R^{aa}$ |
|---|---|---|
| B-1 | $CH_2-CH_2-CH_2-CH_2$ | $CH_2$-cyclohexyl |
| B-2 | $CH_2-CH_2-CH_2-CH_2$ | $CH_2-CH=CH_2$ |
| B-3 | $CH_2-CH_2-CH_2-CH_2$ | pyrrolidin-1-ylcarbonylmethyl |

TABLE B-continued (I-Aa.f)
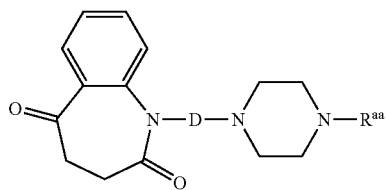

(I-Aa.g)
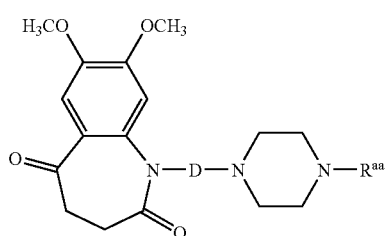

(I-Aa.h)
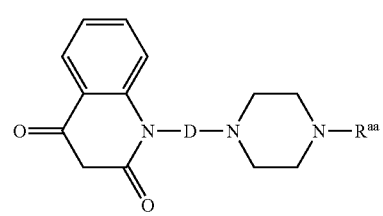

(I-Aa.i)
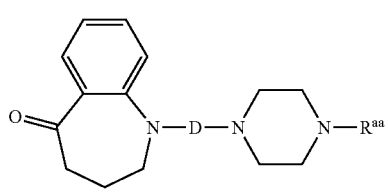

(I-Aa.k)
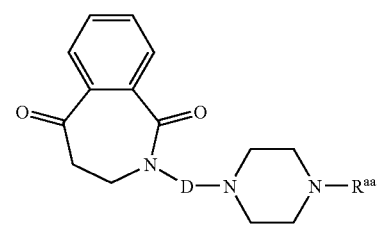

(I-Ba.b)
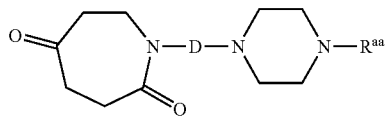

| | D | $R^{aa}$ |
|---|---|---|
| B-4 | CH₂—CH₂—CH₂—CH₂ | acetyl |
| B-5 | CH₂—CH₂—CH₂—CH₂ | CH₂CH₂-cyclohexyl |
| B-6 | CH₂—CH₂—CH₂—CH₂ | cyclopentyl |
| B-7 | CH₂—CH₂—CH₂—CH₂ | cyclohexyl |
| B-8 | CH₂—CH₂—CH₂—CH₂ | piperazin-1-ylcarbonylmethyl |
| B-9 | CH₂—CH₂—CH₂—CH₂ | cyclopropylcarbonyl |
| B-10 | CH₂—CH₂—CH₂—CH₂ | oxolan-2-ylcarbonyl |
| B-11 | CH₂—CH₂—CH₂—CH₂ | oxolan-2-ylmethyl |
| B-12 | CH₂—CH₂—CH₂—CH₂ | methyl |
| B-13 | CH₂—CH₂—CH₂—CH₂ | ethyl |
| B-14 | CH₂—CH₂—CH₂—CH₂ | n-propyl |
| B-15 | trans-CH₂—CH=CH—CH₂ | CH₂-cyclohexyl |

TABLE B-continued (I-Aa.f)
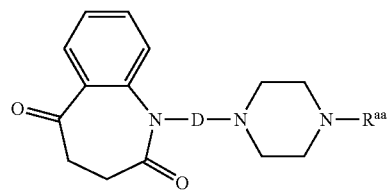

(I-Aa.g)
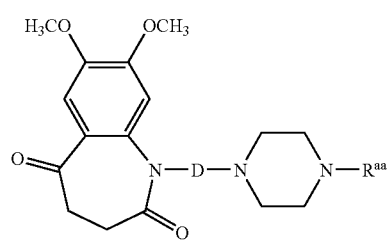

(I-Aa.h)
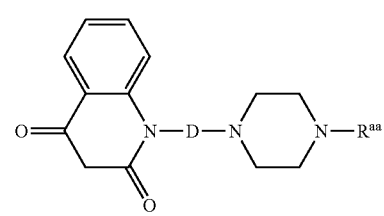

(I-Aa.i)
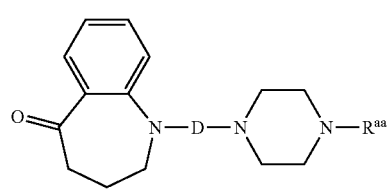

(I-Aa.k)
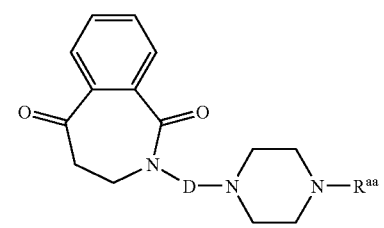

(I-Ba.b)
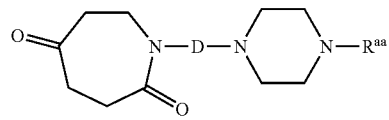

| | D | $R^{aa}$ |
|---|---|---|
| B-16 | trans-CH₂—CH=CH—CH₂ | CH₂—CH=CH₂ |
| B-17 | trans-CH₂—CH=CH—CH₂ | pyrrolidin-1-ylcarbonylmethyl |
| B-18 | trans-CH₂—CH=CH—CH₂ | acetyl |
| B-19 | trans-CH₂—CH=CH—CH₂ | CH₂CH₂-cyclohexyl |
| B-20 | trans-CH₂—CH=CH—CH₂ | cyclopentyl |
| B-21 | trans-CH₂—CH=CH—CH₂ | cyclohexyl |
| B-22 | trans-CH₂—CH=CH—CH₂ | piperazin-1-ylcarbonylmethyl |
| B-23 | trans-CH₂—CH=CH—CH₂ | cyclopropylcarbonyl |
| B-24 | trans-CH₂—CH=CH—CH₂ | oxolan-2-ylcarbonyl |
| B-25 | trans-CH₂—CH=CH—CH₂ | oxolan-2-ylmethyl |
| B-26 | trans-CH₂—CH=CH—CH₂ | methyl |
| B-27 | trans-CH₂—CH=CH—CH₂ | ethyl |

TABLE B-continued

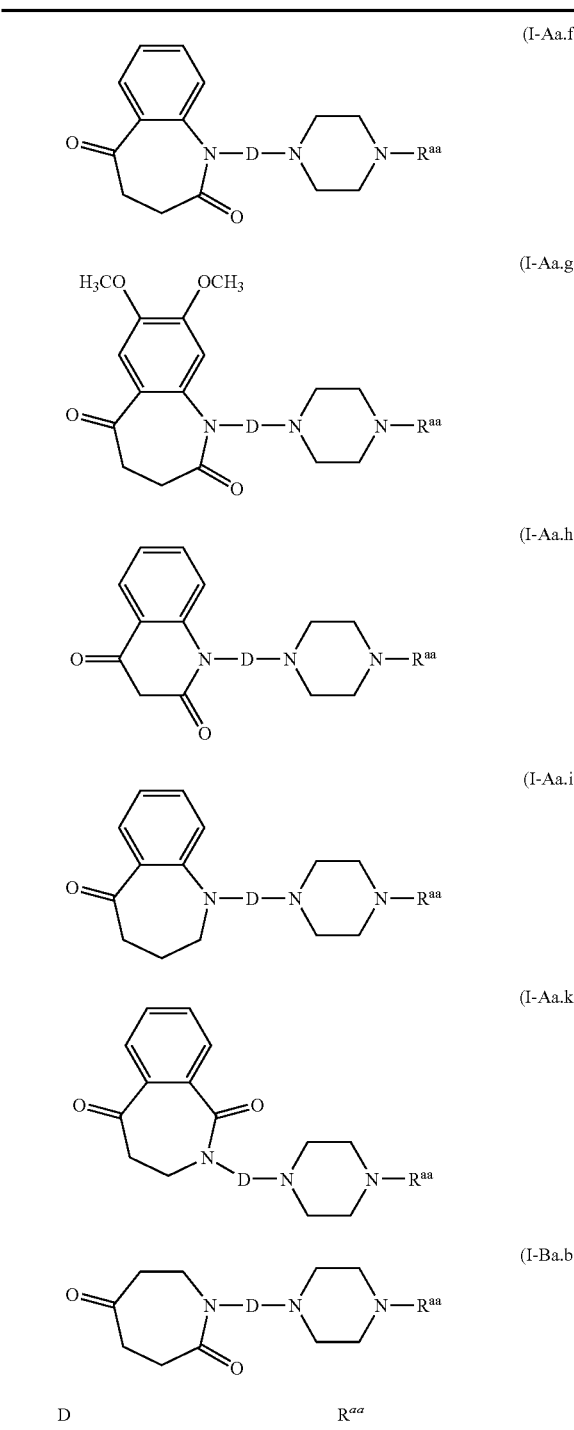

(I-Aa.f)
(I-Aa.g)
(I-Aa.h)
(I-Aa.i)
(I-Aa.k)
(I-Ba.b)

| | D | R$^{aa}$ |
|---|---|---|
| B-28 | trans-CH$_2$—CH=CH—CH$_2$ | n-propyl |
| B-29 | trans-CH$_2$—C(CH$_3$)=CH—CH$_2$ | CH$_2$-cyclohexyl |
| B-30 | trans-CH$_2$—C(CH$_3$)=CH—CH$_2$ | CH$_2$—CH=CH$_2$ |
| B-31 | trans-CH$_2$—C(CH$_3$)=CH—CH$_2$ | pyrrolidin-1-ylcarbonylmethyl |
| B-32 | trans-CH$_2$—C(CH$_3$)=CH—CH$_2$ | acetyl |
| B-33 | trans-CH$_2$—C(CH$_3$)=CH—CH$_2$ | CH$_2$CH$_2$-cyclohexyl |
| B-34 | trans-CH$_2$—C(CH$_3$)=CH—CH$_2$ | cyclopentyl |
| B-35 | trans-CH$_2$—C(CH$_3$)=CH—CH$_2$ | cyclohexyl |
| B-36 | trans-CH$_2$—C(CH$_3$)=CH—CH$_2$ | piperazin-1-ylcarbonylmethyl |
| B-37 | trans-CH$_2$—C(CH$_3$)=CH—CH$_2$ | cyclopropylcarbonyl |
| B-38 | trans-CH$_2$—C(CH$_3$)=CH—CH$_2$ | oxolan-2-ylcarbonyl |
| B-39 | trans-CH$_2$—C(CH$_3$)=CH—CH$_2$ | oxolan-2-ylmethyl |

TABLE B-continued

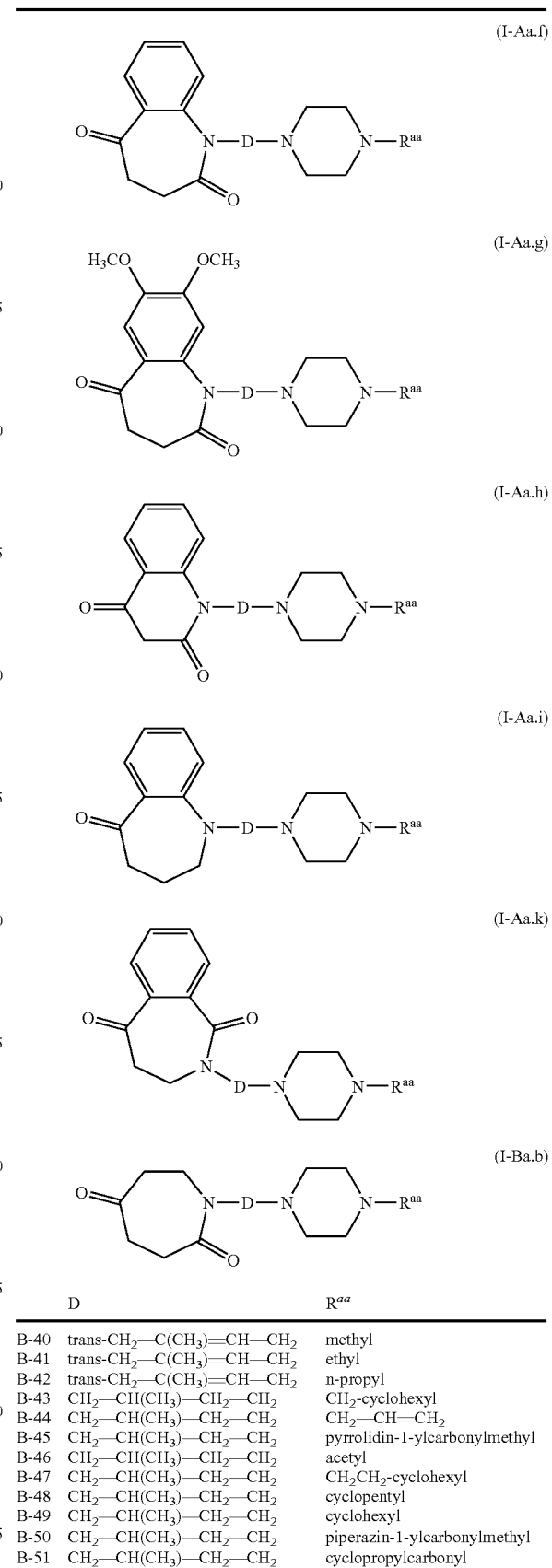

(I-Aa.f)
(I-Aa.g)
(I-Aa.h)
(I-Aa.i)
(I-Aa.k)
(I-Ba.b)

| | D | R$^{aa}$ |
|---|---|---|
| B-40 | trans-CH$_2$—C(CH$_3$)=CH—CH$_2$ | methyl |
| B-41 | trans-CH$_2$—C(CH$_3$)=CH—CH$_2$ | ethyl |
| B-42 | trans-CH$_2$—C(CH$_3$)=CH—CH$_2$ | n-propyl |
| B-43 | CH$_2$—CH(CH$_3$)—CH$_2$—CH$_2$ | CH$_2$-cyclohexyl |
| B-44 | CH$_2$—CH(CH$_3$)—CH$_2$—CH$_2$ | CH$_2$—CH=CH$_2$ |
| B-45 | CH$_2$—CH(CH$_3$)—CH$_2$—CH$_2$ | pyrrolidin-1-ylcarbonylmethyl |
| B-46 | CH$_2$—CH(CH$_3$)—CH$_2$—CH$_2$ | acetyl |
| B-47 | CH$_2$—CH(CH$_3$)—CH$_2$—CH$_2$ | CH$_2$CH$_2$-cyclohexyl |
| B-48 | CH$_2$—CH(CH$_3$)—CH$_2$—CH$_2$ | cyclopentyl |
| B-49 | CH$_2$—CH(CH$_3$)—CH$_2$—CH$_2$ | cyclohexyl |
| B-50 | CH$_2$—CH(CH$_3$)—CH$_2$—CH$_2$ | piperazin-1-ylcarbonylmethyl |
| B-51 | CH$_2$—CH(CH$_3$)—CH$_2$—CH$_2$ | cyclopropylcarbonyl |

TABLE B-continued

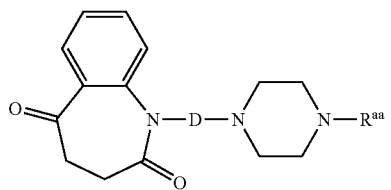
(I-Aa.f)

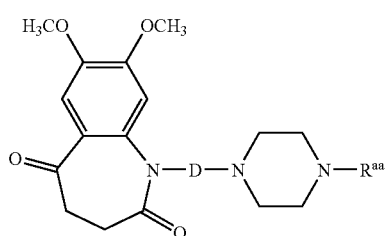
(I-Aa.g)

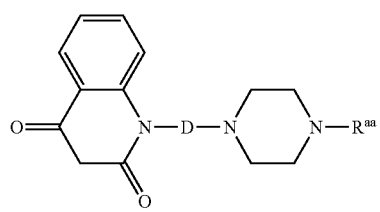
(I-Aa.h)

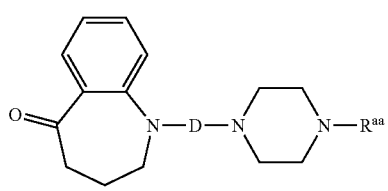
(I-Aa.i)

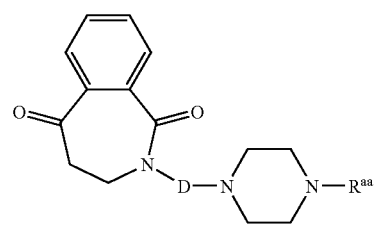
(I-Aa.k)

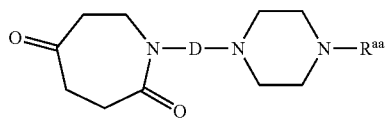
(I-Ba.b)

| | D | $R^{aa}$ |
|---|---|---|
| B-52 | $CH_2$—$CH(CH_3)$—$CH_2$—$CH_2$ | oxolan-2-ylcarbonyl |
| B-53 | $CH_2$—$CH(CH_3)$—$CH_2$—$CH_2$ | oxolan-2-ylmethyl |
| B-54 | $CH_2$—$CH(CH_3)$—$CH_2$—$CH_2$ | methyl |
| B-55 | $CH_2$—$CH(CH_3)$—$CH_2$—$CH_2$ | ethyl |
| B-56 | $CH_2$—$CH(CH_3)$—$CH_2$—$CH_2$ | n-propyl |
| B-57 | $CH_2$—$CH_2$—$CH_2$—$CH(CH_3)$ | $CH_2$-cyclohexyl |
| B-58 | $CH_2$—$CH_2$—$CH_2$—$CH(CH_3)$ | $CH_2$—CH═$CH_2$ |
| B-59 | $CH_2$—$CH_2$—$CH_2$—$CH(CH_3)$ | pyrrolidin-1-ylcarbonylmethyl |
| B-60 | $CH_2$—$CH_2$—$CH_2$—$CH(CH_3)$ | acetyl |
| B-61 | $CH_2$—$CH_2$—$CH_2$—$CH(CH_3)$ | $CH_2CH_2$-cyclohexyl |
| B-62 | $CH_2$—$CH_2$—$CH_2$—$CH(CH_3)$ | cyclopentyl |
| B-63 | $CH_2$—$CH_2$—$CH_2$—$CH(CH_3)$ | cyclohexyl |

TABLE B-continued

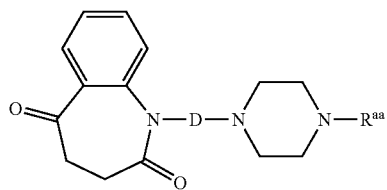
(I-Aa.f)

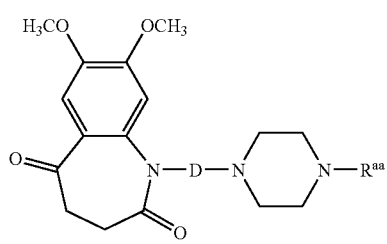
(I-Aa.g)

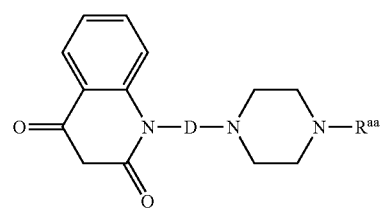
(I-Aa.h)

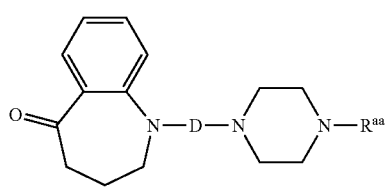
(I-Aa.i)

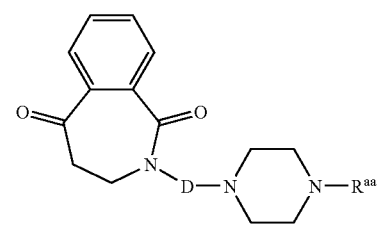
(I-Aa.k)

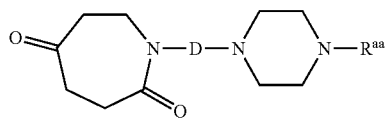
(I-Ba.b)

| | D | $R^{aa}$ |
|---|---|---|
| B-64 | $CH_2$—$CH_2$—$CH_2$—$CH(CH_3)$ | piperazin-1-ylcarbonylmethyl |
| B-65 | $CH_2$—$CH_2$—$CH_2$—$CH(CH_3)$ | cyclopropylcarbonyl |
| B-66 | $CH_2$—$CH_2$—$CH_2$—$CH(CH_3)$ | oxolan-2-ylcarbonyl |
| B-67 | $CH_2$—$CH_2$—$CH_2$—$CH(CH_3)$ | oxolan-2-ylmethyl |
| B-68 | $CH_2$—$CH_2$—$CH_2$—$CH(CH_3)$ | methyl |
| B-69 | $CH_2$—$CH_2$—$CH_2$—$CH(CH_3)$ | ethyl |
| B-70 | $CH_2$—$CH_2$—$CH_2$—$CH(CH_3)$ | n-propyl |
| B-71 | $C(O)$—$CH_2$—$CH_2$—$CH_2$ | $CH_2$-cyclohexyl |
| B-72 | $C(O)$—$CH_2$—$CH_2$—$CH_2$ | $CH_2$—CH═$CH_2$ |
| B-73 | $C(O)$—$CH_2$—$CH_2$—$CH_2$ | pyrrolidin-1-ylcarbonylmethyl |
| B-74 | $C(O)$—$CH_2$—$CH_2$—$CH_2$ | acetyl |
| B-75 | $C(O)$—$CH_2$—$CH_2$—$CH_2$ | $CH_2CH_2$-cyclohexyl |

TABLE B-continued

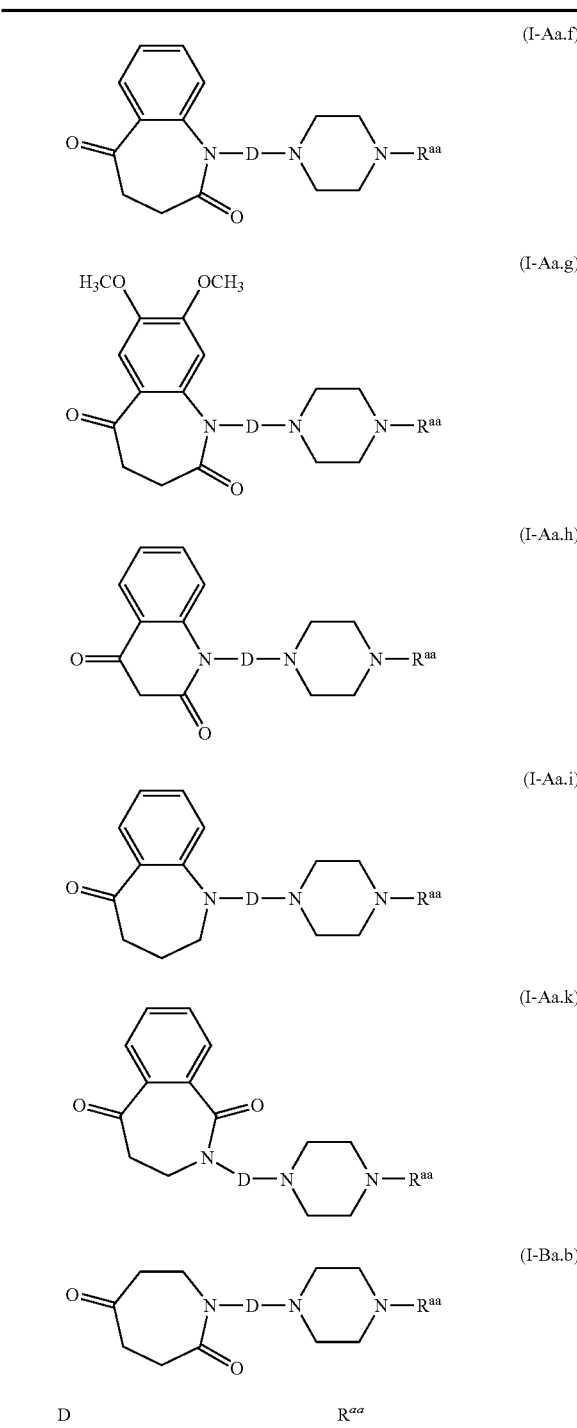

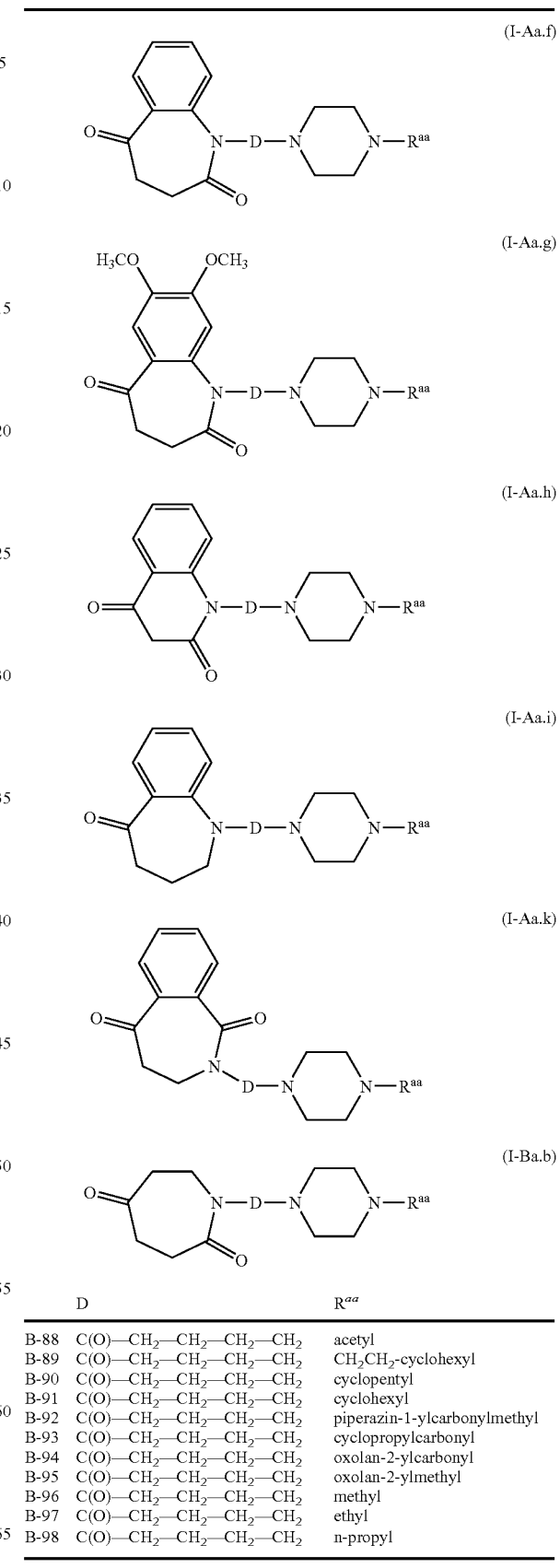

| | D | R$^{aa}$ |
|---|---|---|
| B-76 | C(O)—CH$_2$—CH$_2$—CH$_2$ | cyclopentyl |
| B-77 | C(O)—CH$_2$—CH$_2$—CH$_2$ | cyclohexyl |
| B-78 | C(O)—CH$_2$—CH$_2$—CH$_2$ | piperazin-1-ylcarbonylmethyl |
| B-79 | C(O)—CH$_2$—CH$_2$—CH$_2$ | cyclopropylcarbonyl |
| B-80 | C(O)—CH$_2$—CH$_2$—CH$_2$ | oxolan-2-ylcarbonyl |
| B-81 | C(O)—CH$_2$—CH$_2$—CH$_2$ | oxolan-2-ylmethyl |
| B-82 | C(O)—CH$_2$—CH$_2$—CH$_2$ | methyl |
| B-83 | C(O)—CH$_2$—CH$_2$—CH$_2$ | ethyl |
| B-84 | C(O)—CH$_2$—CH$_2$—CH$_2$ | n-propyl |
| B-85 | C(O)—CH$_2$—CH$_2$—CH$_2$—CH$_2$ | CH$_2$-cyclohexyl |
| B-86 | C(O)—CH$_2$—CH$_2$—CH$_2$—CH$_2$ | CH$_2$—CH=CH$_2$ |
| B-87 | C(O)—CH$_2$—CH$_2$—CH$_2$—CH$_2$ | pyrrolidin-1-ylcarbonylmethyl |
| B-88 | C(O)—CH$_2$—CH$_2$—CH$_2$—CH$_2$ | acetyl |
| B-89 | C(O)—CH$_2$—CH$_2$—CH$_2$—CH$_2$ | CH$_2$CH$_2$-cyclohexyl |
| B-90 | C(O)—CH$_2$—CH$_2$—CH$_2$—CH$_2$ | cyclopentyl |
| B-91 | C(O)—CH$_2$—CH$_2$—CH$_2$—CH$_2$ | cyclohexyl |
| B-92 | C(O)—CH$_2$—CH$_2$—CH$_2$—CH$_2$ | piperazin-1-ylcarbonylmethyl |
| B-93 | C(O)—CH$_2$—CH$_2$—CH$_2$—CH$_2$ | cyclopropylcarbonyl |
| B-94 | C(O)—CH$_2$—CH$_2$—CH$_2$—CH$_2$ | oxolan-2-ylcarbonyl |
| B-95 | C(O)—CH$_2$—CH$_2$—CH$_2$—CH$_2$ | oxolan-2-ylmethyl |
| B-96 | C(O)—CH$_2$—CH$_2$—CH$_2$—CH$_2$ | methyl |
| B-97 | C(O)—CH$_2$—CH$_2$—CH$_2$—CH$_2$ | ethyl |
| B-98 | C(O)—CH$_2$—CH$_2$—CH$_2$—CH$_2$ | n-propyl |

The inventive compounds I can be prepared in analogy to the prior art cited at the outset and by known processes for preparing keto lactams. An important route to the inventive compounds is shown in scheme 1.

Scheme 1:

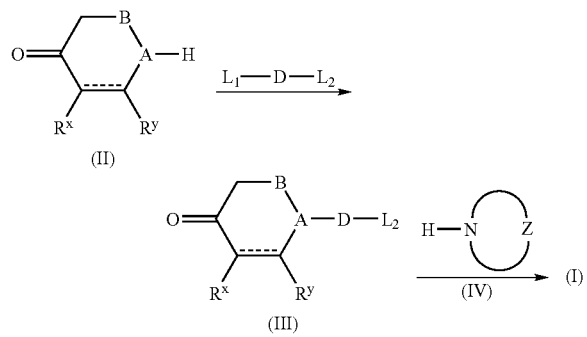

In scheme 1, A, B, D, $R^x$, $R^y$ and NZ are each as defined above. $L_1$ and $L_2$ are each nucleophilically displaceable leaving groups. Examples of suitable nucleophilically displaceable leaving groups are halogen, in particular chlorine, bromine or iodine, alkyl- and arylsulfonate such as mesylate, tosylate. $L_1$ and $L_2$ are preferably different from one another and have different reactivity. For example, $L_1$ is bromine or iodine and $L_2$ is chlorine. The reaction conditions required for the reaction correspond to the reaction conditions customary for nucleophilic substitutions. When D is a C(O)alkylene group, $L_1$ is in particular halogen and especially chlorine.

Compounds of the general formula IV are either known from the literature, for example from WO 96/02519, WO 97/25324, WO 99/02503, WO 00/42036, DE 10304870.7 or the literature cited in these documents, or can be prepared by the processes described there.

The compounds of the formula II are likewise known and some are commercially available or can be prepared in analogy to known processes, as described, for example, in: J. Am. Chem. Soc. 1958, 80, p. 2172-2178; J. Chem. Soc. 1959, p. 3111; J. Chem. Soc. 1934, p. 1326; Heterocycles 1977, 8, p. 345-350; Tetrahedron Lett. 1993, 34, 5855; Arch. Pharm. 1991, 324, 579; J. Med. Chem. 1990, 33, 633; J. Med. Chem. 2000, 43, 1878; J. Org. Chem. 1972, 37, p. 2849, Monatsh. Chem. 1965, 96, 418, Synlett 2002, 8, p. 1350, Tetrahedron Lett, 1993, 34, p. 5855 and J. Photochem. 28 (1985) p. 69-70.

Some of the inventive compounds can also be prepared by the synthesis shown in scheme 2:

Scheme 2:

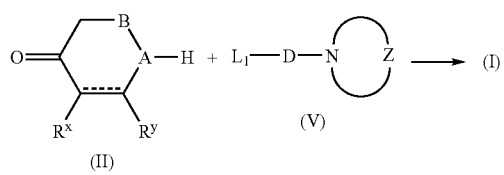

In scheme 2, A, B, $R^x$, $R^y$ and NZ are each as defined above. D is $C_2$-$C_3$-alkylene or a CO—$C_2$-$C_{10}$-alkylene group where CO is bonded to $L_1$. $L_1$ is a nucleophilically displaceable leaving group. For example, $L_1$ is chlorine, bromine or iodine when D is alkylene. The reaction conditions required for the reaction correspond to the reaction conditions customary for nucleophilic substitutions. When D is a C(O)alkylene group, $L_1$ is in particular halogen and especially chlorine.

Compounds of the general formula V are likewise known from the literature, for example from WO 96/02519, WO 97/25324, WO 99/02503, WO 00/42036, DE 10304870.7, or from the literature cited in these documents, or can be prepared by the processes described there, for example by reacting a compound of the formula IV shown in scheme 1 with a compound $L_1$-D-$L_2$ where L and D are each as defined in scheme 1.

Compounds of the formula I where

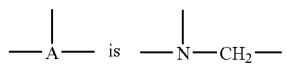

may also be prepared by reducing compounds of the formula I where

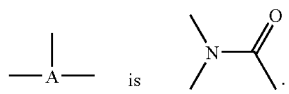

Suitable reducing agents include, for example, aluminum hydrides such as lithium aluminum hydride. Suitable methods for this purpose are known from the prior art, for example from J. Org. Chem. 1972, 37, p. 2849 and can be used analogously for this reaction.

The tautomers I' can be prepared analogously to the preparation of the compound I described here. For example, the tautomers I' can be prepared by the synthesis route shown in scheme 1. The compounds I' where R is alkoxy or an OC(O) $R^9$ group can also be prepared from the compounds I by reacting with a suitable alkylating agent or a suitable acylating agent of the formula X'—C(O)$R^9$ where X' is halogen and in particular chlorine, optionally in the presence of an auxiliary base, for example by the methods described in Chem. Commun. 1998, p. 2621 or J. Org. Chem. 1959, 24, p. 41-43. The compound I can also be converted to its tautomers I' where R=halogen by treating them with a suitable halogenating agent such as $PCl_3$ or $POCl_3$.

Unless stated otherwise, the above-described reactions are generally effected in a solvent at temperatures between room temperature and the boiling point of the solvent used. Usable solvents are, for example, ethers such as diethyl ether, diisopropyl ether, methyl tert-butyl ether or tetrahydrofuran, dimethylformamide, dimethyl sulfoxide, dimethoxyethane, toluene, xylene, acetonitrile, ketones such as acetone or methyl ethyl ketone, or alcohols such as methanol, ethanol or butanol.

If desired, it is possible to work in the presence of a base for neutralization of protons released in the reactions. Suitable bases include inorganic bases such as sodium carbonate or potassium carbonate, sodium hydrogencarbonate or potassium hydrogencarbonate, and also alkoxides such as sodium methoxide, sodium ethoxide, alkali metal hydrides such as sodium hydride, organometallic compounds such as butyllithium or alkylmagnesium compounds, or organic nitrogen bases such as triethylamine or pyridine. The latter can simultaneously also serve as solvents.

The crude product is isolated in a customary manner, for example by filtration, distilling off the solvent or extraction from the reaction mixture, etc. The resulting compounds can be purified in a customary manner, for example by recrystallization from a solvent, chromatography or by conversion to an acid addition salt.

The acid addition salts are typically prepared by mixing the free base with the corresponding acid, optionally in a solution in an organic solvent, for example a low molecular weight alcohol such as methanol, ethanol or propanol, an ether such as methyl tertbutyl ether, diisopropyl ether, a ketone such as acetone or methyl ethyl ketone, or an ester such as ethyl acetate.

The inventive compounds of the formula I are generally highly selective dopamine $D_3$ receptor ligands which, because of their low affinity for other receptors such as $D_1$ receptors, $D_4$ receptors, $\alpha 1$- and/or $\alpha 2$-adrenergic receptors, muscarinergic receptors, histaminic receptors, opiate receptors and, in particular, for dopamine $D_2$ receptors, have fewer side effects than classical neuroleptics which comprise $D_2$ receptor antagonists.

The high affinity of the inventive compounds for $D_3$ receptors is reflected in very low in vitro $K_i$ values of ordinarily less than 100 nM (nmol/l) and especially of less than 50 nM. Binding affinities for $D_3$ receptors can, for example, be determined via the displacement of [$^{125}$I]-iodosulpride in receptor-binding studies.

Of particular significance in accordance with the invention are compounds whose $K_i(D_2)/K_i(D_3)$ selectivity is preferably at least 10, even better at least 30 and particularly advantageously at least 50. Receptor-binding studies on $D_1$, $D_2$ and $D_4$ receptors can be carried out for example via the displacement of [$^3$H]SCH23390, [$^{125}$I]iodosulpride and [$^{125}$I]spiperone.

The compounds can, because of their binding profile, be used for the treatment of conditions which respond to dopamine $D_3$ ligands, i.e. they are effective for the treatment of those disorders or conditions where an influencing (modulation) of dopamine $D_3$ receptors leads to an improvement in the clinical condition or to cure of the disease. Examples of such conditions are disorders or conditions of the central nervous system.

Disorders or conditions of the central nervous system mean disorders affecting the spinal cord and, in particular, the brain. The term "disorder" in the inventive sense refers to abnormalities which are usually regarded as pathological states or functions and may reveal themselves in the form of particular signs, symptoms and/or dysfunctions. The inventive treatment may be directed at individual disorders, i.e. abnormalities or pathological states, but it is also possible for a plurality of abnormalities, which are causally connected together where appropriate, to be combined into patterns, i.e. syndromes, which can be treated in accordance with the invention.

The disorders which can be treated in accordance with the invention include in particular psychiatric and neurological disorders. These comprise in particular organic disorders, symptomatic disorders included, such as psychoses of the acute exogenous reaction type or associated psychoses with an organic or exogenous cause, e.g. associated with metabolic disorders, infections and endocrinopathies; endogenous psychoses such as schizophrenia and schizotypal and delusional disorders; affective disorders such as depressions, mania and manic/depressive states; and combined forms of the disorders described above; neurotic and somatoform disorders, and disorders associated with stress; dissociative disorders, e.g. deficits, clouding and splitting of consciousness and personality disorders; disorders of attention and waking/sleeping behavior, such as behavioral disorders and emotional disorders starting in childhood and adolescence, e.g. hyperactivity in children, intellectual deficits, especially attention deficit disorders, disorders of memory and cognition, e.g. learning and memory impairment (impaired cognitive function), dementia, narcolepsy and sleeping disorders, e.g. restless legs syndrome; developmental disorders; anxiety states; delirium; disorders of the sex life, e.g. male impotence; eating disorders, e.g. anorexia or bulimia; addiction; and other undefined psychiatric disorders.

The disorders which can be treated in accordance with the invention also include parkinsonism and epilepsy and, in particular, the affective disorders associated therewith. Addictive disorders include the psychological disorders and behavioral disorders caused by the abuse of psychotropic substances such as pharmaceuticals or drugs, and other addictive disorders such as, for example, compulsive gambling and impulse control disorders not elsewhere classified. Examples of addictive substances are: opioids (e.g. morphine, heroin, codeine); cocaine; nicotine; alcohol; substances which interact with the GABA chloride channel complex, sedatives, hypnotics or tranquilizers, for example benzodiazepines; LSD; cannabinoids; psychomotor stimulants such as 3,4-methylenedioxy-N-methylamphetamine (Ecstasy); amphetamine and amphetamine-like substances such as methylphenidate or other stimulants, including caffeine. Addictive substances requiring particular attention are opioids, cocaine, amphetamine or amphetamine-like substances, nicotine and alcohol.

With regard to the treatment of addictive disorders, the inventive compounds of the formula I which are particularly preferred are those which themselves have no psychotropic effect. This can also be observed in a test on rats which reduce the self-administration of psychotropic substances, for example cocaine, after administration of compounds which can be used in accordance with the invention.

According to a further aspect of the present invention, the inventive compounds are suitable for the treatment of disorders whose causes can at least in part be attributed to an abnormal activity of dopamine $D_3$ receptors.

According to another aspect of the present invention, the treatment is directed in particular at those disorders which can be influenced by a binding of, preferably exogenously added, binding partners (ligands) to dopamine $D_3$ receptors in the sense of an appropriate medical treatment.

The conditions which can be treated with the inventive compounds are frequently characterized by a progressive development, i.e. the states described above change over the course of time, the severity usually increasing and, where appropriate, states possibly interchanging or other states being added to previously existing states.

The inventive compounds can be used to treat a large number of signs, symptoms and/or dysfunctions associated with the disorders of the central nervous system and in particular the aforementioned states. These include for example a distorted relation to reality, lack of insight and the ability to comply with the usual social norms and demands of life, changes in behavior, changes in individual urges such as hunger, sleep, thirst etc. and in mood, disorders of memory and association, personality changes, especially emotional lability, hallucinations, ego disturbances, incoherence of thought, ambivalence, autism, depersonalization or hallucinations, delusional ideas, staccato speech, absence of associated movement, small-step gait, bent posture of trunk and limbs, tremor, mask-like face, monotonous speech, depression, apathy, deficient spontaneity and irresolution, reduced associationability, anxiety, nervous agitation, stammering, social phobia, panic disorders, withdrawal syndromes associated with dependence, expansive syndromes, states of agitation and confusion, dysphoria, dyskinetic syndromes and tic disorders, e.g. Huntington's chorea, Gilles de la Tourette syndrome, vertigo syndromes, e.g. peripheral postural, rotational and vestibular vertigo, melancholia, hysteria, hypochondria and the like. A treatment in the inventive sense includes not only the treatment of acute or chronic signs, symptoms and/or dysfunctions but also a preventive treatment (prophylaxis), in particular as recurrence or episode prophylaxis. The treatment may be symptomatic, for example directed at suppression of symptoms. It may take place shortterm, be directed at the medium term or may also be a longterm treatment, for example as part of maintenance therapy.

The inventive compounds are preferably suitable for the treatment of disorders of the central nervous system, especially for the treatment of affective disorders; neurotic disorders, stress disorders and somatoform disorders and psychoses and specifically for the treatment of schizophrenia and depression. Owing to their high selectivity in relation to the $D_3$ receptor, the inventive compounds I are also for the treatment of renal function disorders, especially of renal function disorders caused by diabetes mellitus (see WO 00/67847).

The inventive use of the described compounds comprises a method within the scope of the treatment. This entails the individual to be treated, preferably a mammal, in particular a human or agricultural or domestic animal, being given an effective amount of one or more compounds, usually formulated in accordance with pharmaceutical and veterinary practice. Whether such a treatment is indicated, and the form it is to take, depends on the individual case and is subject to a medical assessment (diagnosis) which takes account of the signs, symptoms and/or dysfunctions present, the risks of developing certain signs, symptoms and/or dysfunctions, and other factors.

The treatment usually takes place by administration once or more than once a day, where appropriate together or alternately with other active ingredients or active ingredient-containing products, so that an individual to be treated is given a daily dose preferably of about 0.1 to 1000 mg/kg of body weight on oral administration or of about 0.1 to 100 mg/kg of body weight on parenteral administration.

The invention also relates to the production of pharmaceutical compositions for the treatment of an individual, preferably a mammal, in particular a human or agricultural or domestic animal. Thus, the ligands are usually administered in the form of pharmaceutical compositions which comprise a pharmaceutically acceptable excipient with at least one ligand of the invention and, where appropriate, further active ingredients. These compositions can be administered for example by the oral, rectal, transdermal, subcutaneous, intravenous, intramuscular or intranasal route.

Examples of suitable pharmaceutical formulations are solid pharmaceutical forms such as oral powders, dusting powders, granules, tablets, especially film-coated tablets, pastilles, sachets, cachets, sugar-coated tablets, capsules such as hard and soft gelatin capsules, suppositories or vaginal pharmaceutical forms, semisolid pharmaceutical forms such as ointments, creams, hydrogels, pastes or patches, and liquid pharmaceutical forms such as solutions, emulsions, especially oil-in-water emulsions, suspensions, for example lotions, preparations for injection and infusion, eye drops and ear drops. Implanted delivery devices can also be used to administer inhibitors of the invention. A further possibility is also to use liposomes or microspheres.

The compositions are produced by mixing or diluting inhibitors of the invention usually with an excipient. Excipients may be solid, semisolid or liquid materials which serve as vehicle, carrier or medium for the active ingredient.

Suitable excipients are listed in the relevant pharmaceutical monographs. The formulations may additionally comprise pharmaceutically acceptable carriers or conventional excipients such as lubricants; wetting agents; emulsifying and suspending agents; preservatives; antioxidants; antiirritants; chelating agents; tablet-coating aids; emulsion stabilizers; film formers; gel formers; odor-masking agents; masking flavors; resins; hydrocolloids; solvents; solubilizers; neutralizers; permeation promoters; pigments; quaternary ammonium compounds; refatting and superfatting agents; ointment, cream or oil bases; silicone derivatives; spreading aids; stabilizers; sterilants; suppository bases; tablet excipients, such as binders, fillers, lubricants, disintegrants or coatings; propellants; desiccants; opacifiers; thickeners; waxes; plasticizers; white oils. An arrangement concerning this is based on expert knowledge as set forth for example in Fiedler, H. P., Lexikon der Hilfsstoffe für Pharmazie, Kosmetik und angrenzende Gebiete [Dictionary of Excipients for Pharmacy, Cosmetics and Associated Fields], 4th edition, Aulendorf: ECV-Editio-Cantor-Verlag, 1996.

The following examples serve to illustrate the invention without limiting it.

The nuclear magnetic resonance spectral properties (NMR) relate to chemical shifts (δ) expressed in parts per million (ppm). The relative area for the shifts in the $^1$H NMR spectrum corresponds to the number of hydrogen atoms for a particular functional type in the molecule. The nature of the shift in terms of multiplicity is indicated as singlet (s), broad singlet (s. br.), doublet (d), broad doublet (d br.), triplet (t), broad triplet (t br.), quartet (q), quintet (quint.), multiplet (m).

A) PREPARATION EXAMPLES

Example 1

2-(3-{4-[2-tert-Butyl-6-(trifluoromethyl)pyrimidin-4-yl]piperazin-1-yl}propyl)-3,4-dihydro-1H-2-benzazepine-1,5(2H)-dione 3,4-Dihydro-1H-2-benzazepine-1,5(2H)-dione (2.85 mmol, 0.50 g; prepared according to Tetrahedron Lett. 1993, 34, 5855) in dimethylformamide (5 ml) was added at 10° C. to a suspension of sodium hydride (3.40 mmol, 0.13 g, 60%, deoiled) in dimethylformamide (10 ml), and the mixture was stirred at room temperature for 1 h. Subsequently, 2-tert-butyl-4-[4-(3-chloropropyl)piperazin-1-yl]-6-(trifluoromethyl)-pyrimidine (3.00 mmol, 1.09 g; prepared according to WO 99/02503) in dimethylformamide (5 ml) was added dropwise. The reaction mixture was stirred further at room temperature for 12 h. The oil remaining after the evaporative concentration was taken up in a 1:1 mixture of ethyl acetate and water, extracted and washed with a saturated aqueous sodium chloride solution. The organic phase was dried over sodium sulfate and concentrated. The residue was purified by chromatography on silica gel (eluent: 95:5 v/v dichloromethane:methanol).

The second fraction obtained was the title compound, 2-(3-{4-[2-tert-butyl-6-(trifluoromethyl)pyrimidin-4-yl]piperazin-1-yl}propyl)-3,4-dihydro-1H-2-benzazepine-1,5(2H)-dione, in a yield of 20 mg.

ESI-MS: [M+Na$^+$]=526.2, 505.2, [M+H$^+$]=504.2, 252.6;

¹H NMR (400 MHz, CDCl₃) δ (ppm): 7.90 (1H, d), 7.68-7.54 (3H, m), 6.57 (1H, s), 3.77-3.65 (8H, m), 2.99 (2H, m sym.), 2.53 (4H, t), 2.47 (2H, t), 1.89 (2H, quint.), 1.33 (9H, s).

Example 2

1-(3-{4-[2-tert-Butyl-6-(trifluoromethyl)pyrimidin-4-yl]piperazin-1-yl}propyl)-3,4-dihydro-1H-1-benzazepine-2,5-dione Analogously to Example 1, 30.0 mg of the title compound were obtained from 3,4-dihydro-1H-1-benzazepine-2,5-dione (2.85 mmol, 0.50 g; preparation according to Arch. Pharm. 1991, 324, 579).

¹H NMR (400 MHz, CDCl₃) δ (ppm): 7.59-7.53 (2H, m), 7.33-7.24 (2H, m), 6.53 (1H, s), 3.96 (2H, s br.), 3.59 (4H, s br.), 3.02-2.92 (2H, m), 2.81 (2H, t), 2.36 (4H, t), 2.28 (2H, t), 1.73 (2H, quint.), 1.32 (9H, s).

Example 3

1-(4-{4-[2-tert-Butyl-6-(trifluoromethyl)pyrimidin-4-yl]piperazin-1-yl}butyl)-3,4-dihydro-1H-1-benzazepine-2,5-dione a) 1-(4-Chlorobutyl)-3,4-dihydro-1H-1-benzazepine-2,5-dione Analogously to the procedure described in Example 1, reaction of 3,4-dihydro-1H-1-benzazepine-2,5-dione (11.42 mmol, 2.00 g) and bromo-4-chlorobutane (13.7 mmol, 2.35 g) afforded 1.78 g of the title compound, contaminated with reactants to an extent of 30%. The mixture thus obtained was reacted without further purification.

b) 1-(4-{4-[2-tert-Butyl-6-(trifluoromethyl)pyrimidin-4-yl]piperazin-1-yl}butyl)-3,4-dihydro-1H-1-benzazepine-2,5-dione 1-(4-Chlorobutyl)-3,4-dihydro-1H-1-benzazepine-2,5-dione (3.29 mmol, 1.75 g, 70%), 2-tert-butyl-4-piperazin-1-yl-6-(trifluoromethyl)pyrimidine (3.56 mmol, 1.03 g; preparation according to WO 99/02503) and triethylamine (13.17 mmol, 1.33 g) in dimethylformamide (100 ml) were stirred at 100° C. for 12 h. Afterward, ethyl acetate was added and the mixture was washed twice with water. The combined organic phases were dried over Na₂SO₄, filtered and concentrated under reduced pressure. The oily residue was purified by chromatography on silica gel (eluent: 95:5 v/v dichloromethane:methanol); yield 0.42 g.

ESI-MS: 519.2, [M+H⁺]=518.2, 259.6;

¹H NMR (500 MHz, CDCl₃) δ (ppm): 7.57-7.52 (2H, m), 7.29 (1H, t), 7.25 (1H, d+CHCl₃), 6.57 (1H, s), 3.92 (2H, s br.), 3.63 (4H, s br.), 3.01-2.95 (2H, m), 2.80 (2H, t), 2.41 (4H, t), 2.28 (2H, t), 1.53 (2H, quint.), 1.42 (2H, quint.), 1.34 (9H, s).

Example 4

1-((2E)-4-{4-[2-tert-Butyl-6-(trifluoromethyl)pyrimidin-4-yl]piperazin-1-yl}but-2-enyl)-3,4-dihydro-1H-1-benzazepine-2,5-dione Analogously to Example 1, 0.78 g of the title compound was obtained from 3,4-dihydro-1H-1-benzazepine-2,5-dione (4.42 mmol, 0.78 g; preparation according to Arch. Pharm. 1991, 324, 579) and 2-tert-butyl-4-{4-[(2E)-4-chlorobut-2-en-1-yl]piperazin-1-yl}-6-(trifluoromethyl)pyrimidine (4.64 mmol, 1.75 g, preparation according to WO 99/02503).

ESI-MS: 517.3, [M+H⁺]=516.3, 258.6;

¹H NMR (500 MHz, CDCl₃) δ (ppm): 7.53 (1H, d), 7.48 (1H, t), 7.27-7.21 (m+CHCl₃), 6.56 (1H, s), 5.60 (2H, m sym.), 4.45 (2H, m), 3.64 (4H, s br.), 3.02-2.94 (4H, m), 2.84 (2H, t), 2.35 (4H, t), 1.35 (9H, s).

Example 5

2-(4-{4-[2-tert-Butyl-6-(trifluoromethyl)pyrimidin-4-yl]piperazin-1-yl}butyl)-3,4-dihydro-1H-2-benzazepine-1,5(2H)-dione a) 2-(4-Chlorobutyl)-3,4-dihydro-1H-2-benzazepine-1,5(2H)-dione Analogously to Example 3a, 1.04 g of the title compound contaminated with reactant to an extent of 50% were obtained from 3,4-dihydro-1H-2-benzazepine-1,5(2H)-dione and bromo-4-chlorobutane (13.7 mmol, 2.35 g). The substance was reacted without further purification.

b) 2-(4-{4-[2-tert-Butyl-6-(trifluoromethyl)pyrimidin-4-yl]piperazin-1-yl}butyl)-3,4-dihydro-1H-2-benzazepine-1,5(2H)-dione The preparation was analogous to Example 3b. 0.15 g of the title compound was obtained from 2-(4-chlorobutyl)-3,4-dihydro-1H-2-benzazepine-1,5(2H-dione (1.88 mmol, 1.00 g).

ESI-MS: [M+Na⁺]=540.3, 519.3, [M+H⁺]=518.3, 259.6.

Example 6

1-(4-{4-[2-tert-Butyl-6-(trifluoromethyl)pyrimidin-4-yl]piperazin-1-yl}butyl)-7,8-dimethoxy-3,4-dihydro-1H-1-benzazepine-2,5-dione a) 1-(4-Chlorobutyl)-7,8-dimethoxy-3,4-dihydro-1H-1-benzazepine-2,5-dione Analogously to Example 1, reaction of 7,8-dimethoxy-3,4-dihydro-1H-1-benzazepine-2,5-dione (1.70 mmol, 0.40 g, preparation according to Arch. Pharm. 1991, 324, 579) and bromo-4-chlorobutane (2.04 mmol, 0.35 g) afforded 0.20 g of the contaminated title compound. The compound is reacted further without purification.

b) 1-(4-{4-[2-tert-Butyl-6-(trifluoromethyl)pyrimidin-4-yl]piperazin-1-yl}butyl)-7,8-dimethoxy-3,4-dihydro-1H-1-benzazepine-2,5-dione Reaction of 1-(4-chlorobutyl)-7,8-dimethoxy-3,4-dihydro-1H-1-benzazepine-2,5-dione (0.49 mmol, 0.20 g) analogously to Example 3b afforded 0.12 g of the title compound.

ESI-MS: 579.2, [M+H⁺]=578.3;

¹H NMR (500 MHz, CDCl₃) δ (ppm): 7.09 (1H, s), 6.68 (1H, s), 6.56 (1H, s), 3.94 (3H, s), 3.92 (3H, s), 3.65 (4H, s br.), 2.97-2.92 (2H, m), 2.79 (2H, m br.), 2.40 (4H, t), 2.29 (2H, t), 1.49 (2H, quint.), 1.41 (2H, quint.), 1.31 (9H, s).

Example 7

1-{4-[4-(2-tert-Butyl-6-propylpyrimidin-4-yl)piperazin-1-yl]butyl}-3,4-dihydro-1H-1-benzazepine-2,5-dione hydrochloride Analogously to Example 3b, reaction of 2-tert-butyl-4-piperazin-1-yl-6-propylpyrimidine (2.68 mmol, 0.70 g) with 1-(4-chlorobutyl)-3,4-dihydro-1H-1-benzazepine-2,5-dione affords the free base of the title compounds. Subsequent reaction of the free base with HCl afforded 0.39 g of the title compound as the hydrochloride.

ESI-MS: 493.5, [M+H$^+$]=492.5, 246.7;
$^1$H NMR (400 MHz, CDCl$_3$) δ (ppm): 7.56-7.49 (3H, m), 7.31-7.18 (2H+CHCl$_3$, m), 6.10 (1H, s), 3.92 (2H, t br.), 3.58 (4H, s br.), 3.02-2.94 (2H, m), 2.81 (2H, t), 2.53 (2H, t), 2.40 (4H, s br.), 2.28 (2H, t), 1.72 (1H, q), 1.51 (2H, quint.), 1.43 (2H, quint.), 1.33 (9H, s), 0.92 (1H, t).

Example 8

1-{4-[4-(2-tert-Butyl-6-cyclobutylpyrimidin-4-yl)piperazin-1-yl]butyl}-3,4-dihydro-1H-1-benzazepine-2,5-dione hydrochloride Analogously to Example 3b, reaction of 2-tert-butyl-4-cyclobutyl-6-piperazin-1-ylpyrimidine (1.97 mmol, 0.54 g) with 1-(4-chlorobutyl)-3,4-dihydro-1H-1-benzazepine-2,5-dione afforded 0.39 g of the title compound.

ESI-MS: [M+H$^+$]=504.5, 252.9.

Example 9

1-{4-[4-(2-tert-Butyl-6-methylpyrimidin-4-yl)piperazin-1-yl]butyl}-3,4-dihydro-1H-1-benzazepine-2,5-dione hydrochloride Analogously to Example 3b, reaction of 2-tert-butyl-4-methyl-6-piperazin-1-ylpyrimidine (1.97 mmol, 0.46 g) with 1-(4-chlorobutyl)-3,4-dihydro-1H-1-benzazepine-2,5-dione afforded 0.31 g of the title compound.

ESI-MS: [M+H$^+$]=464.4, 232.6.

Example 10

1-{4-[4-(2,6-Di-tert-butylpyrimidin-4-yl)piperazin-1-yl]butyl}-3,4-dihydro-1H-1-benzazepine-2,5-dione hydrochloride Analogously to Example 3b, reaction of 2,4-di-tert-butyl-6-piperazin-1-ylpyrimidine (1.26 mmol, 0.35 g) with 1-(4-chlorobutyl)-3,4-dihydro-1H-1-benzazepine-2,5-dione afforded 0.04 g of the title compound.

ESI-MS: [M+H$^+$]=506.4, 233.8

Example 11

1-{4-[4-(2-tert-Butyl-6-isopropylpyrimidin-4-yl)piperazin-1-yl]butyl}-3,4-dihydro-1H-1-benzazepine-2,5-dione Analogously to Example 3b, reaction of 2-tert-butyl-4-isopropyl-6-piperazin-1-ylpyrimidine (0.95 mmol, 0.25 g) with 1-(4-chlorobutyl)-3,4-dihydro-1H-1-benzazepine-2,5-dione afforded 0.04 g of the title compound.

ESI-MS: [M+H$^+$]=492.5, 246.7.

Example 12

1-(5-{4-[2-tert-Butyl-6-(trifluoromethyl)pyrimidin-4-yl]piperazin-1-yl}pentanoyl)-1,2,3,4-tetrahydro-5H-1-benzazepin-5-one a) 1-(5-Chloropentanoyl)-1,2,3,4-tetrahydro-5H-1-benzazepin-5-one 5-Chlorovaleryl chloride (18.61 mmol, 2.89 g) in dimethylformamide (20 ml) was added dropwise at 10° to a suspension of 1,2,3,4-tetrahydro-5H-1-benzazepin-5-one (12.41 mmol, 2.00 g, preparation according to J. Org. Chem 1972, 37, 2849) and potassium carbonate (14.89 mmol, 2.06 g) in dimethylformamide (40 ml). The reaction mixture was stirred first at 10° C. for 1 h and then under reflux for 3 h. The precipitated salts were filtered off and the filtrate was concentrated to dryness. CH$_2$Cl$_2$ was added to the oil obtained in this way and the mixture was washed three times with 50 ml each time of a 5% aqueous sodium hydrogencarbonate solution, neutralized with 0.1N HCl (20 ml) and then washed three times with a saturated sodium chloride solution. The organic phase was dried over Na$_2$SO$_4$ and concentrated under reduced pressure; yield 3.90 g (80% pure).

ESI-MS: [M+H$^+$]=280.1;

b) 1-(5-{4-[2-tert-Butyl-6-(trifluoromethyl)pyrimidin-4-yl]piperazin-1-yl}pentanoyl)-1,2,3,4-tetrahydro-5H-1-benzazepin-5-one 1-(5-Chloropentanoyl)-1,2,3,4-tetrahydro-5H-1-benzazepin-5-one from Example 12a (1.43 mmol, 0.50 g), 2-tert-butyl-4-piperazin-1-yl-6-(trifluoromethyl)pyrimidine (1.43 mmol, 0.41 g, preparation according to DE 19735410), NaBr (7.14 mmol, 0.74 g), DIPEA (diisopropylethylamine) (14.01 mmol, 1.81 g) and N-methylpyrrolidinone (0.6 ml) were heated to 120° C. for 5 h. Subsequently, the reaction mixture was filtered and the resulting filtrate was concentrated to dryness. Afterward, ethyl acetate was added to the resulting residue and it was washed with saturated, aqueous sodium chloride solution. The organic phase was dried and then concentrated to dryness. The residue was purified by chromatography on silica gel, eluent: methyl tert-butyl ether/methanol (0-100%); to obtain 0.31 g of the title compound.

ESI-MS: [M+H$^+$]=532.7, 267.0.

Example 13

1-{5-[4-(2-tert-Butyl-6-propylpyrimidin-4-yl)piperazin-1-yl]pentanoyl}-1,2,3,4-tetrahydro-5H-1-benzazepin-5-one hydrochloride Analogously to the method for Example 12b, 0.40 g of the title compound was obtained from 1-(5-chloropentanoyl)-1,2,3,4-tetrahydro-5H-1-benzazepin-5-one (1.61 mmol, 0.50 g) and 2-tert-butyl-4-piperazin-1-yl-6-propylpyrimidine (1.61 mmol, 0.42 g, preparation according to DE 19735410).

ESI-MS: [M+H$^+$]=506.4, 253.6.

Example 14

1-(4-{4-[2-tert-Butyl-6-(trifluoromethyl)pyrimidin-4-yl]piperazin-1-yl}butanoyl)-1,2,3,4-tetrahydro-5H-1-benzazepin-5-one a) 1-(4-Chlorobutyryl)-1,2,3,4-tetrahydrobenzo[b]azepin-5-one Analogously to the method for Example 12a, 0.24 g of 1-(4-chlorobutyryl)-1,2,3,4-tetra-hydrobenzo[b]azepin-5- one was obtained from 1,2,3,4-tetrahydro-5H-1-benzazepin-5-one (1.24 mmol, 0.20 g, preparation according to J. Org. Chem 1972, 37, 2849) and 4-chlorobutyryl chloride (1.86 mmol, 0.27 g) in dioxane (10 ml).

b) 1-(4-{4-[2-tert-Butyl-6-(trifluoromethyl)pyrimidin-4-yl]piperazin-1-yl}butanoyl)-1,2,3,4-tetrahydro-5H-1-benzazepin-5-one Analogously to the method for Example 12b, 0.40 g of the title compound was obtained from 1-(4-chlorobutyryl)-1,2,3,4-tetrahydrobenzo[b]azepin-5-one (0.45 mmol, 0.12 g) from Example 14a and 2-tert-butyl-4-piperazin-1-yl-6-(trifluoromethyl)pyrimidine (0.45 mmol, 0.12, prepared according to DE 19735410).
ESI-MS: [M+H$^+$]=518.3, 259.6.

Example 15

1-{4-[4-(2-tert-Butyl-6-propylpyrimidin-4-yl)piperazin-1-yl]butyryl}-1,2,3,4-tetrahydrobenzo[b]azepin-5-one Analogously to the method for Example 12b, 85.0 mg of the title compound are obtained from 1-(4-chlorobutyryl)-1,2,3,4-tetrahydrobenzo[b]azepin-5-one from Example 14a (0.45 mmol, 0.12 g) and 2-tert-butyl-4-piperazin-1-yl-6-propylpyrimidine (0.45 mmol, 0.12 g, prepared according to DE 19735410).
ESI-MS: [M+H$^+$]=492.4, 246.7.

Example 16

1-{4-[4-(2-tert-Butyl-6-cyclopropylpyrimidin-4-yl)piperazin-1-yl]butyl}-3,4-dihydro-1H-benzo[b]azepine-2,5-dione Analogously to the method for Example 12b, 45.0 mg of the title compound are obtained from 1-(4-chlorobutyl)-3,4-dihydro-1H-1-benzazepine-2,5-dione from Example 3a (0.38 mmol, 0.10 g) and 2-tert-butyl-4-cyclopropyl-6-piperazin-1-ylpyrimidine (0.40 mmol, 0.05 g; prepared according to DE 19728996).
ESI-MS: [M+H$^+$]=490.4, 245.7.

Example 17

1-{4-[4-(2-tert-Butyl-6-trifluoromethylpyrimidin-4-yl)piperazin-1-yl]butyl}-1H-quinoline-2,4-dione trifluoracetate a) 1-(4-Chlorobutyl)-4-hydroxy-1H-quinolin-2-one Analogously to the procedure described in Example I, reaction of 4-hydroxy-1H-quinolin-2-one (24.82 mmol, 4.00 g, prepared according to Monatsh. Chem. 1965, 96, 418) and bromo-4-chlorobutane (29.78 mmol, 5.11 g) afforded 6.70 g of the title compound which is contaminated with reactant. The mixture thus obtained was used in the next step without further purification.

b) 1-{4-[4-(2-tert-Butyl-6-trifluoromethylpyrimidin-4-yl)piperazin-1-yl]butyl}-1H-quinoline-2,4-dione Analogously to the method from Example 3b, 3.20 g of the title compound were obtained from 1-(4-chlorobutyl)-4-hydroxy-1H-quinolin-2-one from Example 17a (4.00 g).

ESI-MS: [M+Na+]=526.5, 505.5, [M+H+]=504.5, 454.5, 252.7;
1H NMR (500 MHz, CDCl3) δ (ppm): 11.75 (1H, s br.), 7.85 (1H, d), 7.42 (t, 1H), 7.26-7.20 (2H+CHCl3, m), 6.66 (1H, s.), 5.98 (1H, s), 4.18 (2H, m sym.), 3.29 (2H, m sym.), 2.21 (2H, quint.), 2.04 (2H, quint.), 1.33 (9H, s).

Example 18

1-[4-(7-Propionyl-3,4-dihydroisoquinolin-2(1H)-yl)butyl]-3,4-dihydro-1H-1-benzazepine-2,5-dione a) 2-(Trifluoroacetyl)-1,2,3,4-tetrahydroisoquinoline Trifluoroacetic anhydride (2.13 mol, 452.0 g) was initially charged in dichloromethane (452 ml) at 10-15° C. A solution of tetrahydroisoquinoline (1.94 mol, 268.3 g) in dichloromethane (90 ml) was added thereto at this temperature. The reaction mixture was stirred further at room temperature overnight and then hydrolyzed with ice-water (813 g). After stirring for 1 h, the phases were separated. The organic phase was washed successively with water (813 ml), with semiconcentrated NaHCO$_3$ solution (550 ml) and again with water (500 ml). Subsequently, the mixture was concentrated under reduced pressure to obtain 446 g of crude product which was used in the subsequent reaction.

b) 1-[2-(Trifluoroacetyl)-1,2,3,4-tetrahydroisoquinolin-7-yl]propan-1-one

Aluminum trichloride (0.78 mol, 103.7 g) was suspended in dichloromethane (93 ml) at 10-15° C. Subsequently, the trifluoroacetyltetrahydroisoquinoline from step a) (2.13 mol, 452.0 g) and propionyl chloride (0.47 mol, 43.2 g) were added successively with cooling at this temperature. Subsequently, the mixture was heated to reflux (heating bath temperature 60° C.; reflux about 43° C.) and the heating bath temperature was retained for 5 h. In the course of this, the internal temperature rose slowly from 43° C. to 51° C. The mixture was then cooled to 5-10° C. and then diluted with 70 ml of dichloromethane. The reaction solution was subsequently introduced rapidly with ice bath cooling into a mixture of 1000 g of ice and 500 ml of methyl tert-butyl ether. After 30 min, the phases were separated and the organic phase was washed successively with 500 ml of water, with 500 ml of semiconcentrated NaHCO$_3$ solution and again with 300 ml of water. The organic phase was subsequently concentrated under reduced pressure to obtain 89.9 g of a mixture of the title compound with its 6-isomer (7-isomer:6-isomer isomeric ratio: about 75:25 (by means of $^{13}$C NMR)) which was used in the next stage.

c) 7-Propionyl-1,2,3,4-tetrahydroisoquinoline(hydrochloride)

The product from step b) (0.39 mol, 111.0 g) was dissolved in n-propanol (744 ml) and hydrochloric acid (32%, 3.5 mol, 400 g) was added thereto. Subsequently, the mixture was heated to reflux for 5 h. Afterward, a further 300 ml of n-propanol were added and water was distilled off in an azeotrope with n-propanol. A total of 890 ml of distillate were distilled off. In the course of this, the hydrochloride of the propionylisoquinoline precipitated out; another 1500 ml of n-propanol were added and distilled off again. Subsequently, 1200 ml of methyl tert-butyl ether were added, and the mixture was cooled to 5° C. and stirred for 30 min. The resulting solid was filtered off and dried at 40-50° C. under reduced pressure. In this way, 82.9 g of a mixture of 6- and 7-propionyl-1,2,3,4-tetrahydroisoquinoline were obtained as the hydrochloride with an isomer ratio of 7-isomer:6-isomer of about 80:20 (determined by means of $^{13}$C NMR).

d) 1-[4-(7-Propionyl-3,4-dihydroisoquinolin-2(1H)-yl)butyl]-3,4-dihydro-1H-1-benzazepine-2,5-dione Analogously to the method for Example 3b, 0.37 g of the title compound was obtained from 7-propionyl-1,2,3,4-tetrahydroisoquinolinium hydrochloride (3.00 mmol, 0.68 g).
ESI-MS: [M+Na$^+$]=441.4, 420.4, [M+H$^+$]=419.4.

Example 19

1-[4-(6-Chloro-1,2,4,5-tetrahydro-3H-3-benzazepin-3-yl)butyl]-3,4-dihydro-1H-1-benzazepine-2,5-dione Analogously to Example 3b, reaction of 6-chloro-2,3,4,5-tetrahydro-1H-3-benzazepinium-(2E)-3-carboxyacrylate (0.95 mmol, 0.28 g, preparation according to J. Med. Chem. 1990, 33, 633) with 1-(4-chlorobutyl)-3,4-dihydro-1H-1-benzazepine-2,5-dione afforded 13.0 mg of the title compound.
ESI-MS: 414.2, 413.1, [M+H$^+$]=411.2.

Example 20

2-[4-(2,5-Dioxo-2,3,4,5-tetrahydro-1H-1-benzazepin-1-yl)butyl]-1,2,3,4-tetrahydroisoquinoline-6-carbonitrile trifluoroacetate Analogously to the method for Example 3b, reaction of 1,2,3,4-tetrahydroisoquinoline-6-carbonitrile (0.94 mmol, 0.15 g, preparation according to J. Med. Chem. 2000, 43, 1878) with 1-(4-chlorobutyl)-3,4-dihydro-1H-1-benzazepine-2,5-dione afforded 26.5 mg of the title compound.
ESI-MS: 389.2, [M+H$^+$]=388.1.

Example 21

1-[4-(4-Methylpiperazin-1-yl)butyl]-3,4-dihydro-1H-1-benzazepine-2,5-dione hydrochloride Analogously to the method for Example 3b, 0.02 g of the title compound was obtained from 1-methylpiperazine (1.23 mmol, 0.12 g).
ESI-MS: [M+H$^+$]=330.2.

Example 22

1-[4-(4-Ethylpiperazin-1-yl)butyl]-3,4-dihydro-1H-1-benzazepine-2,5-dione

Analogously to the method for Example 3b, 0.01 g of the title compound was obtained from 1-ethylpiperazine (1.26 mmol, 0.14 g).
ESI-MS: [M+H$^+$]=344.3.

Example 23

1-[4-(4-Isobutylpiperazin-1-yl)butyl]-3,4-dihydro-1H-1-benzazepine-2,5-dione hydrochloride Analogously to the method for Example 3b, 0.13 g of the title compound was obtained from 1-isobutylpiperazine (0.97 mmol, 0.14 g).

ESI-MS: [M+H$^+$]=372.4, 186.8;
$^1$H NMR (400 MHz, CDCl$_3$) δ (ppm): 7.58-7.51 (2H, m), 7.32-7.23 (m, 2H+CHCl$_3$), 3.87 (2H, t), 2.97 (2H, m), 2.78 (2H, t), 2.40 (s br.), 2.25 (2H, t), 2.06 (2H, d), 1.75 (1H, sept.), 1.50 (2H, quint.).

Example 24

1-[4-(2,4,6-Trimethylpiperazin-1-yl)butyl]-3,4-dihydro-1H-1-benzazepine-2,5-dione Analogously to the method for Example 3b, 0.08 g of the title compound was obtained from 1,3,5-trimethylpiperazine (0.97 mmol, 0.12 g).
ESI-MS: [M+H$^+$]=358.3, 179.1, 157.1, 129.1.

Example 25

1-[4-(4-Propylpiperazin-1-yl)butyl]-3,4-dihydro-1H-benzo[b]azepine-2,5-dione

Analogously to the method for Example 12b, 0.10 g of the title compound was obtained from 1-(4-chlorobutyl)-3,4-dihydro-1H-1-benzazepine-2,5-dione (0.50 mmol, 0.13 g) and 1-propylpiperazine dihydrobromide (0.47 mmol, 0.14 g).
ESI-MS: [M+H$^+$]=358.3;
$^1$H NMR (400 MHz, CDCl$_3$) δ (ppm): 7.58-7.50 (2H, m), 7.33-7.21 (2H+CHCl$_3$, m), 3.87 (t, 2H), 2.95 (2H, t), 2.79 (2H, t), 2.41 (8H, s br.), 2.27 (2H, quart.), 1.49 (2H, quint.), 1.39 (2H, quint.), 0.89 (3H, t).

Example 26

1-[4-((R)-3-Methylpiperazin-1-yl)butyl]-3,4-dihydro-1H-benzo[b]azepine-2,5-dione Analogously to the method for Example 12b, 0.07 g of the title compound was obtained from 1-(4-chlorobutyl)-3,4-dihydro-1H-1-benzazepine-2,5-dione (0.56 mmol, 0.15 g) and (R)-(−)-2-methylpiperazine (0.54 mmol, 0.05 g).
ESI-MS: [M+H$^+$]=330.1.

Example 27

1-[4-(4-Ethyl-(R)-3-methylpiperazin-1-yl)butyl]-3,4-dihydro-1H-benzo[b]azepine-2,5-dione 30.0 mg of the title compound were obtained by reductive amination by the method specified by A. Magid et al. in Tetrahedron Lett. 31 (1990), p. 5595 from 1-[4-((R)-3-methylpiperazin-1-yl)butyl]-3,4-dihydro-1H-benzo[b]azepine-2,5-dione from Example 26 (0.18 mmol, 60.0 mg) and acetaldehyde (0.18 mmol, 8.0 mg).
ESI-MS: [M+H$^+$]=358.3;
$^1$H NMR (400 MHz, CDCl$_3$) δ (ppm): 7.60-7.46 (2H, m), 7.35-7.14 (2H+CHCl3, m), 3.87 (t, 2H), 2.97 (2H, t), 2.92-2.74 (4H, m), 2.71 (1H, d), 2.61 (1H, d), 2.50-2.03 (6H, m incl. 2.22 (2H, t)), 1.84 (1H, s br.), 1.50 (2H, quint.), 1.38 (2H, quint.), 1.14-0.91 (6H, m).

Example 28

1-[4-((S)-3-Methylpiperazin-1-yl)butyl]-3,4-dihydro-1H-benzo[b]azepine-2,5-dione Analogously to the method for Example 12b, reaction of 1-(4-chlorobutyl)-3,4-dihydro-1H-1-benzazepine-2,5-dione (0.56 mmol, 0.15 g) with (S)-(+)-2-methylpiperazine (0.54 mmol, 0.05 g) afforded 40.0 mg of the title compound.
ESI-MS: [M+H$^+$]=330.2.

Example 29

1-[4-(4-Ethyl-(S)-3-methylpiperazin-1-yl)butyl]-3,4-dihydro-1H-benzo[b]azepine-2,5-dione Analogously to the method from Example 27, reductive amination afforded 10.0 mg of the title compound from 1-[4-((S)-3-methylpiperazin-1-yl)butyl]-3,4-dihydro-1H-benzo[b]azepine-2,5-dione from Example 28 (0.12 mmol, 40.0 mg) and acetaldehyde (0.12 mmol, 5.0 mg).
ESI-MS: [M+H$^+$]=358.3.

Example 30

1-[4-(4-Ethylpiperazin-1-yl)-4-oxobutyl]-3,4-dihydro-1H-benzo[b]azepine-2,5-dione a) Methyl 4-(2,5-dioxo-2,3,4,5-tetrahydrobenzo[b]azepin-1-yl)butanoate Analogously to the method for Example 1, 100 mg of the title compound were obtained from 3,4-dihydro-1H-benzo[b]azepine-2,5-dione (5.71, 1.00 g, prepared according to Tetrahedron Lett. 1993, 34, 5855) and methyl 4-iodobutanoate (5.71 mmol, 1.37 g).
ESI-MS: [M+H$^+$]=276.15;

b) 4-(2,5-Dioxo-2,3,4,5-tetrahydrobenzo[b]azepin-1-yl)butanoic acid

Methyl 4-(2,5-dioxo-2,3,4,5-tetrahydrobenzo[b]azepin-1-yl)butanoate from step a (100 mg, 0.36 mmol) in water/methanol (0.7:2.0 ml) was treated with NaOH (1N, 0.80 ml) to obtain 63.0 mg of 4-(2,5-dioxo-2,3,4,5-tetrahydrobenzo[b]azepin-1-yl)butanoic acid.
ESI-MS: [M+H$^+$]=262.0;

c) 1-[4-(4-ethylpiperazin-1-yl)-4-oxobutyl]-3,4-dihydro-1H-benzo[b]azepine-2,5-dione On the basis of the method described by M. K. Dhaon et al. in J. Org. Chem. 47 (1982) p. 1962, reaction of 4-(2,5-dioxo-2,3,4,5-tetrahydrobenzo[b]azepin-1-yl)butanoic acid (0.06 g) from step b and 1-ethylpiperazine (0.25 mmol, 0.03 g) in the presence of EDC.HCl (N'-(3-dimethylaminopropyl)-N-ethylcarbodiimide hydrochloride) (0.36 mmol, 0.07 g), Et$_3$N (0.48 mmol, 0.05 g) in tetrahydrofuran (5 ml) afforded 10.0 mg of the title compound.
ESI-MS: [M+H$^+$]=358.3.
The preparation of the compounds of Examples 31-60 was based on the above-described methods.

Example 31

1-[4-(2,5-Dioxo-2,3,4,5-tetrahydrobenzo[b]azepin-1-yl)butyl]-4-isopropylpiperazin-1-ium trifluoroacetate

ESI-MS: [M+H$^+$]=358.2.

Example 32

4-sec-Butyl-1-[4-(2,5-dioxo-2,3,4,5-tetrahydrobenzo[b]azepin-1-yl)butyl]piperazin-1-ium trifluoroacetate

ESI-MS: [M+H$^+$]=372.3.

Example 33

1-[4-(2,5-Dioxo-2,3,4,5-tetrahydrobenzo[b]azepin-1-yl)butyl]-4-(1-methylbutyl)piperazin-1-ium trifluoroacetate

ESI-MS: [M+H$^+$]=386.1.

Example 34

4-Butyl-1-[4-(2,5-dioxo-2,3,4,5-tetrahydrobenzo[b]azepin-1-yl)butyl]piperazin-1-ium trifluoroacetate

ESI-MS: [M+H$^+$]=372.1.

Example 35

1-[4-(2,5-Dioxo-2,3,4,5-tetrahydrobenzo[b]azepin-1-yl)butyl]-4-(1-ethylpropyl)piperazin-1-ium trifluoroacetate

ESI-MS: [M+H$^+$]=386.1.

Example 36

4-Cyclopentyl-1-[4-(2,5-dioxo-2,3,4,5-tetrahydrobenzo[b]azepin-1-yl)butyl]piperazin-1-ium trifluoroacetate

ESI-MS: [M+H$^+$]=384.4.

Example 37

4-Cyclohexyl-1-[4-(2,5-dioxo-2,3,4,5-tetrahydrobenzo[b]azepin-1-yl)butyl]piperazin-1-ium trifluoroacetate

ESI-MS: [M+H$^+$]=398.5.

Example 38

4-(3-Cyclohexylpropyl)-1-[4-(2,5-dioxo-2,3,4,5-tetrahydrobenzo[b]azepin-1-yl)butyl]piperazin-1-ium trifluoroacetate

ESI-MS: [M+H$^+$]=440.4, 238.9, 211.0.

Example 39

4-Cyclohexylmethyl-1-[4-(2,5-dioxo-2,3,4,5-tetrahydrobenzo[b]azepin-1-yl)butyl]piperazin-1-ium trifluoroacetate

ESI-MS: [M+H$^+$]=412.4, 279.0, 183.0.

Example 40

4-(2-Cyclohexylethyl)-1-[4-(2,5-dioxo-2,3,4,5-tetrahydrobenzo[b]azepin-1-yl)butyl]piperazin-1-ium trifluoroacetate

ESI-MS: [M+H$^+$]=426.4, 307.1, 197.0.

Example 41

1-[4-(2,5-Dioxo-2,3,4,5-tetrahydrobenzo[b]azepin-1-yl)butyl]-4-(tetrahydrofuran-2-ylmethyl)piperazin-1-ium trifluoroacetate ESI-MS: [M+Na$^+$]=422.4, [M+H$^+$]=400.4, 170.9.

Example 42

4-Benzyl-1-[4-(2,5-dioxo-2,3,4,5-tetrahydrobenzo[b]azepin-1-yl)butyl]piperazin-1-ium trifluoroacetate

ESI-MS: [M+H$^+$]=406.3.

Example 43

1-[4-(2,5-Dioxo-2,3,4,5-tetrahydrobenzo[b]azepin-1-yl)butyl]-4-(2-pyrrol-1-yl-ethyl)piperazin-1-ium trifluoroacetate

ESI-MS: [M+H$^+$]=409.2.

Example 44

1-[4-(2,5-Dioxo-2,3,4,5-tetrahydrobenzo[b]azepin-1-yl)butyl]-4-(2-imidazol-1-ylethyl)piperazin-1-ium trifluoroacetate ESI-MS: [M+Na$^+$]=432.0, [M+H$^+$]=410.0, 342.0, 113.0.

Example 45

1-[4-(2,5-Dioxo-2,3,4,5-tetrahydrobenzo[b]azepin-1-yl)butyl]-4-(2-thiophen-2-yl-ethyl)piperazin-1-ium trifluoroacetate

ESI-MS: [M+H$^+$]=426.4.

Example 46

1-[4-(2,5-Dioxo-2,3,4,5-tetrahydrobenzo[b]azepin-1-yl)butyl]-4-(2-methoxyethyl)-piperazin-1-ium trifluoroacetate

ESI-MS: [M+H$^+$]=374.2.

Example 47

1-[4-(2,5-Dioxo-2,3,4,5-tetrahydrobenzo[b]azepin-1-yl)butyl]-4-(3-methoxypropyl)-piperazin-1-ium trifluoroacetate

ESI-MS: [M+H$^+$]=388.1.

Example 48

1-[4-(2,5-Dioxo-2,3,4,5-tetrahydrobenzo[b]azepin-1-yl)butyl]-4-(2-ethoxyethyl)piperazin-1-ium trifluoroacetate ESI-MS: [M+Na$^+$]=410.0, [M+H$^+$]=388.2.

Example 49

4-(2-Dimethylaminoethyl)-1-[4-(2,5-dioxo-2,3,4,5-tetrahydrobenzo[b]azepin-1-yl)-butyl]piperazin-1-ium trifluoroacetate

ESI-MS: [M+H$^+$]=387.1, 341.9.

Example 50

4-(3-Cyanopropyl)-1-[4-(2,5-dioxo-2,3,4,5-tetrahydrobenzo[b]azepin-1-yl)butyl]-piperazin-1-ium trifluoroacetate ESI-MS: [M+Na$^+$]=405.0, [M+H$^+$]=383.1, 153.9.

Example 51

1-[4-(2,5-Dioxo-2,3,4,5-tetrahydrobenzo[b]azepin-1-yl)butyl]-4-(2-oxo-2-pyrrolidin-1-ylethyl)piperazin-1-ium trifluoroacetate ESI-MS: [M+Na$^+$]=449.0, [M+H$^+$]=427.1, 197.9.

Example 52

1-[4-(2,5-Dioxo-2,3,4,5-tetrahydrobenzo[b]azepin-1-yl)butyl]-4-(2-morpholin-4-yl-2-oxoethyl)piperazin-1-ium trifluoroacetate ESI-MS: [M+Na$^+$]=465.0, [M+H$^+$]=443.2.

Example 53

1-[4-(2,5-Dioxo-2,3,4,5-tetrahydrobenzo[b]azepin-1-yl)butyl]-4-(2-oxo-2-piperidin-1-ylethyl)piperazin-1-ium trifluoroacetate ESI-MS: [M+Na$^+$]=463.1, [M+H$^+$]=441.3.

Example 54

4-Cyclopropanecarbonyl-1-[4-(2,5-dioxo-2,3,4,5-tetrahydrobenzo[b]azepin-1-yl)-butyl]piperazin-1-ium trifluoroacetate ESI-MS: [M+Na$^+$]=405.9, [M+H$^+$]=384.2, 127.9.

Example 55

4-Acetyl-1-[4-(2,5-dioxo-2,3,4,5-tetrahydrobenzo[b]azepin-1-yl)butyl]piperazin-1-ium trifluoroacetate

ESI-MS: [M+H$^+$]=358.0.

Example 56

1-[4-(2,5-Dioxo-2,3,4,5-tetrahydrobenzo[b]azepin-1-yl)butyl]-4-(tetrahydrofuran-2-carbonyl)piperazin-1-ium trifluoroacetate ESI-MS: [M+Na$^+$]=436.1, [M+H$^+$]=414.2, 315.9.

Example 57

1-[4-(2,5-Dioxo-2,3,4,5-tetrahydrobenzo[b]azepin-1-yl)butyl]-4-(furan-2-carbonyl)-piperazin-1-ium trifluoroacetate

ESI-MS: [M+H$^+$]=410.2.

Example 58

1-[4-(2,5-Dioxo-2,3,4,5-tetrahydrobenzo[b]azepin-1-yl)butyl]-4-ethanesulfonylpiperazin-1-ium trifluoroacetate ESI-MS: [M+Na$^+$]=430.0, [M+H$^+$]=408.0.

Example 59

1-[4-(2,5-Dioxo-2,3,4,5-tetrahydrobenzo[b]azepin-1-yl)butyl]-4-methyl[1,4]diazepan-1-ium trifluoroacetate

ESI-MS: [M+H$^+$]=344.0.

Example 60

1-[4-(4-Allylpiperazin-1-yl)butyl]-3,4-dihydro-1H-1-benzazepine-2,5-dione

Analogously to the method for Example 3b, 0.08 g of the title compound was obtained from 1-allylpiperazinediium dichloride (0.97 mmol, 0.19 g).
ESI-MS: [M+H$^+$]=356.3, 178.6;
$^1$H NMR (400 MHz, CDCl$_3$) δ (ppm): 7.53 (2H, t), 7.39-7.18 (m, 2H+CHCl$_3$), 5.85 (1H, sext.), 5.15 (2H, t), 3.87 (2H, t), 2.98 (4H, m), 2.79 (2H, t), 2.42 (6H, s br.), 2.27 (2H, t), 1.50 (2H, quint.), 1.39 (2H, quint.).

Example 61 tert-Butyl 4-[4-(2,5-dioxo-2,3,4,5-tetrahydro-1H-1-benzazepin-1-yl)butyl]piperazine-1-carboxylate Analogously to the method for Example 3b, 3.44 g of the title compound were obtained from tert-butyl piperazine-N-carboxylate (10.01 mmol, 1.86 g)
ESI-MS: [M+H$^+$]=416.2;
$^1$H NMR (400 MHz, CDCl$_3$) δ (ppm): 7.53 (2H, t), 7.37-7.20 (m, 2H+CHCl$_3$), 3.88 (2H, t), 3.37 (4H, t), 2.96 (2H, t), 2.80 (2H, t), 2.36-2.16 (6H, m), 1.57-1.32 (13H, m incl. 1.47, s, 9H).

Example 62

1-(4-Piperazin-1-ylbutyl)-3,4-dihydro-1H-1-benzazepine-2,5-dione tert-Butyl 4-[4-(2,5-dioxo-2,3,4,5-tetrahydro-1H-1-benzazepin-1-yl)butyl]piperazine-1-carboxylate from Example 61 (8.28 mmol, 3.44 g) in diethyl ether (40 ml) was admixed with saturated ethereal HCl (30 ml) and the mixture was stirred at room temperature for 12 h. The reaction mixture was then filtered and the resulting residue was washed with diethyl ether to obtain 0.93 g of the title compound.
ESI-MS: [M+H$^+$]=316.1, 158.6;
$^1$H NMR (400 MHz, CDCl$_3$) δ (ppm): 7.52 (2H, t), 7.29-7.18 (m, 2H+CHCl$_3$), 3.91 (2H, t), 2.91 (2H, m), 2.78 (4H, t), 2.73 (2H, t), 2.26 (4H, s br.), 2.17 (2H, t), 1.73 (1H, s br.), 1.46 (2H, quint.), 1.35 (2H, quint.).

Example 63

1-{4-[(1S,4S)-5-Methyl-2,5-diazabicyclo[2.2.1]hept-2-yl]butyl}-3,4-dihydro-1H-1-benzazepine-2,5-dione Analogously to the method for Example 3b, 0.01 g of the title compound was obtained from (1S,4S)-5-methyl-5-aza-2-azoniabicyclo[2.2.1]heptane trifluoroacetate (0.56 mmol, 0.21 g).
ESI-MS: 343.2, [M+H$^+$]=342.2, 171.6.

Example 64

1-[4-(Hexahydropyrrolo[1,2-a]pyrazin-2(1H)-yl)butyl]-3,4-dihydro-1H-1-benzazepine-2,5-dione Analogously to the method for Example 12b, reaction of 1-(4-chlorobutyl)-3,4-dihydro-1H-1-benzazepine-2,5-dione (0.40 mmol, 0.11 g) and octahydropyrrolo[1,2-a]pyrazine (0.40 mmol, 0.05 g) afforded 0.05 g of the title compound.
ESI-MS: 357.2, [M+H$^+$]=356.3, 178.6.

Example 65

Benzyl (1R,5R)-6-[4-(2,5-dioxo-2,3,4,5-tetrahydro-1H-1-benzazepin-1-yl)butyl]-3,6-diazabicyclo[3.2.0]heptane-3-carboxylate Analogously to the method for Example 12b, 0.22 g of the title compound were obtained from benzyl (1R,5R)-3,6-diazabicyclo[3.2.0]heptane-3-carboxylate (1.43 mmol, 0.33 g, prepared according to WO 01/81347).
ESI-MS: [M+H$^+$]=462.3.

Example 66

1-{4-[(1R,5R)-3,6-Diazabicyclo[3.2.0]hept-6-yl]butyl}-3,4-dihydro-1H-1-benzazepine-2,5-dione In the presence of Pd/C (0.01 g, 10%), benzyl (1R,5R)-6-[4-(2,5-dioxo-2,3,4,5-tetrahydro-1H-1-benzazepin-1-yl)butyl]-3,6-diazabicyclo[3.2.0]heptane-3-carboxylate from Example 65 (0.45 mmol, 0.21 g) in methanol (7 ml) was reacted with hydrogen to obtain 0.10 g of the title compound.

Example 67

Benzyl (1S,5S)-6-[4-(2,5-dioxo-2,3,4,5-tetrahydro-1H-1-benzazepin-1-yl)butyl]-3,6-diazabicyclo[3.2.0]heptane-3-carboxylate Analogously to Example 3b, 0.21 g of the title compound was obtained from benzyl (1S,5S)-3,6-diazabicyclo[3.2.0]heptane-3-carboxylate (1.42 mmol, 0.33 g, prepared according to WO 0/181347).
ESI-MS: [M+H$^+$]=462.3.

Example 68

1-{4-[(1S,5S)-3,6-Diazabicyclo[3.2.0]hept-6-yl]butyl}-3,4-dihydro-1H-1-benzazepine-2,5-dione On the basis of the method for Example 66, hydrogenation of benzyl (1S,5S)-6-[4-(2,5-dioxo-2,3,4,5-tetrahydro-1H-1-benzazepin-1-yl)butyl]-3,6-diazabicyclo[3.2.0]heptane-3-carboxylate from Example 67 (0.46 mmol, 0.21 g) afforded 0.12 g of the title compound.

Example 69

1-{4-[(1S,5S)-3-Ethyl-3,6-diazabicyclo[3.2.0]hept-6-yl]butyl}-3,4-dihydro-1H-1-benzazepine-2,5-dione Analogously to the method in Example 27, reductive amination of 1-{4-[(1S,5S)-3,6-diazabicyclo[3.2.0]hept-6-yl]butyl}-3,4-dihydro-1H-1-benzazepine-2,5-dione from Example 68 (0.21 mmol, 0.07 g) and acetaldehyde (0.21 mmol, 9 mg) afforded 0.01 g of the title compound.
ESI-MS: [M+H$^+$]=356.3.

Example 70

1-{4-[(1R,5R)-3-Methyl-3,6-diazabicyclo[3.2.0]hept-6-yl]butyl}-3,4-dihydro-1H-benzo[b]azepine-2,5-dione Analogously to the method from Example 27, reductive amination of 1-{4-[(1R,5R)-(3,6-diazabicyclo[3.2.0]hept-6-yl)butyl]-3,4-dihydro-1H-benzo[b]azepine-2,5-dione from Example 66 (0.27 mmol, 0.09 g) and formaldehyde (0.30 mmol, 25.0 mg, 37% solution) afforded 0.02 g of the title compound.
ESI-MS: [M+K$^+$]=380.1, [M+H$^+$]=342.3.

Example 71 tert-Butyl 5-[4-(2,5-dioxo-2,3,4,5-tetrahydrobenzo [b]azepin-1-yl)butyl]-(3S, 6S)-hexahydropyrrolo[3,4-c]pyrrole-2-carboxylate Analogously to the method from Example 12b, reaction of 1-(4-chlorobutyl)-3,4-dihydro-1H-1-benzazepine-2,5-dione (1.14 mmol, 0.30 g) and tert-butyl (3S,6S)-hexahydropyrrolo[3,4-c]pyrrole-2-carboxylate (1.08 mmol, 0.23 g; prepared according to WO 01/81347) afforded 0.25 g of the title compound.
ESI-MS: [M+H$^+$]=442.4;
$^1$H NMR (400 MHz, CDCl$_3$) δ (ppm): 7.63-7.50 (2H, m), 7.36-7.17 (2H+CHCl$_3$, m), 3.89 (t, 2H), 3.50 (2H, s br.), 3.15 (2H, s br.), 2.95 (2H, m sym.), 2.87-2.69 (4H, m), 2.60 (2H, s br.), 2.41-2.19 (4H, m), 1.77-1.22 (13H, m incl. 1.45 (9H, s)).

Example 72

1-[4-((3S,6S)-Hexahydropyrrolo[3,4-c]pyrrol-2-yl) butyl]-3,4-dihydro-1H-benzo[b]azepine-2,5-dione The reaction of tert-butyl 5-[4-(2,5-dioxo-2,3,4,5-tetrahydrobenzo[b]azepin-1-yl)butyl]-(3S,6S)-hexahydropyrrolo [3,4-c]pyrrole-2-carboxylate from Example 71 (0.54 mmol, 02.4 g) with trifluoroacetic acid (2.69 ml) gave 0.17 g of the title compound.

Example 73

1-[4-((3S,6S)-5-Methylhexahydropyrrolo[3,4-c]pyrrol-2-yl)butyl]-3,4-dihydro-1H-benzo[b]azepine-2,5-dione Analogously to the method in Example 27, reductive amination of 1-[4-((3S,6S)-hexahydropyrrolo[3,4-c]pyrrol-2-yl) butyl]-3,4-dihydro-1H-benzo[b]azepine-2,5-dione from Example 72 (0.24 mmol, 82.0 mg) and formaldehyde (0.26 mmol, 21.4 mg, 37% solution) afforded 10.0 mg of the title compound.
$^1$H NMR (400 MHz, CDCl$_3$) δ (ppm): 7.61-7.47 (2H, m), 7.39-7.17 (2H+CHCl$_3$, m), 3.88 (t, 2H), 2.96 (2H, t), 2.80 (4H, t), 2.47-2.17 (7H, m), 1.91-1.14 (10H, m).

Example 74

1-[4-(Octahydropyrido[1,2-a][1,4]diazepin-2-yl) butyl]-3,4-dihydro-1H-benzo[b]azepine-2,5-dione Analogously to the method for Example 12b, 65.0 mg of the title compound were obtained from 1-(4-chlorobutyl)-3,4-dihydro-1H-1-benzazepine-2,5-dione (0.75 mmol, 0.20 g) and decahydropyrido[1,2-a][1,4]diazepine (0.75 mmol, 0.12 g; prepared according to *Pol. J. Chem.* 1985, 59, 1243-6).
ESI-MS: [M+K$^+$]=422.2, [M+H$^+$]=384.2.

Example 75

1-{4-[(1S,5R,6S)-6-(4-Fluorophenyl)-3-azabicyclo [3.2.0]hept-3-yl]butyl}-3,4-dihydro-1H-1-benzazepine-2,5-dione hydrochloride Analogously to the method for Example 3b, 0.25 g of the title compound was obtained from (1S,5R,6S)-6-(4-fluorophenyl)-3-azabicyclo[3.2.0]heptane (1.97 mmol, 0.38 g, prepared according to WO 00/23423).
$^1$H NMR (500 MHz, CDCl$_3$) δ (ppm): 7.58-7.48 (2H, m), 7.32-7.22 (m+CHCl$_3$), 7.22-7.12 (2H, m), 6.98 (2H, t), 3.92 (2H, m br.), 3.16 (1H, m br.), 3.06-2.93 (2H, m), 2.93-2.65 (6H, m; incl. t at 2.88), 2.45 (2H, t), 2.16 (2H, t), 2.09-1.92 (2H, m), 1.61 m+H$_2$O), 1.49 (2H, quint.).

Example 76

1-(4-Piperidin-1-ylbutyl)-3,4-dihydro-1H-1-benzazepine-2,5-dione hydrochloride

Analogously to the method for Example 3b, 0.02 g of the title compound was obtained from piperidine (1.24 mmol, 0.11 g).
ESI-MS: [M+H$^+$]=315.2.
In an analogous manner, the compounds of Examples 77 to 82 were prepared.

Example 77

1-[4-(2,5-Dioxo-2,3,4,5-tetrahydrobenzo[b]azepin-1-yl)butyl]-4-methylpiperidinium trifluoroacetate

ESI-MS: [M+H$^+$]=329.0.

Example 78

1-[4-(2,5-Dioxo-2,3,4,5-tetrahydrobenzo[b]azepin-1-yl)butyl]azepanium trifluoroacetate

ESI-MS: [M+H$^+$]=329.0.

Example 79

1-[4-(2,5-Dioxo-2,3,4,5-tetrahydrobenzo[b]azepin-1-yl)butyl]-3-methylpiperidinium trifluoroacetate

ESI-MS: [M+H$^+$]=329.0.

Example 80

1-[4-(2,5-dioxo-2,3,4,5-tetrahydrobenzo[b]azepin-1-yl)butyl]-4-propylpiperidinium trifluoroacetate

ESI-MS: [M+H$^+$]=357.1.

Example 81

4-[4-(2,5-Dioxo-2,3,4,5-tetrahydrobenzo[b]azepin-1-yl)butyl]morpholin-4-ium trifluoroacetate

ESI-MS: [M+H$^+$]=317.0.

Example 82

4-[4-(2,5-Dioxo-2,3,4,5-tetrahydrobenzo[b]azepin-1-yl)butyl]thiomorpholin-4-ium trifluoroacetate

ESI-MS: [M+H$^+$]=333.0.

Example 83

1-{4-[4-(2,3-Dichlorophenyl)piperazin-1-yl]butyl}-3,4-dihydro-1H-benzo[b]azepine-2,5-dione Analogously to Example 3b, reaction of 1-(4-chlorobutyl)-3,4-dihydro-1H-benzo[b]azepine-2,5-dione with 1-(2,3-dichlorophenyl)piperazine afforded the title compound.

ESI-MS: 462.4, [M+H⁺]=461.4, 460.4;
¹H NMR (400 MHz, DMSO) δ (ppm): 7.62 (1H, t), 7.51-7.45 (2H, m), 7.34 (1H, t), 7.28 (2H, m), 7.18-7.05 (1H, m), 3.88 (2H, t), 2.91 (6H, m), 2.66 (2H, m), 2.39 (4H, s br.), 2.19 (2H, t), 1.36 (2H, quint.), 1.26 (2H, quint.).

Example 84

4-(2,4-Dichlorobenzyl)-1-[4-(2,5-dioxo-2,3,4,5-tetrahydrobenzo[b]azepin-1-yl)butyl]piperazinium as the fumarate Analogously to Example 3b, reaction of 1-(4-chlorobutyl)-3,4-dihydro-1H-benzo[b]azepine-2,5-dione with 1-(2,4-dichlorobenzyl)piperazine afforded the title compound.
ESI-MS: 476.1, [M+H⁺]=475.1, 474.1, 237.6;

Example 85

1-{4-[4-(2-tert-Butyl-6-trifluoromethylpyrimidin-4-yl)piperazin-1-yl]butyl}azepane-2,5-dione a) 1-(4-Chlorobutyl)azepane-2,5-dione Analogously to Example 3a, 0.17 g of the contaminated title compound was obtained from azepane-2,5-dione (2.36 mmol, 0.30 g, preparation according to J. Photochem. 28 (1985), 569-570) and bromo-4-chlorobutane (2.83 mmol, 0.49 g). The compound is reacted further without purification.

b) 1-{4-[4-(2-tert-Butyl-6-trifluoromethylpyrimidin-4-yl)piperazin-1-yl]butyl}azepane-2,5-dione Analogously to Example 3b, 0.04 g of the title compound was obtained from 2-tert-butyl-4-piperazin-1-yl-6-trifluoromethylpyrimidine (0.59 mmol, 0.17 g) and 1-(4-chlorobutyl)azepane-2,5-dione (0.62 mmol, 0.17 g).
ESI-MS: [M+H⁺]=470.2, 235.6;
¹H NMR (400 MHz, CDCl₃) δ (ppm): 6.57 (1H, s), 3.71 (4H, s br.), 3.60-3.46 (4H, m), 2.73-2.57 (6H, m), 2.49 (4H, s br.), 2.41 (2H, s br.), 1.33 (9H, s).

Example 86

1-{4-[4-(3,5-Dichlorophenyl)-2,5-piperazin-1-yl]butyl}-3,4-dihydro-1H-benzo[b]azepine-2,5-dione fumarate In analogy to Example 3b, reaction of 1-(4-chlorobutyl)-3,4-dihydro-1H-benzo[b]azepine-2,5-dione with 1-(3,5-dichlorophenyl)piperazine afforded the title compound.
ESI-MS: 462.5, [M+H⁺]=461.5, 460.5;
¹H NMR (400 MHz, DMSO) δ (ppm): 7.62 (1H, t), 7.47 (2H, t), 7.35 (1H, t), 6.90 (2H, s), 6.85 (1H, s), 3.88 (2H, m), 3.15 (4H, m), 2.92 (2H, t), 2.67 (2H, t), 2.36 (4H, m), 2.20 (2H, t), 1.35 (2H, quint.), 1.28 (2H, quint.).

Example 87

1-{4-[4-(3,5-Bis(trifluoromethyl)phenyl)piperazin-1-yl]butyl}-3,4-dihydro-1H-benzo[b]azepine-2,5-dione fumarate In analogy to Example 3b, reaction of 1-(4-chlorobutyl)-3,4-dihydro-1H-benzo[b]azepine-2,5-dione with 1-(3,5-bis(trifluoromethyl)phenyl)piperazine afforded the title compound.
ESI-MS: [M+H⁺]=528.55;
¹H NMR (400 MHz, DMSO) δ (ppm): 7.64 (1H, t), 7.54-7.41 (4H, m), 7.34 (1H, t), 7.27 (1H, s), 3.88 (2H, m), 3.30 (4H, m br,), 2.91 (2H, t), 2.65 (2H, t), 2.40 (4H, s br,), 2.23 (2H, t), 1.36 (2H, quint.), 1.30 (2H, quint.),

B) EXAMPLES OF PHARMACEUTICAL ADMINISTRATION FORMS

Tablets:
Tablets of the following composition are compressed in a tablet press in a conventional way:
 40 mg of substance of example 2
 120 mg of corn starch
 13.5 mg of gelatin
 45 mg of lactose
 2.25 mg of Aerosil® (chemically pure silica in submicroscopically fine distribution)
 6.75 mg of potato starch (as 6% strength paste)
Sugar-Coated Tablets:
 20 mg of substance of example 2
 60 mg of core composition
 70 mg of sugar-coating composition
The core composition consists of 9 parts of corn starch, 3 parts of lactose and 1 part of vinylpyrrolidone/vinyl acetate 60:40 copolymer. The sugar-coating composition consists of 5 parts of sucrose, 2 parts of corn starch, 2 parts of calcium carbonate and 1 part of talc. The sugar-coated tablets produced in this way are subsequently provided with an enteric coating.

C) BIOLOGICAL INVESTIGATIONS—RECEPTOR BINDING STUDIES

The substance to be tested was dissolved either in methanol/Chremophor® (BASF-AG) or in dimethyl sulfoxide and then diluted with water to the desired concentration.

I. Dopamine $D_3$ Receptor:
The mixture (0.250 ml) was composed of membranes from ~10 HEK-293 cells with stably expressed human dopamine $D_3$ receptors, 0.1 nM [$^{125}$I]-iodosulpride and incubation buffer (total binding) or with additional test substance (inhibition plot) or 1 µM spiperone (nonspecific binding). Triplicate mixtures were carried out.
The incubation buffer comprised 50 mM Tris, 120 mM NaCl, 5 mM KCl, 2 mM CaCl₂, 2 mM MgCl₂ and 0.1% bovine serum albumin, 10 µM quinolone, 0.1% ascorbic acid (prepared fresh each day). The buffer was adjusted to pH 7.4 with HCl.

II. Dopamine $D_{2L}$ Receptor:
The mixture (1 ml) was composed of membranes from ~10⁶ HEK-293 cells with stably expressed human dopamine $D_{2L}$ receptors (long isoform) and 0.01 nM [$^{125}$I]-iodospiperone and incubation buffer (total binding) or with additional test substance (inhibition plot) or 1 µM haloperidol (nonspecific binding). Triplicate mixtures were carried out.
The incubation buffer comprised 50 mM Tris, 120 mM NaCl, 5 mM KCl, 2 mM CaCl₂, 2 mM MgCl₂ and 0.1% bovine serum albumin. The buffer was adjusted to pH 7.4 with HCl.

III. Measurement and Evaluation:
After incubation at 25° C. for 60 minutes, the mixtures were filtered under vacuum through Whatman GF/B glass fiber filters using a cell harvester. The filters were transferred by a filter transfer system into scintillation vials. After addition of 4 ml of Ultima Gold® (Packard), the samples were shaken for one hour and then the radioactivity was counted in a beta counter (Packard, Tricarb 2000 or 2200CA). The cp values were converted into dpm by means of a standard quench series with the aid of the instrument's own program.

Evaluation of the inhibition plots took place by iterative nonlinear regression analysis using the Statistical Analysis System (SAS) similar to the "LIGAND" program described by Munson and Rodbard.

In these assays, the inventive compounds show very good affinities for the $D_3$ receptor (<100 nM, frequently <50 nM) and bind selectively to the $D_3$ receptor.

The results of the binding assays are indicated in table 1.

TABLE 1

| Example | $K_i$ ($D_3$) [nM] | Selectivity vs. $D_2L$* |
|---------|--------------------|-----------------------|
| 3       | 0.83               | 296                   |
| 4       | 1.74               | 155                   |
| 6       | 4.50               | 104                   |
| 7       | 1.33               | 118                   |
| 10      | 1.24               | 74                    |
| 16      | 0.96               | 62                    |
| 86      | 2.0                | 56                    |
| 87      | 7.4                | 129                   |

*$K_i(D_2L)/K_i(D_3)$

What is claimed is:

1. A compound of the formula I

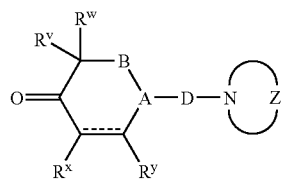

(I)

where

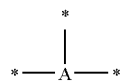

is a group of the formulae

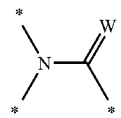

where D is bonded to the nitrogen atom and where

W is O, S or an N—$R^z$ group where $R^z$ is selected from optionally substituted $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_3$-$C_6$-cycloalkyloxy, $C_3$-$C_6$-cycloalkyl-$C_1$-$C_4$-alkyloxy and optionally substituted phenyl and * denotes the bonding sites;

—B— is

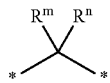

where $R^m$ and $R^n$ are each independently selected from hydrogen, halogen, optionally substituted $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_3$-$C_6$-cycloalkyloxy, $C_3$-$C_6$-cycloalkyl-$C_1$-$C_4$-alkyloxy and optionally substituted phenyl, or, when the nitrogen in the A group is bonded to B, may also be a carbonyl group, and * denotes the bonding sites;

----- represents a single bond or a double bond;

$R^v$, $R^w$ are each independently hydrogen, halogen, optionally substituted $C_1$-$C_6$-alkyl, $C_1$-$C_6$-alkoxy, $C_2$-$C_6$-alkenyl, $C_2$-$C_6$-alkynyl, $C_3$-$C_6$-cycloalkyloxy, $C_3$-$C_6$-cycloalkyl-$C_1$-$C_4$-alkyloxy or $C_3$-$C_6$-cycloalkyl; or $R^x$, $R^y$ together with the carbon atoms to which they are bonded, form a fused phenyl ring where the fused phenyl ring may have 1, 2 or 3 substituents which are selected from optionally substituted $C_1$-$C_6$-alkyl, CN, $OR^1$, $NR^2R^3$, $NO_2$, $SR^4$, $SO_2R^4$, $SO_2NR^2R^3$, $CONR^2R^3$, $COOR^5$, $COR^6$, $C_1$-$C_4$-haloalkoxy, $C_2$-$C_6$-alkenyl, $C_2$-$C_6$-alkynyl, $C_2$-$C_6$-alkenyloxy, $C_2$-$C_6$-alkynyloxy, $C_3$-$C_6$-cycloalkyl, $C_3$-$C_6$-cycloalkyloxy and halogen;

where $R^1$, $R^2$, $R^3$, $R^4$, $R^5$ and $R^6$ are each independently H, optionally substituted $C_1$-$C_6$-alkyl or optionally substituted phenyl, where $R^3$ may also be a $COR^7$ group where $R^7$ is hydrogen, optionally substituted $C_1$-$C_4$-alkyl or optionally substituted phenyl, where $R^2$ with $R^3$ may also together form a 5- or 6-membered, saturated or unsaturated carbocycle which may have a heteroatom selected from O, S and $NR^8$ as a ring member, where $R^8$ is hydrogen or $C_1$-$C_4$-alkyl, D is a linear or branched 2- to 10-membered alkylene chain which may have, as chain members, a heteroatom group K which is selected from O, S, S(O), S(O)$_2$, N—$R^8$, CO—O, C(O)$NR^8$, and/or 1 or 2 nonadjacent carbonyl groups and which may include a cycloalkanediyl group and/or may have a double or triple bond;

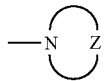

is a saturated or monounsaturated, monocyclic nitrogen heterocycle having from 5 to 8 ring members or a bicyclic saturated nitrogen heterocycle having from 7 to 12 ring members, where the mono- and the bicyclic nitrogen heterocycle optionally has, as a ring member, a further heteroatom selected from oxygen, sulfur or nitrogen, where the mono- or bicyclic nitrogen heterocycle bears an $R^a$ radical, where $R^a$ is an E-Ar group wherein E is a bond or linear or branched alkylene having from 1 to 4 carbon atoms and in particular $(CH_2)_p$ where p is 0, 1, 2, 3 or 4, and Ar is selected from phenyl, naphthyl and 5- or 6-membered heteroaryl which has one, two or three heteroatoms selected from S, O and N as ring members and which may optionally have 1, 2 or 3 substituents $R^b$ which are each independently selected from $C_1$-$C_6$-alkyl, $C_2$-$C_6$-alkenyl, $C_2$-$C_6$-alkynyl, $C_3$-$C_6$-cycloalkyl, $C_4$-$C_{10}$-bicycloalkyl and $C_6$-$C_{10}$-tricycloalkyl, where the last three groups may optionally be substituted by halogen or $C_1$-$C_4$-alkyl, halogen, CN, OR$^1$, NR$^2$R$^3$, NO$_2$, SR$^4$, SO$_2$R$^5$, CONR$^2$R$^3$, SO$_2$NR$^2$R$^3$, COOR$^5$, COR$^6$, O—COR$^6$, 5- or 6-membered saturated, partly unsaturated or aromatic heterocyclyl having 1, 2 or 3 heteroatoms selected from O, S and N, and phenyl, where phenyl and heterocyclyl in the last two substituents R$^b$ may optionally bear one or two substituents which are each independently selected from C$_1$-C$_4$-alkyl, C$_1$-C$_4$-alkoxy, NR$^2$R$^3$, CN, C$_1$-C$_2$-fluoroalkyl and halogen, and where 2 substituents R$^b$ bonded to adjacent carbon atoms of the aromatic radical may together be C$_3$- or C$_4$-alkylene, or, together with the carbon atoms to which they are bonded, may be a fused-on, unsaturated 5- or 6-membered carbocycle or a 5- or 6-membered heterocycle where the term "optionally substituted phenyl" in the definition of R$^z$, R$^m$, R$^n$, R$^v$, R$^w$, R$^1$, R$^2$, R$^3$, R$^4$, R$^5$, R$^6$ and R$^7$ is unsubstituted phenyl or phenyl which has 1, 2 or 3, of the following substituents: halogen, nitro, cyano, C$_1$-C$_4$-alkyl, C$_1$-C$_4$-haloalkyl, C$_2$-C$_6$-alkenyl, C$_2$-C$_6$-alkynyl, C$_3$-C$_6$-cycloalkyl, C$_1$-C$_4$-haloalkyl, C$_1$-C$_4$-alkoxy, OR$^{21}$, COOR$^{21}$, NR$^{22}$R$^{23}$, SO$_2$NR$^{22}$R$^{23}$, CONR$^{22}$R$^{23}$, O—CONR$^{22}$R$^{23}$, S—R$^{24}$, SOR$^{25}$, SO$_2$R$^{25}$, OCOR$^{26}$ and COR$^{26}$, where R$^{21}$ to R$^{26}$ are hydrogen, C$_1$-C$_4$-alkyl, C$_1$-C$_4$-haloalkyl, C$_3$-C$_7$-cycloalkyl, benzyl or phenyl;

where the term "optionally substituted alkyl" in the definition of R$^z$, R$^m$, R$^n$, R$^v$, R$^w$, R$^1$, R$^2$, R$^3$, R$^4$, R$^5$, R$^6$ and R$^7$ is alkyl which may have 1, 2 or 3 substituents which are selected from OH, C$_1$-C$_4$-alkoxy, halogen, C$_3$-C$_7$-cycloalkyl and optionally substituted phenyl;

the physiologically acceptable acid addition salts of this compound and the tautomer of the formula I'

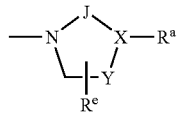
(I')

where R is halogen, an O—R$^1$ group where R$^1$ is as defined above, or an O—C(O)R$^9$ group where R$^9$ is hydrogen, optionally substituted C$_1$-C$_6$-alkyl, benzyl or phenyl, where the last two radicals are optionally substituted by one or two radicals which are each independently selected from C$_1$-C$_4$-alkyl, OH, C$_1$-C$_4$-alkoxy, NR$^2$R$^3$, CN, C$_1$-C$_2$-fluoroalkyl or halogen, and the physiologically acceptable acid addition salts of the tautomer I'.

2. A compound as claimed in claim 1, where D in the formulae I and I' is a (CH$_2$)$_k$ group or a C(O)(CH$_2$)l group, where k is 3, 4, 5 or 6 and l is 2, 3, 4 or 5.

3. A compound as claimed in claim 1, where A is N—C(O) in which the carbon atom is bonded to the variable B.

4. A compound as claimed in claim 3, where B is CH$_2$.

5. A compound of the formula I or I' as claimed in claim 1, where is a radical of the formula where

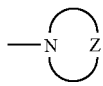

is a radical of the formula

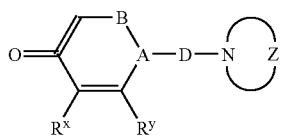

where R$^a$ is as defined above, and
J is CH$_2$, CH$_2$—CH$_2$ or CH$_2$—CH$_2$—CH$_2$;
X is CH or N and
Y is CH$_2$, CH$_2$—CH$_2$ or CH$_2$—CH$_2$—CH$_2$, or Y—X together is CH═C or CH$_2$—CH═C;
R$^e$ is hydrogen or C$_1$-C$_4$-alkyl.

6. A compound as claimed in claim 5, where J is CH$_2$—CH$_2$ and Y is CH$_2$.

7. A compound as claimed in claim 5, where X is N.

8. A compound as claimed in claim 1, where E is a bond.

9. A compound as claimed in claim 8, where Ar is phenyl, pyridyl, pyrimidinyl or s-triazinyl, each of which has 1, 2 or 3 of the aforementioned Rb radicals.

10. A compound of the formula I-Aa

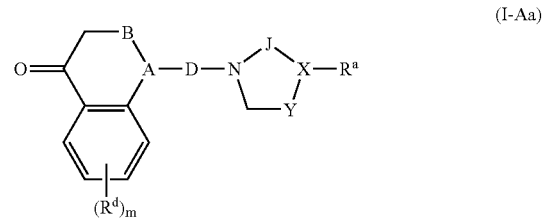
(I-Aa)

where R$^a$, A, B and D are each as defined in claim 1;
m is 0, 1, 2 or 3;
R$^d$ are each independently C$_1$-C$_4$-alkyl, C$_1$-C$_4$-hydroxyalkyl, C$_1$-C$_4$-alkoxy-C$_1$-C$_4$-alkyl, CN, OR$^1$, NR$^2$R$^3$, NO$_2$, SR$^4$, SO$_2$R$^4$, SO$_2$NR$^2$R$^3$, CONR$^2$R$^3$, COOR$^5$, COR$^6$, C$_1$-C$_2$-fluoroalkyl, C$_1$-C$_2$-fluoroalkoxy, C$_2$-C$_6$-alkenyl, C$_2$-C$_6$-alkynyl, C$_2$-C$_6$-alkenyloxy, C$_2$-C$_6$-alkynyloxy, C$_3$-C$_6$-cycloalkyl, C$_3$-C$_6$-cycloalkyl or halogen, where R$^1$, R$^2$, R$^3$, R$^4$, R$^5$ and R$^6$ are each as defined in claim 1;
J is CH$_2$, CH$_2$—CH$_2$ or CH$_2$—CH$_2$—CH$_2$;
X is CH or N and
Y is CH$_2$, CH$_2$—CH$_2$ or CH$_2$—CH$_2$—CH$_2$, or Y—X together is CH═C or CH$_2$—CH═C;
the physiologically acceptable acid addition salts of this compound and the tautomer of the formula I-A'a

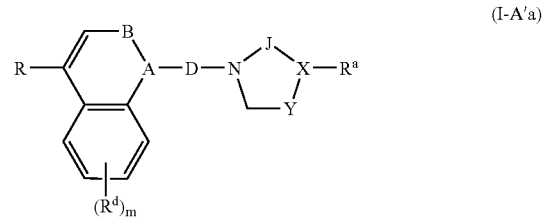
(I-A'a)

where R is as defined in claim 1 and the physiologically acceptable acid addition salts of the tautomer Ia'.

11. A compound as claimed in claim 10, where J is CH$_2$—CH$_2$ and Y is CH$_2$.

12. A compound as claimed in claim 10, where X is N.

13. A compound as claimed in claim 10 where E is a bond.

14. A compound as claimed in claim 13, where Ar is phenyl, pyridyl, pyrimidinyl or s-triazinyl, each of which has 1, 2 or 3 of the aforementioned $R^b$ radicals.

15. A pharmaceutical composition comprising at least one active ingredient which is selected from compounds of the formula I, the tautom-ers of the formula I', the physiologically tolerated acid addition salts of the com-pounds I and the physiologically tolerated acid addition salts of the tautomers of the formula I' as claimed in claim 1, optionally together with physiologically ac-ceptable carriers and/or excipients.

16. The compound according to claim 10, wherein
J is $CH_2$—$CH_2$;
X is N
Y is $CH_2$;
and wherein
$R^a$ is a radical E-Ar, wherein E is a bond and Ar is selected from phenyl, pyridyl, pyrimidinyl and s-triazinyl, each of which has 1, 2 or 3 of the aforementioned $R^b$ radicals.

17. The compound according to claim 16, wherein $R^a$ is a radical Ar-1

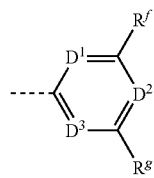

Ar-1 wherein $D^1$ and $D^2$ are N and $D^3$ is CH and wherein
$R^f$ and $R^g$ are each independently selected from the following groups: $OR^1$, $NR^2R^3$, CN, $C_1$-$C_6$-alkyl which is optionally substituted by OH, $C_1$-$C_4$-alkoxy, halogen or phenyl, $C_2$-$C_6$-alkenyl, $C_2$-$C_6$-alkynyl, $C_3$-$C_6$-cycloalkyl, $C_4$-$C_{10}$-bicycloalkyl, $C_6$-$C_{10}$-tricycloalkyl, where the last three groups may optionally be substituted by halogen or $C_1$-$C_4$-alkyl, halogen, CN, $OR^1$, 5- or 6-membered het-erocyclyl having 1, 2 or 3 heteroatoms selected from O, S and N, and phenyl, where phenyl and heterocyclyl optionally bear one or two substituents which are each independently selected from $C_1$-$C_4$-alkyl, $C_1$-$C_4$-alkoxy, $NR^2R^3$, CN, $C_1$-$C_2$-fluoroalkyl and halogen.

18. The compound according to claim 10, which is of the formula I-Aa

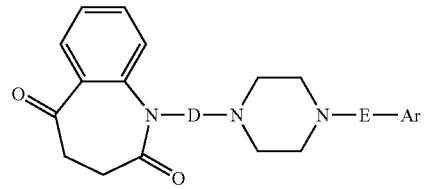

(I-Aa.a)

wherein E is a bond and Ar is selected from phenyl, pyridyl, pyrimidinyl and s-triazinyl, each of which has 1, 2 or 3 of the aforementioned $R^b$ radicals.

19. The compound according to claim 17, wherein Ar is a radical A-1

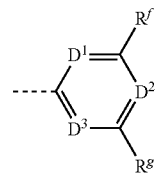

Ar-1 wherein $D^1$ and $D^2$ are N and $D^3$ is CH and wherein
$R^f$ and $R^g$ are each independently selected from the following groups: $OR^1$, $NR^2R^3$, CN, $C_1$-$C_6$-alkyl which is optionally substituted by OH, $C_1$-$C_4$-alkoxy, halogen or phenyl, $C_2$-$C_6$-alkenyl, $C_2$-$C_6$-alkynyl, $C_3$-$C_6$-cycloalkyl, $C_4$-$C_{10}$-bicycloalkyl, $C_6$-$C_{10}$-tricycloalkyl, where the last three groups may optionally be substituted by halogen or $C_1$-$C_4$-alkyl, halogen, CN, $OR^1$, 5- or 6-membered heterocyclyl having 1, 2 or 3 heteroatoms selected from O, S and N, and phenyl, where phenyl and heterocyclyl optionally bear one or two substituents which are each independently selected from $C_1$-$C_4$-alkyl, $C_1$-$C_4$-alkoxy, $NR^2R^3$, CN, $C_1$-$C_2$-fluoroalkyl and halogen.

* * * * *